US011584941B2

(12) United States Patent
Beekwilder et al.

(10) Patent No.: US 11,584,941 B2
(45) Date of Patent: Feb. 21, 2023

(54) TERPENE SYNTHASE PRODUCING PATCHOULOL AND ELEMOL, AND PREFERABLY ALSO POGOSTOL

(71) Applicant: ISOBIONICS B.V., Geleen (NL)

(72) Inventors: Martinus Julius Beekwilder, Renkum (NL); Adèle Margaretha Maria Liduina Van Houwelingen, Wekerom (NL); Hendrik Jan Bosch, Wageningen (NL); Georg Friedrich Lentzen, Geleen (NL); Elena Melillo, Geleen (NL)

(73) Assignee: ISOBIONICS B.V., Geleen (NL)

( * ) Notice: Subject to any disclaimer, the term of this patent is extended or adjusted under 35 U.S.C. 154(b) by 0 days.

(21) Appl. No.: 16/643,740

(22) PCT Filed: Sep. 1, 2018

(86) PCT No.: PCT/NL2018/050565
§ 371 (c)(1),
(2) Date: Mar. 2, 2020

(87) PCT Pub. No.: WO2019/045568
PCT Pub. Date: Mar. 7, 2019

(65) Prior Publication Data
US 2021/0102224 A1    Apr. 8, 2021

(30) Foreign Application Priority Data
Sep. 1, 2017    (NL) .................................... 2019473

(51) Int. Cl.
*C12N 15/63*    (2006.01)
*C12P 7/02*    (2006.01)
*C12N 9/88*    (2006.01)
*C12N 15/80*    (2006.01)

(52) U.S. Cl.
CPC ................. *C12P 7/02* (2013.01); *C12N 9/88* (2013.01); *C12N 15/80* (2013.01); *C12Y 402/0307* (2013.01)

(58) Field of Classification Search
None
See application file for complete search history.

(56) References Cited

U.S. PATENT DOCUMENTS

| 8,993,284 B2 | 3/2015 | Zu et al. | |
| 2006/0206957 A1* | 9/2006 | Schalk | C12P 15/00 800/278 |
| 2009/0205060 A1 | 8/2009 | Schalk et al. | |

FOREIGN PATENT DOCUMENTS

| WO | 2011/141855 A1 | 11/2011 |
| WO | 2014/206412 A1 | 12/2014 |

OTHER PUBLICATIONS

V.K. Purohit et al. "Volitle Constituents of Endangered Species Nardostachys grandiflora DC Rhizomes From Uttarakhand Himilaya (India)", Indian Journal of Natural Products and Resources 6(2):134-137. (Year: 2015).*
S.L. Munck et al. "Purification and Characterization of the Sesquiterpene Cyclase Patchoulol Synthase from Pogostemon cablin", Archives of biochemistry and biophysics 282(1):58-64 (Year: 1990).*
Choudhary, et al., "Volatile Constituents of the Aerial and Underground Parts of Curcuma aromatica Salisb from India", Journal of Essential Oil Research, vol. 8, Issue 6, Jan. 1, 1996, pp. 633-638.
Daviet, et al., "Biotechnology in plant essential oil production: progress and perspective in metabolic engineering of the terpene pathway", Flavour and Fragrance Journal, vol. 25, Issue 3, Feb. 19, 2010, pp. 123-127.
Deguerry, et al., "The diverse sesquiterpene profile of patchouli, Pogostemon cablin, is correlated with a limited number of sesquiterpene synthases", Archives of Biochemistry and Biophysics, vol. 454, Issue 2, Oct. 15, 2006, pp. 123-136.
I.R. Booth, "Regulation of cytoplasmic pH in bacteria", Microbiological Reviews, vol. 49, Issue 4, 1985, pp. 359-378.
Author Unknown International Search Report for PCT Patent Application No. PCT/NL2018/050565, dated Jan. 14, 2019, 6 pages.
John C. Leffingwell, "Chirality and odor perception-Scents of precious woods", Chimica Oggi-Chemistry Today, vol. 24, Issue 4, 2006, pp. 36-38.
Lange, et al., "Metabolic engineering of plant monoterpenes, sesquiterpenes and diterpenes—current status and future opportunities", Plant Biotechnology Journal, vol. 11, Issue 2, Nov. 21, 2012, pp. 169-196.
John C. Leffingwell, et al., "Biotechnology—Conquests and Challenges in Flavors & Fragrances", Leffingwell Reports, vol. 7, Issue 2, Mar. 2015, pp. 1-11.
Naf, et al., "A Stereocontrolled Access to (±)-, (−)-, and (+)-Patchouli Alcohol", Helvetica Chimica Acta, vol. 64, Issue 5, Jul. 22, 1981, pp. 1387-1397.
Olsen, et al., "Noninvasive Measurement of Bacterial Intracellular pH on a Single-Cell Level with Green Fluorescent Protein and Fluorescence Ratio Imaging Microscopy", Applied and Environmental Microbiology, vol. 68, Issue 8, Aug. 2002, pp. 4145-4147.
Srikrishna, et al., "An enantiospecific total synthesis of (−)-patchouli alcohol", Tetrahedron: Asymmetry, vol. 16, Issue 24, Dec. 12, 2005, pp. 3992-3997.
Wu, et al., "Redirection of cytosolic or plastidic isoprenoid precursors elevates terpene production in plants", Nature Biotechnology, vol. 24, Issue 11, Nov. 2006, pp. 1441-1447.

(Continued)

*Primary Examiner* — Richard G Hutson
(74) *Attorney, Agent, or Firm* — Faegre Drinker Biddle & Reath LLP

(57) ABSTRACT

The invention is directed to a patchoulol synthase, to a nucleic acid encoding said patchoulol synthase, to an expression vector comprising said nucleic acid, to a host cell comprising said expression vector, to a method of preparing patchoulol and elemol, and preferably also pogostol, and to a method of preparing a patchoulol synthase.

20 Claims, 8 Drawing Sheets

Figure 1:
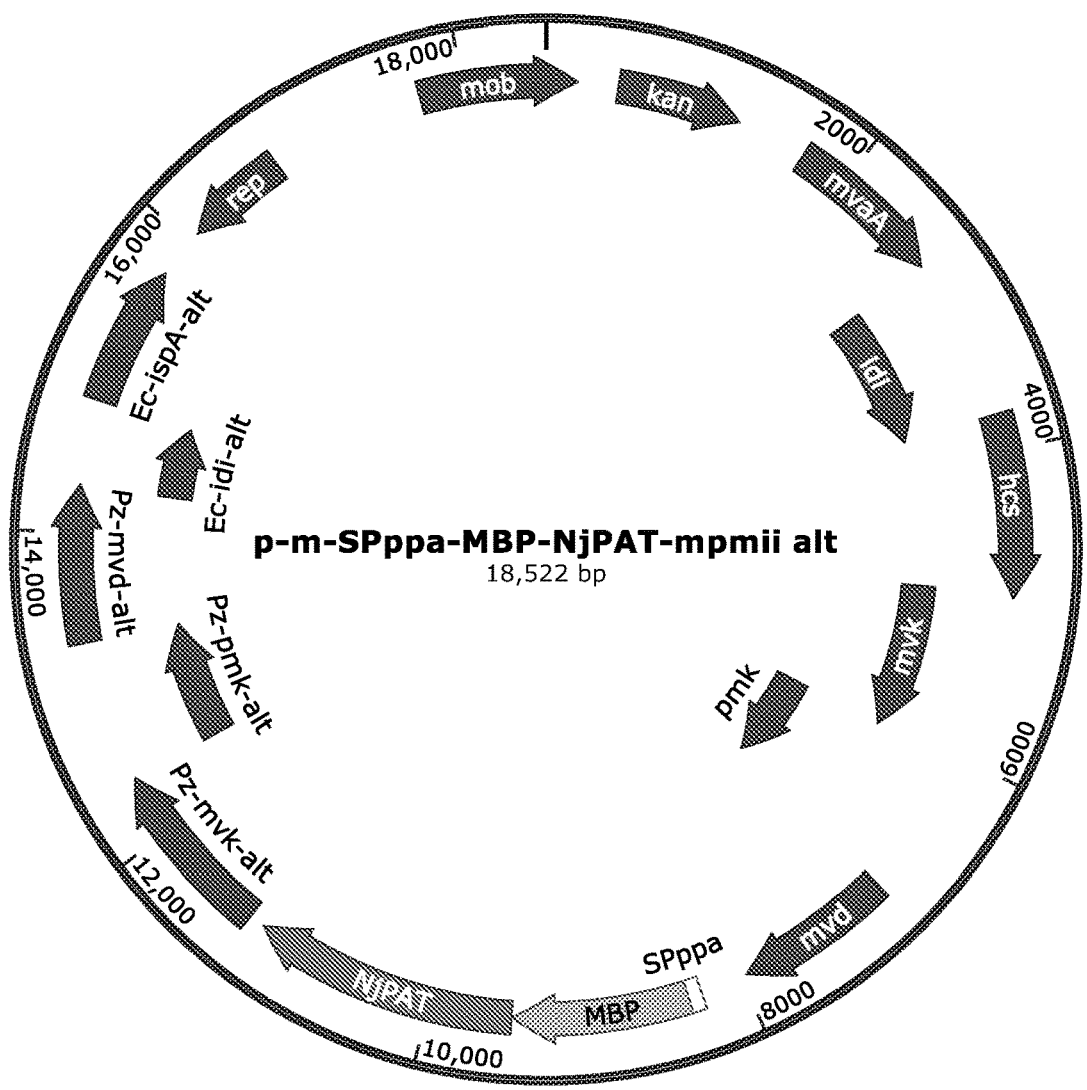

Specification includes a Sequence Listing.

(56) References Cited

OTHER PUBLICATIONS

Zhan, et al., "Metabolic engineering of the moss Physcomitrella patens to produce the sesquiterpenoids patchoulol and α/β-santalene", Frontiers in Plant Science, vol. 5, Issue 636, Nov. 18, 2014, pp. 1-10.
Beekwilder et al., "Valencene synthase from the heartwood of Nootka cypress (Callitropsis nootkatensis) for biotechnological production of valencene", Plant Biotechnology Journal, vol. 12, (2014), pp. 174-182.
Chatterjee et al., "An Overview of the Genus Nardostachys", Natural Product Communications, vol. 2, No. 11, pp. 1163-1173.
Chauhan et al., "Effect of Post Harvest Drying Methods on the Essential Oil Composition of Nardostachys jatamansi DC ", Journal of Essential Oil Bearing Plants, vol. 20 No. 4, pp. 1090-1096.
Httan et al., "Identification of a novel hedycaryol synthase gene isolated from *Camellia brevistyla* flowers and floral scent of *Camellia* cultivars", Planta, vol. 243, 2016, pp. 959-972.
Kwon et al., "Molecular cloning and characterization of drimenol synthase from valerian plant (*Valeriana officinalis*)", FEBS Letters, vol. 588, 2014, pp. 4597-4603.
Scholtmeijer et al., "Production of (+)-valencene in the mushroom-forming fungus *S. commune*", Appl Microbiol Biotechnol, vol. 98, 2014, 5059-5068.
Hartwig et al., "Expression, purification and activity assay of a patchoulol synthase cDNA variant fused to thioredoxin in *Escherichia coli*", Protein Expression and Purification, vol. 97, May 2014, pp. 61-71.

* cited by examiner

SEQUENCE LISTING

```
<160> NUMBER OF SEQ ID NOS: 31

<210> SEQ ID NO 1
<211> LENGTH: 49
<212> TYPE: DNA
<213> ORGANISM: Artificial Sequence
<220> FEATURE:
<223> OTHER INFORMATION: 27692-fw Nucleotide sequence

<400> SEQUENCE: 1
atatgagctc aatgtcaatt attattgcaa caaacagtac tgagcatcc          49

<210> SEQ ID NO 2
<211> LENGTH: 51
<212> TYPE: DNA
<213> ORGANISM: Artificial Sequence
<220> FEATURE:
<223> OTHER INFORMATION: 27692-re Nucleotide sequence

<400> SEQUENCE: 2
atatgcggcc gcttatatgg atacgggatc tacgaacaac gatatgatgt g        51

<210> SEQ ID NO 3
<211> LENGTH: 1677
<212> TYPE: DNA
<213> ORGANISM: Nardostachys jatamansii

<400> SEQUENCE: 3
atgtcaatta ttattgcaac aaacagtact gagcatccaa tttttcgtcc attagcaaat    60
tttccaccaa gtttatgggg caatcttttc acttcattct ccatggataa tcaggctagg   120
gaaatatatg ctaaagaaca tgaaggttta aaagaaaaag tgagaatgat gttttagat   180 acaacaaatt acaaaatttc agagaaaatc aatttcataa acacagtgga aagattaggt   240
gtatcatatc attttgagaa agagattgaa gaactacttc atcaaatgtt tgatgctcat   300
tctaaacacc tagatgatat tcaagaattt gatttgttca ctttgggaat ttacttcagg   360
attctaaggc aacatggtta taaatctct tgtgatgttt tcaataagtt gaaagatagc   420
aatggcgaat tcaaggacga acttaaagat gatgtgaatg gtatgctaag tttctatgaa   480
gcaacacatg taagaacaca tggagaaaat attttagatg aagctctcat ttatacaaaa   540
gctcaacttg aatccatggc cgctgcaagt ttaagcccat ttctcgcgaa ccaagttaag   600
catgctttga tgcaagctct ccacaaaggg atcccaagaa tcgaagcacg taactatatc   660
```

-continued

| | |
|---|---|
| tctgtttacg aagaagatcc taacaaaaat gatttgttat tgaggttctc aaagatagat | 720 |
| ttcaatctag tacaaatgat tcacaagcaa gaattgtgcg ataccttag gtggtggaaa | 780 |
| gatttggagt tcgaatcgaa actatctttt gcaaggaata gagtggtgga agcctactta | 840 |
| tggactctta gcgcgtacta cgaaccaaaa tactcttccg ctcggattat attagtcaaa | 900 |
| ctaatggtta taatatctgt tacggatgac acatatgatg catatggtac attagatgaa | 960 |
| cttcaacttt ttacagatgc aatacaaagg ttggatatga gttctatcaa tcaacttcca | 1020 |
| gattacatga agaccatcta taaagctctc ctagatcttt ttgacgaaat agaagatcga | 1080 |
| ttatcgaagc atgaaactga tcattcttac cgcgttgctt atgcgaaata tgtgtataaa | 1140 |
| gagatcgtta ggtgctacga tatggagtac aaatggttca acaaaaatta cgtgccggca | 1200 |
| tttgaagaat atatgcagaa agcgttagtc acatcaggta accgtttgct cataacgttt | 1260 |
| tcctttctgg gaatggacga agtcgcaact attcaagcgt tcgagtgggt aaaaagtaat | 1320 |
| gccaaaatga tagtctcttc caataaagta ttacgactta ttgatgacat aatgagtcac | 1380 |
| gaggaagagg atgaaagggg acatgttgca acagggattg aatgctttgt aaaagaacat | 1440 |
| ggactaacta gggaagaggt tatcgttgaa tttcataaga ggattgatga tgcttggaag | 1500 |
| gatataaatg aggaatttat aacgccaaat aatttaccga ttgagatact tacgcgtgtt | 1560 |
| ctaaaccta caagaattgg agatgttgtt tacaagtatg atgacgggta tactcatccg | 1620 |
| gagaaagcgt tgaaagatca catcatatcg ttgttcgtag atcccgtatc catataa | 1677 |

```
<210> SEQ ID NO 4
<211> LENGTH: 558
<212> TYPE: PRT
<213> ORGANISM: Nardostachys jatamansii

<400> SEQUENCE: 4
```

Met Ser Ile Ile Ile Ala Thr Asn Ser Thr Glu His Pro Ile Phe Arg
1               5                   10                  15

Pro Leu Ala Asn Phe Pro Pro Ser Leu Trp Gly Asn Leu Phe Thr Ser
            20                  25                  30

Phe Ser Met Asp Asn Gln Ala Arg Glu Ile Tyr Ala Lys Glu His Glu
        35                  40                  45

Gly Leu Lys Glu Lys Val Arg Met Met Phe Leu Asp Thr Thr Asn Tyr
    50                  55                  60

Lys Ile Ser Glu Lys Ile Asn Phe Ile Asn Thr Val Glu Arg Leu Gly
65                  70                  75                  80

Val Ser Tyr His Phe Glu Lys Glu Ile Glu Glu Leu Leu His Gln Met
                85                  90                  95

Phe Asp Ala His Ser Lys His Leu Asp Asp Ile Gln Glu Phe Asp Leu
            100                 105                 110

Phe Thr Leu Gly Ile Tyr Phe Arg Ile Leu Arg Gln His Gly Tyr Lys
        115                 120                 125

Ile Ser Cys Asp Val Phe Asn Lys Leu Lys Asp Ser Asn Gly Glu Phe
    130                 135                 140

Lys Asp Glu Leu Lys Asp Asp Val Asn Gly Met Leu Ser Phe Tyr Glu
145                 150                 155                 160

Ala Thr His Val Arg Thr His Gly Glu Asn Ile Leu Asp Glu Ala Leu
                165                 170                 175

Ile Tyr Thr Lys Ala Gln Leu Glu Ser Met Ala Ala Ala Ser Leu Ser
            180                 185                 190

Pro Phe Leu Ala Asn Gln Val Lys His Ala Leu Met Gln Ala Leu His 195                 200                 205
Lys Gly Ile Pro Arg Ile Glu Ala Arg Asn Tyr Ile Ser Val Tyr Glu
    210                 215                 220

Glu Asp Pro Asn Lys Asn Asp Leu Leu Leu Arg Phe Ser Lys Ile Asp
225                 230                 235                 240

Phe Asn Leu Val Gln Met Ile His Lys Gln Glu Leu Cys Asp Thr Phe
                245                 250                 255

Arg Trp Trp Lys Asp Leu Glu Phe Glu Ser Lys Leu Ser Phe Ala Arg
            260                 265                 270

Asn Arg Val Val Glu Ala Tyr Leu Trp Thr Leu Ser Ala Tyr Tyr Glu
        275                 280                 285

Pro Lys Tyr Ser Ser Ala Arg Ile Ile Leu Val Lys Leu Met Val Ile
    290                 295                 300

Ile Ser Val Thr Asp Asp Thr Tyr Asp Ala Tyr Gly Thr Leu Asp Glu
305                 310                 315                 320

Leu Gln Leu Phe Thr Asp Ala Ile Gln Arg Leu Asp Met Ser Ser Ile
                325                 330                 335

Asn Gln Leu Pro Asp Tyr Met Lys Thr Ile Tyr Lys Ala Leu Leu Asp
            340                 345                 350

Leu Phe Asp Glu Ile Glu Asp Arg Leu Ser Lys His Glu Thr Asp His
        355                 360                 365

Ser Tyr Arg Val Ala Tyr Ala Lys Tyr Val Tyr Lys Glu Ile Val Arg
    370                 375                 380

Cys Tyr Asp Met Glu Tyr Lys Trp Phe Asn Lys Asn Tyr Val Pro Ala
385                 390                 395                 400

Phe Glu Glu Tyr Met Gln Lys Ala Leu Val Thr Ser Gly Asn Arg Leu
                405                 410                 415

Leu Ile Thr Phe Ser Phe Leu Gly Met Asp Glu Val Ala Thr Ile Gln
            420                 425                 430

Ala Phe Glu Trp Val Lys Ser Asn Ala Lys Met Ile Val Ser Ser Asn
        435                 440                 445

Lys Val Leu Arg Leu Ile Asp Asp Ile Met Ser His Glu Glu Glu Asp
    450                 455                 460

Glu Arg Gly His Val Ala Thr Gly Ile Glu Cys Phe Val Lys Glu His
465                 470                 475                 480

Gly Leu Thr Arg Glu Glu Val Ile Val Glu Phe His Lys Arg Ile Asp
                485                 490                 495

Asp Ala Trp Lys Asp Ile Asn Glu Glu Phe Ile Thr Pro Asn Asn Leu
            500                 505                 510

Pro Ile Glu Ile Leu Thr Arg Val Leu Asn Leu Thr Arg Ile Gly Asp
        515                 520                 525

Val Val Tyr Lys Tyr Asp Asp Gly Tyr Thr His Pro Glu Lys Ala Leu
    530                 535                 540

Lys Asp His Ile Ile Ser Leu Phe Val Asp Pro Val Ser Ile
545                 550                 555

<210> SEQ ID NO 5
<211> LENGTH: 1677
<212> TYPE: DNA
<213> ORGANISM: Artificial Sequence
<220> FEATURE:
<223> OTHER INFORMATION: NjPAT codon optimized Nucleotide sequence

<400> SEQUENCE: 5
atgtcgatca tcatcgccac caacagcacc gagcatccca tcttccgccc gctcgccaac      60

```
ttcccgccgt cgctctgggg caacctgttc acctcgttca gcatggacaa ccaggcgcgc    120
gagatctacg ccaaggagca cgagggcctc aaggagaagg tccggatgat gttcctggac    180
accacgaact acaagatctc ggagaagatc aacttcatca acaccgtcga gcgcctgggc    240
gtgagctatc acttcgagaa ggagatcgag gagctgctcc atcagatgtt cgacgcccac    300
tcgaagcatc tggacgacat ccaggagttc gacctcttca cgctgggcat ctacttccgc    360
atcctgcggc agcatggcta taagatctcg tgcgacgtct tcaacaagct gaaggacagc    420
aacggcgagt tcaaggacga gctcaaggac gacgtcaacg gcatgctgtc gttctatgag    480
gccacccatg tgcgcaccca tggcgagaac atcctgacg aggcgctgat ctacacgaag    540
gcccagctgg agtcgatggc ggccgcctcg ctcagcccgt tcctggccaa ccaggtgaag    600
cacgcgctca tgcaggccct gcataagggc atcccgcgca tcgaggcgcg gaactacatc    660
tcggtctatg aggaagaccc gaacaagaac gacctgctcc tgcgcttcag caagatcgac    720
ttcaacctgg tgcagatgat ccacaagcag gagctgtgcg acaccttccg gtggtggaag    780
gacctggagt tcgagtcgaa gctgtcgttc gcccgcaacc gggtggtgga ggcctacctc    840
tggacgctgt cggcgtacta tgagccgaag tattcgagcg cccgcatcat cctcgtgaag    900
ctgatggtca tcatctcggt gaccgacgac acgtacgacg cctatggcac cctggacgag    960
ctccagctgt tcacggacgc gatccagcgc ctcgacatgt cgagcatcaa ccagctgccc   1020
gactacatga agaccatcta taaggcgctc ctggacctct tcgacgagat cgaggaccgc   1080
ctgtcgaagc acgagacgga ccatagctac cgggtggcgt atgccaagta cgtctataag   1140
gagatcgtgc gctgctacga catggagtat aagtggttca acaagaacta cgtccccgcc   1200
ttcgaggagt atatgcagaa ggccctggtg acctcgggca accggctcct gatcacgttc   1260
agcttcctgg gcatggacga ggtcgcgacc atccaggcct cgagtgggt gaagtcgaac   1320 gccaagatga tcgtgtcgtc gaacaaggtg ctccgcctga tcgacgacat catgtcgcac   1380
gaggaagagg acgagcgcgg ccatgtggcc acgggcatcg agtgcttcgt gaaggagcac   1440
ggcctgaccc gcgaggaagt gatcgtcgag ttccataagc ggatcgacga cgcgtggaag   1500
gacatcaacg aggagttcat caccccgaac aacctgccga tcgagatcct gacccgcgtg   1560
ctcaacctga cccggatcgg cgacgtggtc tacaagtatg acgacggcta cacgcacccc   1620
gagaaggccc tcaaggacca tatcatcagc ctgttcgtgg accccgtcag catctga      1677

<210> SEQ ID NO 6
<211> LENGTH: 44
<212> TYPE: DNA
<213> ORGANISM: Artificial Sequence
<220> FEATURE:
<223> OTHER INFORMATION: Pppa_Fw Nucleotide sequence

<400> SEQUENCE: 6
actggcctca gaattcaaat ttatttgctt tgtgagcgga taac                      44

<210> SEQ ID NO 7
<211> LENGTH: 25
<212> TYPE: DNA
<213> ORGANISM: Artificial Sequence
<220> FEATURE:
<223> OTHER INFORMATION: MBP_NjPAT_Rv Nucleotide sequence

<400> SEQUENCE: 7
ggcgatgatg atcgacatga tcttg                                           25
```

<210> SEQ ID NO 8
<211> LENGTH: 24
<212> TYPE: DNA
<213> ORGANISM: Artificial Sequence
<220> FEATURE:
<223> OTHER INFORMATION: MBP_NjPAT_Fw Nucleotide sequence

<400> SEQUENCE: 8
caagatcatg tcgatcatca tcgc                                           24

<210> SEQ ID NO 9
<211> LENGTH: 33
<212> TYPE: DNA
<213> ORGANISM: Artificial Sequence
<220> FEATURE:
<223> OTHER INFORMATION: NjPAT_Rv Nucleotide sequence

<400> SEQUENCE: 9
tttatgattt ggatcctcag atgctgacgg ggt                                 33

<210> SEQ ID NO 10
<211> LENGTH: 2886
<212> TYPE: DNA
<213> ORGANISM: Artificial Sequence
<220> FEATURE:
<223> OTHER INFORMATION: SPppa-MBP-NjPAT Nucleotide sequence

<400> SEQUENCE: 10

| | | |
|---|---|---|
| aaatttattt gctttgtgag cggataacaa ttattagatt caccggcgag ccagcaggaa | 60 |
| tttcactcta gatgacagga gggacatatg aagatcgagg aaggcaagct cgtgatctgg | 120 |
| atcaacggcg acaagggcta caacggcctg gccgaggtgg gcaagaagtt cgagaaggac | 180 |
| accggcatca aggtgacggt ggagcacccg acaagctcg aggagaagtt cccgcaggtg | 240 |
| gcggccacgg gcgacggccc ggacatcatc ttctgggccc atgaccgctt cggcggctac | 300 |
| gcccagtcgg gcctgctggc cgagatcacc ccggacaagg cgttccagga caagctctat | 360 |
| cccttcacgt gggacgccgt gcgctacaac ggcaagctga tcgcgtatcc catcgcggtg | 420 |
| gaggccctgt cgctcatcta taacaaggac ctgctcccga acccgcccaa gacctgggag | 480 |
| gagatccccg ccctcgacaa ggagctgaag gccaagggca agtcggcgct catgttcaac | 540 |
| ctgcaggagc cgtacttcac ctggcccctg atcgcggccg acggcggcta cgcgttcaag | 600 |
| tatgagaacg gcaagtatga catcaaggac gtgggcgtgg acaacgcggg cgccaaggcc | 660 |
| ggcctgacct tcctcgtgga cctgatcaag aacaagcaca tgaacgccga cacggactac | 720 |
| tcgatcgcgg aggccgcgtt caacaagggc gagaccgcca tgacgatcaa cggcccgtgg | 780 |
| gcgtggtcga acatcgacac ctcgaaggtg aactatggcg tgaccgtgct ccccacgttc | 840 |
| aagggccagc cctcgaagcc cttcgtgggc gtgctgtcgg cgggcatcaa cgccgcgtcg | 900 |
| ccgaacaagg agctcgcgaa ggagttcctg gagaactacc tgctcaccga cgagggcctg | 960 |
| gaggccgtga caaggacaa gcccctgggc gccgtggccc tgaagtcgta tgaggaagag | 1020 |
| ctggtgaagg acccgcgcat cgcggccacc atggagaacg cgcagaaggg cgagatcatg | 1080 |
| ccgaacatcc cccagatgtc ggccttctgg tatgcggtgc gcaccgccgt gatcaacgcg | 1140 |
| gcctcgggcc gccagaccgt ggacgaggcc ctcaaggacg cccagaccgg cgacgacgac | 1200 |
| gacaagatca tgtcgatcat catcgccacc aacagcaccg agcatcccat cttccgcccg | 1260 |
| ctcgccaact tcccgccgtc gctctgggc aacctgttca cctcgttcag catggacaac | 1320 |
| caggcgcgcg agatctacgc caaggagcac gagggcctca aggagaaggt ccggatgatg | 1380 |

-continued

```
ttcctggaca ccacgaacta caagatctcg gagaagatca acttcatcaa caccgtcgag    1440
cgcctgggcg tgagctatca cttcgagaag gagatcgagg agctgctcca tcagatgttc    1500
gacgcccact cgaagcatct ggacgacatc caggagttcg acctcttcac gctgggcatc    1560
tacttccgca tcctgcggca gcatggctat aagatctcgt gcgacgtctt caacaagctg    1620
aaggacagca acggcgagtt caaggacgag ctcaaggacg acgtcaacgg catgctgtcg    1680
ttctatgagg ccacccatgt cgcgcacccat ggcgagaaca tcctcgacga ggcgctgatc    1740
tacacgaagg cccagctgga gtcgatggcg gccgcctcgc tcagcccgtt cctggccaac    1800
caggtgaagc acgcgctcat gcaggccctg cataagggca tcccgcgcat cgaggcgcgg    1860
aactacatct cggtctatga ggaagacccg aacaagaacg acctgctcct gcgcttcagc    1920
aagatcgact tcaacctggt gcagatgatc cacaagcagg agctgtgcga caccttccgg    1980
tggtggaagg acctggagtt cgagtcgaag ctgtcgttcg cccgcaaccg ggtggtggag    2040
gcctacctct ggacgctgtc ggcgtactat gagccgaagt attcgagcgc ccgcatcatc    2100
ctcgtgaagc tgatggtcat catctcggtg accgacgaca cgtacgacgc ctatggcacc    2160
ctggacgagc tccagctgtt cacggacgcg atccagcgcc tcgacatgtc gagcatcaac    2220
cagctgcccg actacatgaa gaccatctat aaggcgctcc tggacctctt cgacgagatc    2280
gaggaccgcc tgtcgaagca cgagacggac catagctacc gggtggcgta tgccaagtac    2340
gtctataagg agatcgtgcg ctgctacgac atggagtata agtggttcaa caagaactac    2400
gtccccgcct tcgaggagta tatgcagaag gccctggtga cctcgggcaa ccggctcctg    2460
atcacgttca gcttcctggg catggacgag gtcgcgacca tccaggcctt cgagtgggtg    2520
aagtcgaacg ccaagatgat cgtgtcgtcg aacaaggtgc tccgcctgat cgacgacatc    2580
atgtcgcacg aggaagagga cgagcgcggc catgtggcca cgggcatcga gtgcttcgtg    2640
aaggagcacg gcctgacccc gcgaggaagtg atcgtcgagt tccataagcg gatcgacgac    2700
gcgtggaagg acatcaacga ggagttcatc accccgaaca acctgccgat cgagatcctg    2760
acccgcgtgc tcaacctgac ccggatcggc gacgtggtct acaagtatga cgacggctac    2820
acgcaccccg agaaggccct caaggaccat atcatcagcc tgttcgtgga ccccgtcagc    2880
atctga                                                                2886
```

<210> SEQ ID NO 11
<211> LENGTH: 932
<212> TYPE: PRT
<213> ORGANISM: Artificial Sequence
<220> FEATURE:
<223> OTHER INFORMATION: MBP-NjPAT Aminoacid sequence

<400> SEQUENCE: 11

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
```

```
            85                  90                  95
Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
            130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
            165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
            210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
            245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
            290                 295                 300

Leu Lys Ser Tyr Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
            325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Gly
            355                 360                 365

Asp Asp Asp Asp Lys Ile Met Ser Ile Ile Ala Thr Asn Ser Thr
            370                 375                 380

Glu His Pro Ile Phe Arg Pro Leu Ala Asn Phe Pro Pro Ser Leu Trp
385                 390                 395                 400

Gly Asn Leu Phe Thr Ser Phe Ser Met Asp Asn Gln Ala Arg Glu Ile
            405                 410                 415

Tyr Ala Lys Glu His Glu Gly Leu Lys Glu Lys Val Arg Met Met Phe
            420                 425                 430

Leu Asp Thr Thr Asn Tyr Lys Ile Ser Glu Lys Ile Asn Phe Ile Asn
            435                 440                 445

Thr Val Glu Arg Leu Gly Val Ser Tyr His Phe Glu Lys Glu Ile Glu
            450                 455                 460

Glu Leu Leu His Gln Met Phe Asp Ala His Ser Lys His Leu Asp Asp
465                 470                 475                 480

Ile Gln Glu Phe Asp Leu Phe Thr Leu Gly Ile Tyr Phe Arg Ile Leu
            485                 490                 495

Arg Gln His Gly Tyr Lys Ile Ser Cys Asp Val Phe Asn Lys Leu Lys
            500                 505                 510
```

```
Asp Ser Asn Gly Glu Phe Lys Asp Glu Leu Lys Asp Val Asn Gly
        515                 520                 525

Met Leu Ser Phe Tyr Glu Ala Thr His Val Arg Thr His Gly Glu Asn
        530                 535                 540

Ile Leu Asp Glu Ala Leu Ile Tyr Thr Lys Ala Gln Leu Glu Ser Met
545                 550                 555                 560

Ala Ala Ala Ser Leu Ser Pro Phe Leu Ala Asn Gln Val Lys His Ala
                565                 570                 575

Leu Met Gln Ala Leu His Lys Gly Ile Pro Arg Ile Glu Ala Arg Asn
            580                 585                 590

Tyr Ile Ser Val Tyr Glu Glu Asp Pro Asn Lys Asn Asp Leu Leu Leu
        595                 600                 605

Arg Phe Ser Lys Ile Asp Phe Asn Leu Val Gln Met Ile His Lys Gln
        610                 615                 620

Glu Leu Cys Asp Thr Phe Arg Trp Trp Lys Asp Leu Glu Phe Glu Ser
625                 630                 635                 640

Lys Leu Ser Phe Ala Arg Asn Arg Val Val Glu Ala Tyr Leu Trp Thr
                645                 650                 655

Leu Ser Ala Tyr Tyr Glu Pro Lys Tyr Ser Ser Ala Arg Ile Ile Leu
            660                 665                 670

Val Lys Leu Met Val Ile Ile Ser Val Thr Asp Asp Thr Tyr Asp Ala
        675                 680                 685

Tyr Gly Thr Leu Asp Glu Leu Gln Leu Phe Thr Asp Ala Ile Gln Arg
690                 695                 700

Leu Asp Met Ser Ser Ile Asn Gln Leu Pro Asp Tyr Met Lys Thr Ile
705                 710                 715                 720

Tyr Lys Ala Leu Leu Asp Leu Phe Asp Glu Ile Glu Asp Arg Leu Ser
                725                 730                 735

Lys His Glu Thr Asp His Ser Tyr Arg Val Ala Tyr Ala Lys Tyr Val
            740                 745                 750

Tyr Lys Glu Ile Val Arg Cys Tyr Asp Met Glu Tyr Lys Trp Phe Asn
        755                 760                 765

Lys Asn Tyr Val Pro Ala Phe Glu Glu Tyr Met Gln Lys Ala Leu Val
        770                 775                 780

Thr Ser Gly Asn Arg Leu Leu Ile Thr Phe Ser Phe Leu Gly Met Asp
785                 790                 795                 800

Glu Val Ala Thr Ile Gln Ala Phe Glu Trp Val Lys Ser Asn Ala Lys
                805                 810                 815

Met Ile Val Ser Ser Asn Lys Val Leu Arg Leu Ile Asp Asp Ile Met
            820                 825                 830

Ser His Glu Glu Glu Asp Glu Arg Gly His Val Ala Thr Gly Ile Glu
        835                 840                 845

Cys Phe Val Lys Glu His Gly Leu Thr Arg Glu Glu Val Ile Val Glu
        850                 855                 860

Phe His Lys Arg Ile Asp Asp Ala Trp Lys Asp Ile Asn Glu Glu Phe
865                 870                 875                 880

Ile Thr Pro Asn Asn Leu Pro Ile Glu Ile Leu Thr Arg Val Leu Asn
                885                 890                 895

Leu Thr Arg Ile Gly Asp Val Val Tyr Lys Tyr Asp Asp Gly Tyr Thr
            900                 905                 910

His Pro Glu Lys Ala Leu Lys Asp His Ile Ile Ser Leu Phe Val Asp
        915                 920                 925
```

Pro Val Ser Ile
    930

<210> SEQ ID NO 12
<211> LENGTH: 25
<212> TYPE: DNA
<213> ORGANISM: Artificial Sequence
<220> FEATURE:
<223> OTHER INFORMATION: Fh8_NjPAT_Rv Nucleotide sequence

<400> SEQUENCE: 12
gatcgacatc gacgagagga tcgag                                    25

<210> SEQ ID NO 13
<211> LENGTH: 25
<212> TYPE: DNA
<213> ORGANISM: Artificial Sequence
<220> FEATURE:
<223> OTHER INFORMATION: Fh8_NjPAT_Fw Nucleotide sequence

<400> SEQUENCE: 13
ctcgtcgatg tcgatcatca tcgcc                                    25

<210> SEQ ID NO 14
<211> LENGTH: 1971
<212> TYPE: DNA
<213> ORGANISM: Artificial Sequence
<220> FEATURE:
<223> OTHER INFORMATION: SPppa- Fh8-NjPAT Nucleotide sequence

<400> SEQUENCE: 14
aaatttattt gctttgtgag cggataacaa ttattagatt caccggcgag ccagcaggaa     60
tttcactcta gatgacagga gggacatatg ccctcggtgc aagaggtgga gaagctgctg    120
catgtgctgg accggaacgg cgacggcaag gtgtcggcgg aggagctgaa ggcgttcgcc    180
gacgactcga agtgcccgct ggactcgaac aagatcaagg cgttcatcaa ggagcatgac    240
aagaacaagg acggcaagct ggacctcaag gagctggtct cgatcctctc gtcgatgtcg    300
atcatcatcg ccaccaacag caccgagcat cccatcttcc gcccgctcgc caacttcccg    360
ccgtcgctct ggggcaacct gttcacctcg ttcagcatgg acaaccaggc gcgcgagatc    420
tacgccaagg agcacgaggg cctcaaggag aaggtccgga tgatgttcct ggacaccacg    480
aactacaaga tctcggagaa gatcaacttc atcaacaccg tcgagcgcct gggcgtgagc    540
tatcacttcg agaaggagat cgaggagctg ctccatcaga tgttcgacgc ccactcgaag    600
catctggacg acatccagga gttcgacctc ttcacgctgg gcatctactt ccgcatcctg    660
cggcagcatg gctataagat ctcgtgcgac gtcttcaaca agctgaagga cagcaacggc    720
gagttcaagg acgagctcaa ggacgacgtc aacggcatgc tgtcgttcta tgaggccacc    780
catgtgcgca cccatggcga gaacatcctc gacgaggcgc tgatctacac gaaggcccag    840
ctggagtcga tggcggccgc ctcgctcagc ccgttcctgg ccaaccaggt gaagcacgcg    900
ctcatgcagg ccctgcataa gggcatcccg cgcatcgagg cgcggaacta catctcggtc    960
tatgaggaag acccgaacaa gaacgacctg ctcctgcgct tcagcaagat cgacttcaac   1020
ctggtgcaga tgatccacaa gcaggagctg tgcgacacct tccggtggtg aaggacctg    1080 gagttcgagt cgaagctgtc gttcgcccgc aaccgggtgg tggaggccta cctctggacg   1140
ctgtcggcgt actatgagcc gaagtattcg agcgcccgca tcatcctcgt gaagctgatg   1200
gtcatcatct cggtgaccga cgacacgtac gacgcctatg cacccctgga cgagctccag   1260

-continued

```
ctgttcacgg acgcgatcca gcgcctcgac atgtcgagca tcaaccagct gcccgactac    1320
atgaagacca tctataaggc gctcctggac ctcttcgacg agatcgagga ccgcctgtcg    1380
aagcacgaga cggaccatag ctaccgggtg gcgtatgcca agtacgtcta taaggagatc    1440
gtgcgctgct acgacatgga gtataagtgg ttcaacaaga actacgtccc cgccttcgag    1500
gagtatatgc agaaggccct ggtgacctcg ggcaaccggc tcctgatcac gttcagcttc    1560
ctgggcatgg acgaggtcgc gaccatccag gccttcgagt gggtgaagtc gaacgccaag    1620
atgatcgtgt cgtcgaacaa ggtgctccgc ctgatcgacg acatcatgtc gcacgaggaa    1680
gaggacgagc gcggccatgt ggccacgggc atcgagtgct cgtgaaagga gcacggcctg    1740
acccgcgagg aagtgatcgt cgagttccat aagcggatcg acgacgcgtg gaaggacatc    1800
aacgaggagt tcatcacccc gaacaacctg ccgatcgaga tcctgacccg cgtgctcaac    1860
ctgacccgga tcggcgacgt ggtctacaag tatgacgacg gctacacgca ccccgagaag    1920
gccctcaagg accatatcat cagcctgttc gtggaccccg tcagcatctg a             1971
```

<210> SEQ ID NO 15
<211> LENGTH: 627
<212> TYPE: PRT
<213> ORGANISM: Artificial Sequence
<220> FEATURE:
<223> OTHER INFORMATION: Fh8-NjPAT Aminoacid sequence

<400> SEQUENCE: 15

```
Met Pro Ser Val Gln Glu Val Glu Lys Leu Leu His Val Leu Asp Arg
1               5                   10                  15

Asn Gly Asp Gly Lys Val Ser Ala Glu Glu Leu Lys Ala Phe Ala Asp
            20                  25                  30

Asp Ser Lys Cys Pro Leu Asp Ser Asn Lys Ile Lys Ala Phe Ile Lys
        35                  40                  45

Glu His Asp Lys Asn Lys Asp Gly Lys Leu Asp Leu Lys Glu Leu Val
    50                  55                  60

Ser Ile Leu Ser Ser Met Ser Ile Ile Ile Ala Thr Asn Ser Thr Glu
65                  70                  75                  80

His Pro Ile Phe Arg Pro Leu Ala Asn Phe Pro Pro Ser Leu Trp Gly
                85                  90                  95

Asn Leu Phe Thr Ser Phe Ser Met Asp Asn Gln Ala Arg Glu Ile Tyr
            100                 105                 110

Ala Lys Glu His Glu Gly Leu Lys Glu Lys Val Arg Met Met Phe Leu
        115                 120                 125

Asp Thr Thr Asn Tyr Lys Ile Ser Glu Lys Ile Asn Phe Ile Asn Thr
    130                 135                 140

Val Glu Arg Leu Gly Val Ser Tyr His Phe Glu Lys Glu Ile Glu Glu
145                 150                 155                 160

Leu Leu His Gln Met Phe Asp Ala His Ser Lys His Leu Asp Asp Ile
                165                 170                 175

Gln Glu Phe Asp Leu Phe Thr Leu Gly Ile Tyr Phe Arg Ile Leu Arg
            180                 185                 190

Gln His Gly Tyr Lys Ile Ser Cys Asp Val Phe Asn Lys Leu Lys Asp
        195                 200                 205

Ser Asn Gly Glu Phe Lys Asp Glu Leu Lys Asp Asp Val Asn Gly Met
    210                 215                 220

Leu Ser Phe Tyr Glu Ala Thr His Val Arg Thr His Gly Glu Asn Ile
225                 230                 235                 240
```

-continued

Leu Asp Glu Ala Leu Ile Tyr Thr Lys Ala Gln Leu Glu Ser Met Ala
            245                 250                 255

Ala Ala Ser Leu Ser Pro Phe Leu Ala Asn Gln Val Lys His Ala Leu
        260                 265                 270

Met Gln Ala Leu His Lys Gly Ile Pro Arg Ile Glu Ala Arg Asn Tyr
    275                 280                 285

Ile Ser Val Tyr Glu Glu Asp Pro Asn Lys Asn Asp Leu Leu Leu Arg
290                 295                 300

Phe Ser Lys Ile Asp Phe Asn Leu Val Gln Met Ile His Lys Gln Glu
305                 310                 315                 320

Leu Cys Asp Thr Phe Arg Trp Trp Lys Asp Leu Glu Phe Glu Ser Lys
                325                 330                 335

Leu Ser Phe Ala Arg Asn Arg Val Val Glu Ala Tyr Leu Trp Thr Leu
            340                 345                 350

Ser Ala Tyr Tyr Glu Pro Lys Tyr Ser Ser Ala Arg Ile Ile Leu Val
        355                 360                 365

Lys Leu Met Val Ile Ile Ser Val Thr Asp Asp Thr Tyr Asp Ala Tyr
    370                 375                 380

Gly Thr Leu Asp Glu Leu Gln Leu Phe Thr Asp Ala Ile Gln Arg Leu
385                 390                 395                 400

Asp Met Ser Ser Ile Asn Gln Leu Pro Asp Tyr Met Lys Thr Ile Tyr
                405                 410                 415

Lys Ala Leu Leu Asp Leu Phe Asp Glu Ile Glu Asp Arg Leu Ser Lys
            420                 425                 430

His Glu Thr Asp His Ser Tyr Arg Val Ala Tyr Ala Lys Tyr Val Tyr
        435                 440                 445

Lys Glu Ile Val Arg Cys Tyr Asp Met Glu Tyr Lys Trp Phe Asn Lys
    450                 455                 460

Asn Tyr Val Pro Ala Phe Glu Glu Tyr Met Gln Lys Ala Leu Val Thr
465                 470                 475                 480

Ser Gly Asn Arg Leu Leu Ile Thr Phe Ser Phe Leu Gly Met Asp Glu
                485                 490                 495

Val Ala Thr Ile Gln Ala Phe Glu Trp Val Lys Ser Asn Ala Lys Met
            500                 505                 510

Ile Val Ser Ser Asn Lys Val Leu Arg Leu Ile Asp Asp Ile Met Ser
        515                 520                 525

His Glu Glu Asp Glu Arg Gly His Val Ala Thr Gly Ile Glu Cys
    530                 535                 540

Phe Val Lys Glu His Gly Leu Thr Arg Glu Val Ile Val Glu Phe
545                 550                 555                 560

His Lys Arg Ile Asp Asp Ala Trp Lys Asp Ile Asn Glu Glu Phe Ile
                565                 570                 575

Thr Pro Asn Asn Leu Pro Ile Glu Ile Leu Thr Arg Val Leu Asn Leu
            580                 585                 590

Thr Arg Ile Gly Asp Val Val Tyr Lys Tyr Asp Gly Tyr Thr His
        595                 600                 605

Pro Glu Lys Ala Leu Lys Asp His Ile Ile Ser Leu Phe Val Asp Pro
    610                 615                 620

Val Ser Ile
625

<210> SEQ ID NO 16
<211> LENGTH: 24
<212> TYPE: DNA

```
<213> ORGANISM: Artificial Sequence
<220> FEATURE:
<223> OTHER INFORMATION: SUMO_NjPAT_Rv Nucleotide sequence

<400> SEQUENCE: 16
gatcgacatg ccgatctgct cgcg                                            24

<210> SEQ ID NO 17
<211> LENGTH: 25
<212> TYPE: DNA
<213> ORGANISM: Artificial Sequence
<220> FEATURE:
<223> OTHER INFORMATION: SUMO_NjPAT_Fw Nucleotide sequence

<400> SEQUENCE: 17
gatcggcatg tcgatcatca tcgcc                                           25

<210> SEQ ID NO 18
<211> LENGTH: 2055
<212> TYPE: DNA
<213> ORGANISM: Artificial Sequence
<220> FEATURE:
<223> OTHER INFORMATION: SPppa-SUMO-NjPAT Nucleotide sequence

<400> SEQUENCE: 18
aaatttattt gctttgtgag cggataacaa ttattagatt caccggcgag ccagcaggaa      60
tttcactcta gatgacagga gggacatatg tcggacagcg aggtgaacca ggaagccaag     120
cccgaggtga agcccgaggt gaagccggag acccacatca acctgaaggt gtcggacggc     180
tcgtcggaga tcttcttcaa gatcaagaag accacgcccc tgcgccgcct catggaggcc     240
ttcgccaagc gccagggcaa ggagatggac tcgctgcgct tcctctacga cggcatccgc     300
atccaggcgg accagacgcc ggaggacctc gacatggagg acaacgacat catcgaggcg     360
catcgcgagc agatcggcat gtcgatcatc atcgccacca acagcaccga gcatcccatc     420
ttccgcccgc tcgccaactt cccgccgtcg ctctggggca acctgttcac ctcgttcagc     480
atggacaacc aggcgcgcga gatctacgcc aaggagcacg agggcctcaa ggagaaggtc     540
cggatgatgt tcctggacac cacgaactac aagatctcgg agaagatcaa cttcatcaac     600
accgtcgagc gcctgggcgt gagctatcac ttcgagaagg agatcgagga gctgctccat     660
cagatgttcg acgcccactc gaagcatctg gacgacatcc aggagttcga cctcttcacg     720
ctgggcatct acttccgcat cctgcggcag catggctata gatctcgtg cgacgtcttc      780 aacaagctga aggacagcaa cggcgagttc aaggacgagc tcaaggacga cgtcaacggc     840
atgctgtcgt tctatgaggc cacccatgtg cgcacccatg gcgagaacat cctcgacgag     900
gcgctgatct acacgaaggc ccagctggag tcgatggcgg ccgcctcgct cagcccgttc     960
ctggccaacc aggtgaagca cgcgctcatg caggccctgc ataagggcat cccgcgcatc    1020
gaggcgcgga actacatctc ggtctatgag gaagacccga caagaacga cctgctcctg    1080 cgcttcagca agatcgactt caacctggtg cagatgatcc acaagcagga gctgtgcgac    1140
accttccggt ggtggaagga cctggagttc gagtcgaagc tgtcgttcgc ccgcaaccgg    1200
gtggtggagg cctacctctg gacgctgtcg gcgtactatg agccgaagta ttcgagcgcc    1260
cgcatcatcc tcgtgaagct gatggtcatc atctcggtga ccgacgacac gtacgacgcc    1320
tatggcaccc tggacgagct ccagctgttc acgacgcga tccagcgcct cgacatgtcg    1380
agcatcaacc agctgcccga ctacatgaag accatctata ggcgctcct ggacctcttc    1440 gacgagatcg aggaccgcct gtcgaagcac gagacggacc atagctaccg ggtggcgtat    1500
```

-continued

```
gccaagtacg tctataagga gatcgtgcgc tgctacgaca tggagtataa gtggttcaac    1560
aagaactacg tccccgcctt cgaggagtat atgcagaagg ccctggtgac ctcgggcaac    1620
cggctcctga tcacgttcag cttcctgggc atggacgagg tcgcgaccat ccaggccttc    1680
gagtgggtga agtcgaacgc caagatgatc gtgtcgtcga acaaggtgct ccgcctgatc    1740
gacgacatca tgtcgcacga ggaagaggac gagcgcggcc atgtggccac gggcatcgag    1800
tgcttcgtga aggagcacgg cctgacccgc gaggaagtga tcgtcgagtt ccataagcgg    1860
atcgacgacg cgtggaagga catcaacgag gagttcatca ccccgaacaa cctgccgatc    1920
gagatcctga cccgcgtgct caacctgacc cggatcggcg acgtggtcta caagtatgac    1980
gacggctaca cgcaccccga gaaggccctc aaggaccata tcatcagcct gttcgtggac    2040
cccgtcagca tctga                                                    2055
```

<210> SEQ ID NO 19
<211> LENGTH: 655
<212> TYPE: PRT
<213> ORGANISM: Artificial Sequence
<220> FEATURE:
<223> OTHER INFORMATION: SUMO-NjPAT Aminoacid sequence

<400> SEQUENCE: 19

```
Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30

Ser Glu Ile Phe Phe Lys Ile Lys Lys Thr Thr Pro Leu Arg Arg Leu
        35                  40                  45

Met Glu Ala Phe Ala Lys Arg Gln Gly Lys Glu Met Asp Ser Leu Arg
    50                  55                  60

Phe Leu Tyr Asp Gly Ile Arg Ile Gln Ala Asp Gln Thr Pro Glu Asp
65                  70                  75                  80

Leu Asp Met Glu Asp Asn Asp Ile Ile Glu Ala His Arg Glu Gln Ile
                85                  90                  95

Gly Met Ser Ile Ile Ile Ala Thr Asn Ser Thr Glu His Pro Ile Phe
            100                 105                 110

Arg Pro Leu Ala Asn Phe Pro Pro Ser Leu Trp Gly Asn Leu Phe Thr
        115                 120                 125

Ser Phe Ser Met Asp Asn Gln Ala Arg Glu Ile Tyr Ala Lys Glu His
    130                 135                 140

Glu Gly Leu Lys Glu Lys Val Arg Met Met Phe Leu Asp Thr Thr Asn
145                 150                 155                 160

Tyr Lys Ile Ser Glu Lys Ile Asn Phe Ile Asn Thr Val Glu Arg Leu
                165                 170                 175

Gly Val Ser Tyr His Phe Glu Lys Glu Ile Glu Glu Leu Leu His Gln
            180                 185                 190

Met Phe Asp Ala His Ser Lys His Leu Asp Asp Ile Gln Glu Phe Asp
        195                 200                 205

Leu Phe Thr Leu Gly Ile Tyr Phe Arg Ile Leu Arg Gln His Gly Tyr
    210                 215                 220

Lys Ile Ser Cys Asp Val Phe Asn Lys Leu Lys Asp Ser Asn Gly Glu
225                 230                 235                 240

Phe Lys Asp Glu Leu Lys Asp Asp Val Asn Gly Met Leu Ser Phe Tyr
                245                 250                 255
```

Glu Ala Thr His Val Arg Thr His Gly Glu Asn Ile Leu Asp Glu Ala
                260                 265                 270

Leu Ile Tyr Thr Lys Ala Gln Leu Glu Ser Met Ala Ala Ala Ser Leu
            275                 280                 285

Ser Pro Phe Leu Ala Asn Gln Val Lys His Ala Leu Met Gln Ala Leu
        290                 295                 300

His Lys Gly Ile Pro Arg Ile Glu Ala Arg Asn Tyr Ile Ser Val Tyr
305                 310                 315                 320

Glu Glu Asp Pro Asn Lys Asn Asp Leu Leu Arg Phe Ser Lys Ile
                325                 330                 335

Asp Phe Asn Leu Val Gln Met Ile His Lys Gln Glu Leu Cys Asp Thr
            340                 345                 350

Phe Arg Trp Trp Lys Asp Leu Glu Phe Glu Ser Lys Leu Ser Phe Ala
        355                 360                 365

Arg Asn Arg Val Val Glu Ala Tyr Leu Trp Thr Leu Ser Ala Tyr Tyr
    370                 375                 380

Glu Pro Lys Tyr Ser Ser Ala Arg Ile Ile Leu Val Lys Leu Met Val
385                 390                 395                 400

Ile Ile Ser Val Thr Asp Asp Thr Tyr Asp Ala Tyr Gly Thr Leu Asp
            405                 410                 415

Glu Leu Gln Leu Phe Thr Asp Ala Ile Gln Arg Leu Asp Met Ser Ser
        420                 425                 430

Ile Asn Gln Leu Pro Asp Tyr Met Lys Thr Ile Tyr Lys Ala Leu Leu
    435                 440                 445

Asp Leu Phe Asp Glu Ile Glu Asp Arg Leu Ser Lys His Glu Thr Asp
450                 455                 460

His Ser Tyr Arg Val Ala Tyr Ala Lys Tyr Val Tyr Lys Glu Ile Val
465                 470                 475                 480

Arg Cys Tyr Asp Met Glu Tyr Lys Trp Phe Asn Lys Asn Tyr Val Pro
            485                 490                 495

Ala Phe Glu Glu Tyr Met Gln Lys Ala Leu Val Thr Ser Gly Asn Arg
        500                 505                 510

Leu Leu Ile Thr Phe Ser Phe Leu Gly Met Asp Glu Val Ala Thr Ile
    515                 520                 525

Gln Ala Phe Glu Trp Val Lys Ser Asn Ala Lys Met Ile Val Ser Ser
530                 535                 540

Asn Lys Val Leu Arg Leu Ile Asp Asp Ile Met Ser His Glu Glu Glu
545                 550                 555                 560

Asp Glu Arg Gly His Val Ala Thr Gly Ile Glu Cys Phe Val Lys Glu
            565                 570                 575

His Gly Leu Thr Arg Glu Glu Val Ile Val Glu Phe His Lys Arg Ile
        580                 585                 590

Asp Asp Ala Trp Lys Asp Ile Asn Glu Glu Phe Ile Thr Pro Asn Asn
    595                 600                 605

Leu Pro Ile Glu Ile Leu Thr Arg Val Leu Asn Leu Thr Arg Ile Gly
610                 615                 620

Asp Val Val Tyr Lys Tyr Asp Asp Gly Tyr Thr His Pro Glu Lys Ala
625                 630                 635                 640

Leu Lys Asp His Ile Ile Ser Leu Phe Val Asp Pro Val Ser Ile
            645                 650                 655

<210> SEQ ID NO 20
<211> LENGTH: 26
<212> TYPE: DNA

<213> ORGANISM: Artificial Sequence
<220> FEATURE:
<223> OTHER INFORMATION: NusA_NjPAT_Rv Nucleotide sequence

<400> SEQUENCE: 20

| tgatcgacat cgcctcgtcg ccgaac | 26 |

<210> SEQ ID NO 21
<211> LENGTH: 25
<212> TYPE: DNA
<213> ORGANISM: Artificial Sequence
<220> FEATURE:
<223> OTHER INFORMATION: NusA_NjPAT_Fw Nucleotide sequence

<400> SEQUENCE: 21

| cgaggcgatg tcgatcatca tcgcc | 25 |

<210> SEQ ID NO 22
<211> LENGTH: 3249
<212> TYPE: DNA
<213> ORGANISM: Artificial Sequence
<220> FEATURE:
<223> OTHER INFORMATION: SPppa-NusA-NjPAT Nucleotide sequence

<400> SEQUENCE: 22

| aaatttattt gctttgtgag cggataacaa ttattagatt caccggcgag ccagcaggaa | 60 |
| tttcactcta gatgacagga gggacatatg aacaaggaga tcctcgcggt ggtggaggcg | 120 |
| gtgtcgaacg agaaggcgct gccccgcgag aagatcttcg aggccctgga gtcggccctg | 180 |
| gccaccgcga ccaagaagaa gtacgagcag gagatcgacg tgcgcgtgca gatcgaccgc | 240 |
| aagtcgggcg acttcgacac gttccgccgc tggctcgtgg tggacgaggt gacccagccc | 300 |
| acgaaggaga tcaccctgga ggcggcccgc tatgaggacg agtcgctgaa cctcggcgac | 360 |
| tatgtggagg accagatcga gtcggtgacc ttcgaccgca tcaccacgca gacggcgaag | 420 |
| caggtgatcg tgcagaaggt gcgcgaggcc gagcgcgcca tggtggtgga ccagttccgc | 480 |
| gagcacgagg gcgagatcat caccggcgtg gtgaagaagg tgaaccgcga caacatctcg | 540 |
| ctggacctgg gcaacaacgc ggaggccgtg atcctgcgcg aggacatgct cccgcgcgag | 600 |
| aacttccgcc cgggcgaccg cgtgcgcggc gtgctctatt cggtgcgccc cgaggcccgt | 660 |
| ggcgcccagc tgttcgtgac ccgctcgaag ccggagatgc tgatcgagct cttccgcatc | 720 |
| gaggtgcccg agatcggcga ggaagtgatc gagatcaagg cggccgcccg cgacccgggc | 780 |
| tcgcgcgcga agatcgccgt gaagaccaac gacaagcgca tcgacccccgt ggggcgcctgc | 840 |
| gtgggcatgc gtggcgcccg cgtgcaggcc gtgtcgaccg agctcggcgg cgagcgcatc | 900 |
| gacatcgtgc tgtgggacga caacccggcg cagttcgtga tcaacgccat ggcccccggcg | 960 |
| gacgtggcct cgatcgtggt ggacgaggac aagcatacca tggacatcgc cgtggaggcg | 1020 |
| ggcaacctgg cccaggccat cggccgcaac ggccagaacg tgcgcctggc ctcgcagctc | 1080 |
| tcgggctggg agctgaacgt gatgacggtg gacgacctgc aggccaagca tcaggccgag | 1140 |
| gcccatgccg ccatcgacac cttcacgaag tacctcgaca tcgacgagga cttcgcgacc | 1200 |
| gtgctcgtgg aggaaggctt ctcgacgctg gaggagctcg cctatgtgcc gatgaaggag | 1260 |
| ctgctcgaga tcgagggcct ggacgagccg acggtggagg cgctccgcga gcgcgccaag | 1320 |
| aacgccctgg ccaccatcgc ccaggcccag gaagagtcgc tgggcgacaa caagccggcc | 1380 |
| gacgacctgc tcaacctgga gggcgtggac cgcgacctgg ccttcaagct cgccgcccgc | 1440 |
| ggcgtgtgca cgctcgagga cctggccgag cagggcatcg acgacctggc cgacatcgag | 1500 |

-continued

```
ggcctcaccg acgagaaggc cggcgccctg atcatggccg cccgcaacat ctgctggttc    1560
ggcgacgagg cgatgtcgat catcatcgcc accaacagca ccgagcatcc catcttccgc    1620
ccgctcgcca acttcccgcc gtcgctctgg ggcaacctgt tcacctcgtt cagcatggac    1680
aaccaggcgc gcgagatcta cgccaaggag cacgagggcc tcaaggagaa ggtccggatg    1740
atgttcctgg acaccacgaa ctacaagatc tcggagaaga tcaacttcat caacaccgtc    1800
gagcgcctgg gcgtgagcta tcacttcgag aaggagatcg aggagctgct ccatcagatg    1860
ttcgacgccc actcgaagca tctggacgac atccaggagt cgacctcttc acgctgggc    1920 atctacttcc gcatcctgcg gcagcatggc tataagatct cgtgcgacgt cttcaacaag    1980
ctgaaggaca gcaacggcga gttcaaggac gagctcaagg acgacgtcaa cggcatgctg    2040
tcgttctatg aggccaccca tgtgcgcacc catggcgaga catcctcga cgaggcgctg    2100 atctacacga aggcccagct ggagtcgatg gcggccgcct cgctcagccc gttcctggcc    2160
aaccaggtga gcacgcgct catgcaggcc ctgcataagg gcatcccgcg catcgaggcg    2220
cggaactaca tctcggtcta tgaggaagac ccgaacaaga cgacctgct cctgcgcttc    2280 agcaagatcg acttcaacct ggtgcagatg atccacaagc aggagctgtg cgacaccttc    2340
cggtggtgga aggacctgga gttcgagtcg aagctgtcgt tcgcccgcaa ccgggtggtg    2400
gaggcctacc tctggacgct gtcggcgtac tatgagccga agtattcgag cgcccgcatc    2460
atcctcgtga agctgatggt catcatctcg gtgaccgacg acacgtacga cgcctatggc    2520
accctggacg agtccagct gttcacggac gcgatccagc gcctcgacat gtcgagcatc    2580
aaccagctgc ccgactacat gaagaccatc tataaggcgc tcctggaccct cttcgacgag    2640 atcgaggacc gcctgtcgaa gcacgagacg gaccatagct accgggtggc gtatgccaag    2700
tacgtctata aggagatcgt gcgctgctac gacatggagt ataagtggtt caacaagaac    2760
tacgtccccg ccttcgagga gtatatgcag aaggccctgg tgacctcggg caaccggctc    2820
ctgatcacgt tcagcttcct gggcatggac gaggtcgcga ccatccaggc cttcgagtgg    2880
gtgaagtcga acgccaagat gatcgtgtcg tcgaacaagg tgctccgcct gatcgacgac    2940
atcatgtcgc acgaggaaga ggacgagcgc ggccatgtgg ccacgggcat cgagtgcttc    3000
gtgaaggagc acggcctgac ccgcgaggaa gtgatcgtcg agttccataa gcggatcgac    3060
gacgcgtgga aggacatcaa cgaggagttc atcaccccga caacctgcc gatcgagatc    3120 ctgacccgcg tgctcaacct gacccggatc ggcgacgtgg tctacaagta tgacgacggc    3180
tacacgcacc ccgagaaggc cctcaaggac catatcatca gcctgttcgt ggaccccgtc    3240
agcatctga                                                           3249
```

<210> SEQ ID NO 23
<211> LENGTH: 1053
<212> TYPE: PRT
<213> ORGANISM: Artificial Sequence
<220> FEATURE:
<223> OTHER INFORMATION: NusA-NjPAT Aminoacid sequence

<400> SEQUENCE: 23

```
Met Asn Lys Glu Ile Leu Ala Val Val Glu Ala Val Ser Asn Glu Lys
1               5                   10                  15

Ala Leu Pro Arg Glu Lys Ile Phe Glu Ala Leu Glu Ser Ala Leu Ala
            20                  25                  30

Thr Ala Thr Lys Lys Lys Tyr Glu Gln Glu Ile Asp Val Arg Val Gln
        35                  40                  45
```

```
Ile Asp Arg Lys Ser Gly Asp Phe Asp Thr Phe Arg Arg Trp Leu Val
 50                  55                  60

Val Asp Glu Val Thr Gln Pro Thr Lys Glu Ile Thr Leu Glu Ala Ala
 65                  70                  75                  80

Arg Tyr Glu Asp Glu Ser Leu Asn Leu Gly Asp Tyr Val Glu Asp Gln
                     85                  90                  95

Ile Glu Ser Val Thr Phe Asp Arg Ile Thr Thr Gln Thr Ala Lys Gln
                100                 105                 110

Val Ile Val Gln Lys Val Arg Glu Ala Glu Arg Ala Met Val Val Asp
                115                 120                 125

Gln Phe Arg Glu His Glu Gly Glu Ile Ile Thr Gly Val Val Lys Lys
        130                 135                 140

Val Asn Arg Asp Asn Ile Ser Leu Asp Leu Gly Asn Asn Ala Glu Ala
145                 150                 155                 160

Val Ile Leu Arg Glu Asp Met Leu Pro Arg Glu Asn Phe Arg Pro Gly
                165                 170                 175

Asp Arg Val Arg Gly Val Leu Tyr Ser Val Arg Pro Glu Ala Arg Gly
                180                 185                 190

Ala Gln Leu Phe Val Thr Arg Ser Lys Pro Glu Met Leu Ile Glu Leu
        195                 200                 205

Phe Arg Ile Glu Val Pro Glu Ile Gly Glu Glu Val Ile Glu Ile Lys
        210                 215                 220

Ala Ala Ala Arg Asp Pro Gly Ser Arg Ala Lys Ile Ala Val Lys Thr
225                 230                 235                 240

Asn Asp Lys Arg Ile Asp Pro Val Gly Ala Cys Val Gly Met Arg Gly
                245                 250                 255

Ala Arg Val Gln Ala Val Ser Thr Glu Leu Gly Gly Glu Arg Ile Asp
                260                 265                 270

Ile Val Leu Trp Asp Asp Asn Pro Ala Gln Phe Val Ile Asn Ala Met
        275                 280                 285

Ala Pro Ala Asp Val Ala Ser Ile Val Val Asp Glu Asp Lys His Thr
290                 295                 300

Met Asp Ile Ala Val Glu Ala Gly Asn Leu Ala Gln Ala Ile Gly Arg
305                 310                 315                 320

Asn Gly Gln Asn Val Arg Leu Ala Ser Gln Leu Ser Gly Trp Glu Leu
                325                 330                 335

Asn Val Met Thr Val Asp Asp Leu Gln Ala Lys His Gln Ala Glu Ala
                340                 345                 350

His Ala Ala Ile Asp Thr Phe Thr Lys Tyr Leu Asp Ile Asp Glu Asp
        355                 360                 365

Phe Ala Thr Val Leu Val Glu Glu Gly Phe Ser Thr Leu Glu Glu Leu
370                 375                 380

Ala Tyr Val Pro Met Lys Glu Leu Leu Glu Ile Glu Gly Leu Asp Glu
385                 390                 395                 400

Pro Thr Val Glu Ala Leu Arg Glu Arg Ala Lys Asn Ala Leu Ala Thr
                405                 410                 415

Ile Ala Gln Ala Gln Glu Glu Ser Leu Gly Asp Asn Lys Pro Ala Asp
                420                 425                 430

Asp Leu Leu Asn Leu Glu Gly Val Asp Arg Asp Leu Ala Phe Lys Leu
        435                 440                 445

Ala Ala Arg Gly Val Cys Thr Leu Glu Asp Leu Ala Glu Gln Gly Ile
450                 455                 460
```

```
Asp Asp Leu Ala Asp Ile Glu Gly Leu Thr Asp Glu Lys Ala Gly Ala
465                 470                 475                 480

Leu Ile Met Ala Ala Arg Asn Ile Cys Trp Phe Gly Asp Glu Ala Met
                485                 490                 495

Ser Ile Ile Ile Ala Thr Asn Ser Thr Glu His Pro Ile Phe Arg Pro
                500                 505                 510

Leu Ala Asn Phe Pro Pro Ser Leu Trp Gly Asn Leu Phe Thr Ser Phe
                515                 520                 525

Ser Met Asp Asn Gln Ala Arg Glu Ile Tyr Ala Lys Glu His Glu Gly
            530                 535                 540

Leu Lys Glu Lys Val Arg Met Met Phe Leu Asp Thr Thr Asn Tyr Lys
545                 550                 555                 560

Ile Ser Glu Lys Ile Asn Phe Ile Asn Thr Val Glu Arg Leu Gly Val
                565                 570                 575

Ser Tyr His Phe Glu Lys Glu Ile Glu Glu Leu Leu His Gln Met Phe
                580                 585                 590

Asp Ala His Ser Lys His Leu Asp Asp Ile Gln Glu Phe Asp Leu Phe
            595                 600                 605

Thr Leu Gly Ile Tyr Phe Arg Ile Leu Arg Gln His Gly Tyr Lys Ile
    610                 615                 620

Ser Cys Asp Val Phe Asn Lys Leu Lys Asp Ser Asn Gly Glu Phe Lys
625                 630                 635                 640

Asp Glu Leu Lys Asp Asp Val Asn Gly Met Leu Ser Phe Tyr Glu Ala
                645                 650                 655

Thr His Val Arg Thr His Gly Glu Asn Ile Leu Asp Glu Ala Leu Ile
            660                 665                 670

Tyr Thr Lys Ala Gln Leu Glu Ser Met Ala Ala Ser Leu Ser Pro
    675                 680                 685

Phe Leu Ala Asn Gln Val Lys His Ala Leu Met Gln Ala Leu His Lys
690                 695                 700

Gly Ile Pro Arg Ile Glu Ala Arg Asn Tyr Ile Ser Val Tyr Glu Glu
705                 710                 715                 720

Asp Pro Asn Lys Asn Asp Leu Leu Arg Phe Ser Lys Ile Asp Phe
                725                 730                 735

Asn Leu Val Gln Met Ile His Lys Gln Glu Leu Cys Asp Thr Phe Arg
                740                 745                 750

Trp Trp Lys Asp Leu Glu Phe Glu Ser Lys Leu Ser Phe Ala Arg Asn
            755                 760                 765

Arg Val Val Glu Ala Tyr Leu Trp Thr Leu Ser Ala Tyr Tyr Glu Pro
    770                 775                 780

Lys Tyr Ser Ser Ala Arg Ile Ile Leu Val Lys Leu Met Val Ile Ile
785                 790                 795                 800

Ser Val Thr Asp Asp Thr Tyr Asp Ala Tyr Gly Thr Leu Asp Glu Leu
            805                 810                 815

Gln Leu Phe Thr Asp Ala Ile Gln Arg Leu Asp Met Ser Ser Ile Asn
            820                 825                 830

Gln Leu Pro Asp Tyr Met Lys Thr Ile Tyr Lys Ala Leu Leu Asp Leu
            835                 840                 845

Phe Asp Glu Ile Glu Asp Arg Leu Ser Lys His Glu Thr Asp His Ser
850                 855                 860

Tyr Arg Val Ala Tyr Ala Lys Tyr Val Tyr Lys Glu Ile Val Arg Cys
865                 870                 875                 880

Tyr Asp Met Glu Tyr Lys Trp Phe Asn Lys Asn Tyr Val Pro Ala Phe
```

```
                885                 890                 895
Glu Glu Tyr Met Gln Lys Ala Leu Val Thr Ser Gly Asn Arg Leu Leu
            900                 905                 910

Ile Thr Phe Ser Phe Leu Gly Met Asp Glu Val Ala Thr Ile Gln Ala
            915                 920                 925

Phe Glu Trp Val Lys Ser Asn Ala Lys Met Ile Val Ser Ser Asn Lys
            930                 935                 940

Val Leu Arg Leu Ile Asp Asp Ile Met Ser His Glu Glu Asp Glu
945                 950                 955                 960

Arg Gly His Val Ala Thr Gly Ile Glu Cys Phe Val Lys Glu His Gly
            965                 970                 975

Leu Thr Arg Glu Glu Val Ile Val Glu Phe His Lys Arg Ile Asp Asp
            980                 985                 990

Ala Trp Lys Asp Ile Asn Glu Glu Phe Ile Thr Pro Asn Asn Leu Pro
            995                1000                1005

Ile Glu Ile Leu Thr Arg Val Leu Asn Leu Thr Arg Ile Gly Asp
            1010                1015                1020

Val Val Tyr Lys Tyr Asp Asp Gly Tyr Thr His Pro Glu Lys Ala
            1025                1030                1035

Leu Lys Asp His Ile Ile Ser Leu Phe Val Asp Pro Val Ser Ile
            1040                1045                1050

<210> SEQ ID NO 24
<211> LENGTH: 26
<212> TYPE: DNA
<213> ORGANISM: Artificial Sequence
<220> FEATURE:
<223> OTHER INFORMATION: RsTRX_NjPAT_Rv Nucleotide sequence

<400> SEQUENCE: 24
tgatcgacat gagcgccgag gcgatc                                            26

<210> SEQ ID NO 25
<211> LENGTH: 25
<212> TYPE: DNA
<213> ORGANISM: Artificial Sequence
<220> FEATURE:
<223> OTHER INFORMATION: RsTRX_NjPAT_Fw Nucleotide sequence

<400> SEQUENCE: 25
ggcgctcatg tcgatcatca tcgcc                                             25

<210> SEQ ID NO 26
<211> LENGTH: 2082
<212> TYPE: DNA
<213> ORGANISM: Artificial Sequence
<220> FEATURE:
<223> OTHER INFORMATION: SPppa-RsTRX-NjPAT Nucleotide sequence

<400> SEQUENCE: 26
aaatttattt gctttgtgag cggataacaa ttattagatt caccggcgag ccagcaggaa        60
tttcactcta gatgacagga gggacatatg tccaccgttc ccgtgacgga cgccaccttc       120
gacaccgagg tgcgcaagtc cgacgtgccc gtcgtcgtcg atttctgggc cgaatggtgc       180 ggccctgcc ggcagatcgg cccggcgctc gaggagctct cgaaggaata tgccggcaag       240
gtgaagatcg tgaaggtcaa tgtcgacgag aaccccgaga gcccggcgat gctgggcgtt       300
cgcggcatcc cggcgctgtt cctgttcaag aacggtcagg tcgtgtcgaa caaggtcggc       360
gctgcgccga aggccgcgct ggccaccctgg atcgcctcgg cgctcatgtc gatcatcatc       420
```

-continued

```
gccaccaaca gcaccgagca tcccatcttc cgcccgctcg ccaacttccc gccgtcgctc    480
tggggcaacc tgttcaccct cgttcagcat gacaaccagg cgcgcgagat ctacgccaag    540
gagcacgagg gcctcaagga gaaggtccgg atgatgttcc tggacaccac gaactacaag    600
atctcggaga agatcaactt catcaacacc gtcgagcgcc tgggcgtgag ctatcacttc    660
gagaaggaga tcgaggagct gctccatcag atgttcgacg cccactcgaa gcatctggac    720
gacatccagg agttcgacct cttcacgctg ggcatctact tccgcatcct gcggcagcat    780
ggctataaga tctcgtgcga cgtcttcaac aagctgaagg acagcaacgg cgagttcaag    840
gacgagctca aggacgacgt caacggcatg ctgtcgttct atgaggccac ccatgtgcgc    900
acccatggcg agaacatcct cgacgaggcg ctgatctaca cgaaggccca gctggagtcg    960
atggcggccg cctcgctcag cccgttcctg gccaaccagg tgaagcacgc gctcatgcag   1020
gccctgcata agggcatccc gcgcatcgag gcgcggaact acatctcggt ctatgaggaa   1080
gacccgaaca gaacgacct gctcctgcgc ttcagcaaga tcgacttcaa cctggtgcag   1140
atgatccaca gcaggagct gtgcgacacc ttccggtggt ggaaggacct ggagttcgag   1200
tcgaagctgt cgttcgcccg caacggggtg gtggaggcct acctctggac gctgtcggcg   1260
tactatgagc cgaagtattc gagcgcccgc atcatcctcg tgaagctgat ggtcatcatc   1320
tcggtgaccg acgacacgta cgacgcctat ggcaccctgg acgagctcca gctgttcacg   1380
gacgcgatcc agcgcctcga catgtcgagc atcaaccagc tgcccgacta catgaagacc   1440
atctataagg cgctcctgga cctcttcgac gagatcgagg accgcctgtc gaagcacgag   1500
acggaccata gctaccgggt ggcgtatgcc aagtacgtct ataaggagat cgtgcgctgc   1560
tacgacatgg agtataagtg gttcaacaag aactacgtcc ccgccttcga ggagtatatg   1620
cagaaggccc tggtgacctc gggcaaccgg ctcctgatca cgttcagctt cctgggcatg   1680
gacgaggtcg cgaccatcca ggccttcgag tgggtgaagt cgaacgccaa gatgatcgtg   1740
tcgtcgaaca aggtgctccg cctgatcgac gacatcatgt cgcacgagga agaggacgag   1800
cgcggccatg tggccacggg catcgagtgc ttcgtgaagg agcacggcct gacccgcgag   1860
gaagtgatcg tcgagttcca taagcggatc gacgacgcgt ggaaggacat caacgaggag   1920
ttcatcaccc cgaacaacct gccgatcgag atcctgaccc gcgtgctcaa cctgacccgg   1980
atcggcgacg tggtctacaa gtatgacgac ggctacacgc accccgagaa ggccctcaag   2040
gaccatatca tcagcctgtt cgtggacccc gtcagcatct ga                      2082
```

<210> SEQ ID NO 27
<211> LENGTH: 664
<212> TYPE: PRT
<213> ORGANISM: Artificial Sequence
<220> FEATURE:
<223> OTHER INFORMATION: RsTRX-NjPAT Aminoacid sequence

<400> SEQUENCE: 27

```
Met Ser Thr Val Pro Val Thr Asp Ala Thr Phe Asp Thr Glu Val Arg
1               5                   10                  15

Lys Ser Asp Val Pro Val Val Asp Phe Trp Ala Glu Trp Cys Gly
            20                  25                  30

Pro Cys Arg Gln Ile Gly Pro Ala Leu Glu Glu Leu Ser Lys Glu Tyr
        35                  40                  45

Ala Gly Lys Val Lys Ile Val Lys Val Asn Val Asp Glu Asn Pro Glu
    50                  55                  60
```

```
Ser Pro Ala Met Leu Gly Val Arg Gly Ile Pro Ala Leu Phe Leu Phe
 65                  70                  75                  80

Lys Asn Gly Gln Val Val Ser Asn Lys Val Gly Ala Ala Pro Lys Ala
                 85                  90                  95

Ala Leu Ala Thr Trp Ile Ala Ser Ala Leu Met Ser Ile Ile Ile Ala
            100                 105                 110

Thr Asn Ser Thr Glu His Pro Ile Phe Arg Pro Leu Ala Asn Phe Pro
        115                 120                 125

Pro Ser Leu Trp Gly Asn Leu Phe Thr Ser Phe Ser Met Asp Asn Gln
    130                 135                 140

Ala Arg Glu Ile Tyr Ala Lys Glu His Glu Gly Leu Lys Glu Lys Val
145                 150                 155                 160

Arg Met Met Phe Leu Asp Thr Thr Asn Tyr Lys Ile Ser Glu Lys Ile
                165                 170                 175

Asn Phe Ile Asn Thr Val Glu Arg Leu Gly Val Ser Tyr His Phe Glu
                180                 185                 190

Lys Glu Ile Glu Glu Leu Leu His Gln Met Phe Asp Ala His Ser Lys
                195                 200                 205

His Leu Asp Asp Ile Gln Glu Phe Asp Leu Phe Thr Leu Gly Ile Tyr
    210                 215                 220

Phe Arg Ile Leu Arg Gln His Gly Tyr Lys Ile Ser Cys Asp Val Phe
225                 230                 235                 240

Asn Lys Leu Lys Asp Ser Asn Gly Glu Phe Lys Asp Glu Leu Lys Asp
                245                 250                 255

Asp Val Asn Gly Met Leu Ser Phe Tyr Glu Ala Thr His Val Arg Thr
                260                 265                 270

His Gly Glu Asn Ile Leu Asp Glu Ala Leu Ile Tyr Thr Lys Ala Gln
                275                 280                 285

Leu Glu Ser Met Ala Ala Ala Ser Leu Ser Pro Phe Leu Ala Asn Gln
    290                 295                 300

Val Lys His Ala Leu Met Gln Ala Leu His Lys Gly Ile Pro Arg Ile
305                 310                 315                 320

Glu Ala Arg Asn Tyr Ile Ser Val Tyr Glu Glu Asp Pro Asn Lys Asn
                325                 330                 335

Asp Leu Leu Leu Arg Phe Ser Lys Ile Asp Phe Asn Leu Val Gln Met
            340                 345                 350

Ile His Lys Gln Glu Leu Cys Asp Thr Phe Arg Trp Trp Lys Asp Leu
        355                 360                 365

Glu Phe Glu Ser Lys Leu Ser Phe Ala Arg Asn Arg Val Val Glu Ala
    370                 375                 380

Tyr Leu Trp Thr Leu Ser Ala Tyr Tyr Glu Pro Lys Tyr Ser Ser Ala
385                 390                 395                 400

Arg Ile Ile Leu Val Lys Leu Met Val Ile Ile Ser Val Thr Asp Asp
                405                 410                 415

Thr Tyr Asp Ala Tyr Gly Thr Leu Asp Glu Leu Gln Leu Phe Thr Asp
                420                 425                 430

Ala Ile Gln Arg Leu Asp Met Ser Ser Ile Asn Gln Leu Pro Asp Tyr
            435                 440                 445

Met Lys Thr Ile Tyr Lys Ala Leu Leu Asp Leu Phe Asp Glu Ile Glu
        450                 455                 460

Asp Arg Leu Ser Lys His Glu Thr Asp His Ser Tyr Arg Val Ala Tyr
465                 470                 475                 480

Ala Lys Tyr Val Tyr Lys Glu Ile Val Arg Cys Tyr Asp Met Glu Tyr
```

```
            485                 490                 495
Lys Trp Phe Asn Lys Asn Tyr Val Pro Ala Phe Glu Glu Tyr Met Gln
            500                 505                 510

Lys Ala Leu Val Thr Ser Gly Asn Arg Leu Leu Ile Thr Phe Ser Phe
            515                 520                 525

Leu Gly Met Asp Glu Val Ala Thr Ile Gln Ala Phe Glu Trp Val Lys
            530                 535                 540

Ser Asn Ala Lys Met Ile Val Ser Ser Asn Lys Val Leu Arg Leu Ile
545                 550                 555                 560

Asp Asp Ile Met Ser His Glu Glu Asp Glu Arg Gly His Val Ala
                565                 570                 575

Thr Gly Ile Glu Cys Phe Val Lys Glu His Gly Leu Thr Arg Glu Glu
                580                 585                 590

Val Ile Val Glu Phe His Lys Arg Ile Asp Asp Ala Trp Lys Asp Ile
            595                 600                 605

Asn Glu Glu Phe Ile Thr Pro Asn Asn Leu Pro Ile Glu Ile Leu Thr
610                 615                 620

Arg Val Leu Asn Leu Thr Arg Ile Gly Asp Val Val Tyr Lys Tyr Asp
625                 630                 635                 640

Asp Gly Tyr Thr His Pro Glu Lys Ala Leu Lys Asp His Ile Ile Ser
                645                 650                 655

Leu Phe Val Asp Pro Val Ser Ile
                660

<210> SEQ ID NO 28
<211> LENGTH: 21
<212> TYPE: DNA
<213> ORGANISM: Artificial Sequence
<220> FEATURE:
<223> OTHER INFORMATION: GST_NjPAT_Rv Nucleotide sequence

<400> SEQUENCE: 28
atcgacatct tgggcggatg g                                          21

<210> SEQ ID NO 29
<211> LENGTH: 25
<212> TYPE: DNA
<213> ORGANISM: Artificial Sequence
<220> FEATURE:
<223> OTHER INFORMATION: GST_NjPAT_Fw Nucleotide sequence

<400> SEQUENCE: 29
gcccaagatg tcgatcatca tcgcc                                      25

<210> SEQ ID NO 30
<211> LENGTH: 2418
<212> TYPE: DNA
<213> ORGANISM: Artificial Sequence
<220> FEATURE:
<223> OTHER INFORMATION: SPppa-GST-NjPAT Nucleotide sequence

<400> SEQUENCE: 30
aaatttattt gctttgtgag cggataacaa ttattagatt caccggcgag ccagcaggaa    60
tttcactcta gatgacagga gggacatatg tcgccgatcc tgggctattg aagatcaag    120 ggcctcgtgc agcccacccg cctgctcctg agtacctgg aggagaagta tgaggagcac    180
ctctacgagc gcgacgaggg cgacaagtgg cgcaacaaga agttcgagct cggcctggag    240
ttcccgaacc tgccctacta tatcgacggc gacgtgaagc tcacgcagtc gatggccatc    300
```

```
atccgctaca tcgcggacaa gcataacatg ctgggcggct gccccaagga gcgcgcggag    360
atctcgatgc tggagggcgc ggtgctcgac atccgctatg cgtgtcgcg catcgcctac     420
tcgaaggact cgagaccct gaaggtggac ttcctctcga agctgccgga gatgctcaag     480
atgttcgagg accgcctgtg ccacaagacc tatctcaacg cgaccacgt gacgcatccc     540
gacttcatgc tctatgacgc gctggacgtg gtgctctaca tggacccgat gtgcctggac    600
gccttcccca agctcgtgtg cttcaagaag cgcatcgagg cgatcccgca gatcgacaag    660
tatctgaagt cgtcgaagta catcgcctgg cccctccagg gctggcaggc gacgttcggc    720
ggcggcgacc atccgcccaa gatgtcgatc atcatcgcca ccaacagcac cgagcatccc    780
atcttccgcc cgctcgccaa cttcccgccg tcgctctggg gcaacctgtt cacctcgttc    840
agcatggaca accaggcgcg cgagatctac gccaaggagc acgagggcct caaggagaag    900
gtccggatga tgttcctgga caccacgaac tacaagatct cggagaagat caacttcatc    960
aacaccgtcg agcgcctggg cgtgagctat cacttcgaga aggagatcga ggagctgctc   1020
catcagatgt tcgacgccca ctcgaagcat ctggacgaca tccaggagtt cgacctcttc   1080
acgctgggca tctacttccg catcctgcgg cagcatggct ataagatctc gtgcgacgtc   1140
ttcaacaagc tgaaggacag caacggcgag ttcaaggacg agctcaagga cgacgtcaac   1200
ggcatgctgt cgttctatga ggccacccat gtgcgcaccc atggcgagaa catcctcgac   1260
gaggcgctga tctacacgaa ggcccagctg gagtcgatgg cggccgcctc gctcagcccg   1320
ttcctggcca accaggtgaa gcacgcgctc atgcaggccc tgcataaggg catcccgcgc   1380
atcgaggcgc ggaactacat ctcggtctat gaggaagacc cgaacaagaa cgacctgctc   1440
ctgcgcttca gcaagatcga cttcaacctg gtgcagatga tccacaagca ggagctgtgc   1500
gacaccttcc ggtggtggaa ggacctggag ttcgagtcga agctgtcgtt cgcccgcaac   1560
cgggtggtgg aggcctacct ctggacgctg tcggcgtact atgagccgaa gtattcgagc   1620
gcccgcatca tcctcgtgaa gctgatggtc atcatctcgg tgaccgacga cacgtacgac   1680
gcctatggca ccctggacga gctccagctg ttcacggacg cgatccagcg cctcgacatg   1740
tcgagcatca accagctgcc cgactacatg aagaccatct ataaggcgct cctggacctc   1800
ttcgacgaga tcgaggaccg cctgtcgaag cacgagacgg accatagcta ccgggtggcg   1860
tatgccaagt acgtctataa ggagatcgtg cgctgctacg acatggagta taagtggttc   1920
aacaagaact acgtccccgc cttcgaggag tatatgcaga aggccctggt gacctcgggc   1980
aaccggctcc tgatcacgtt cagcttcctg ggcatggacg aggtcgcgac catccaggcc   2040
ttcgagtggg tgaagtcgaa cgccaagatg atcgtgtcgt cgaacaaggt gctccgcctg   2100
atcgacgaca tcatgtcgca cgaggaagag gacgagcgcg gccatgtggc cacgggcatc   2160
gagtgcttcg tgaaggagca cggcctgacc cgcgaggaag tgatcgtcga gttccataag   2220
cggatcgacg acgcgtggaa ggacatcaac gaggagttca tcaccccgaa caacctgccg   2280
atcgagatcc tgacccgcgt gctcaacctg acccggatcg cgacgtggt ctacaagtat    2340
gacgacggct acacgcaccc cgagaaggcc ctcaaggacc atatcatcag cctgttcgtg   2400
gaccccgtca gcatctga                                                  2418
```

<210> SEQ ID NO 31
<211> LENGTH: 776
<212> TYPE: PRT
<213> ORGANISM: Artificial Sequence
<220> FEATURE:
<223> OTHER INFORMATION: GST-NjPAT Aminoacid sequence

<400> SEQUENCE: 31

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Met Ser Ile Ile Ile Ala
210                 215                 220

Thr Asn Ser Thr Glu His Pro Ile Phe Arg Pro Leu Ala Asn Phe Pro
225                 230                 235                 240

Pro Ser Leu Trp Gly Asn Leu Phe Thr Ser Phe Ser Met Asp Asn Gln
                245                 250                 255

Ala Arg Glu Ile Tyr Ala Lys Glu His Glu Gly Leu Lys Glu Lys Val
            260                 265                 270

Arg Met Met Phe Leu Asp Thr Thr Asn Tyr Lys Ile Ser Glu Lys Ile
        275                 280                 285

Asn Phe Ile Asn Thr Val Glu Arg Leu Gly Val Ser Tyr His Phe Glu
290                 295                 300

Lys Glu Ile Glu Glu Leu Leu His Gln Met Phe Asp Ala His Ser Lys
305                 310                 315                 320

His Leu Asp Asp Ile Gln Glu Phe Asp Leu Phe Thr Leu Gly Ile Tyr
                325                 330                 335

Phe Arg Ile Leu Arg Gln His Gly Tyr Lys Ile Ser Cys Asp Val Phe
            340                 345                 350

Asn Lys Leu Lys Asp Ser Asn Gly Glu Phe Lys Asp Glu Leu Lys Asp
        355                 360                 365

Asp Val Asn Gly Met Leu Ser Phe Tyr Glu Ala Thr His Val Arg Thr
370                 375                 380

His Gly Glu Asn Ile Leu Asp Glu Ala Leu Ile Tyr Thr Lys Ala Gln
385                 390                 395                 400

Leu Glu Ser Met Ala Ala Ala Ser Leu Ser Pro Phe Leu Ala Asn Gln

```
                    405                 410                 415
Val Lys His Ala Leu Met Gln Ala Leu His Lys Gly Ile Pro Arg Ile
                420                 425                 430

Glu Ala Arg Asn Tyr Ile Ser Val Tyr Glu Asp Pro Asn Lys Asn
            435                 440                 445

Asp Leu Leu Leu Arg Phe Ser Lys Ile Asp Phe Asn Leu Val Gln Met
450                 455                 460

Ile His Lys Gln Glu Leu Cys Asp Thr Phe Arg Trp Trp Lys Asp Leu
465                 470                 475                 480

Glu Phe Glu Ser Lys Leu Ser Phe Ala Arg Asn Arg Val Val Glu Ala
                485                 490                 495

Tyr Leu Trp Thr Leu Ser Ala Tyr Tyr Glu Pro Lys Tyr Ser Ser Ala
                500                 505                 510

Arg Ile Ile Leu Val Lys Leu Met Val Ile Ser Val Thr Asp Asp
                515                 520                 525

Thr Tyr Asp Ala Tyr Gly Thr Leu Asp Glu Leu Gln Leu Phe Thr Asp
                530                 535                 540

Ala Ile Gln Arg Leu Asp Met Ser Ser Ile Asn Gln Leu Pro Asp Tyr
545                 550                 555                 560

Met Lys Thr Ile Tyr Lys Ala Leu Leu Asp Leu Phe Asp Glu Ile Glu
                565                 570                 575

Asp Arg Leu Ser Lys His Glu Thr Asp His Ser Tyr Arg Val Ala Tyr
                580                 585                 590

Ala Lys Tyr Val Tyr Lys Glu Ile Val Arg Cys Tyr Asp Met Glu Tyr
                595                 600                 605

Lys Trp Phe Asn Lys Asn Tyr Val Pro Ala Phe Glu Glu Tyr Met Gln
                610                 615                 620

Lys Ala Leu Val Thr Ser Gly Asn Arg Leu Leu Ile Thr Phe Ser Phe
625                 630                 635                 640

Leu Gly Met Asp Glu Val Ala Thr Ile Gln Ala Phe Glu Trp Val Lys
                645                 650                 655

Ser Asn Ala Lys Met Ile Val Ser Ser Asn Lys Val Leu Arg Leu Ile
                660                 665                 670

Asp Asp Ile Met Ser His Glu Glu Glu Asp Arg Gly His Val Ala
                675                 680                 685

Thr Gly Ile Glu Cys Phe Val Lys Glu His Gly Leu Thr Arg Glu Glu
                690                 695                 700

Val Ile Val Glu Phe His Lys Arg Ile Asp Asp Ala Trp Lys Asp Ile
705                 710                 715                 720

Asn Glu Glu Phe Ile Thr Pro Asn Asn Leu Pro Ile Glu Ile Leu Thr
                725                 730                 735

Arg Val Leu Asn Leu Thr Arg Ile Gly Asp Val Val Tyr Lys Tyr Asp
                740                 745                 750

Asp Gly Tyr Thr His Pro Glu Lys Ala Leu Lys Asp His Ile Ile Ser
                755                 760                 765

Leu Phe Val Asp Pro Val Ser Ile
                770                 775
```

TERPENE SYNTHASE PRODUCING PATCHOULOL AND ELEMOL, AND PREFERABLY ALSO POGOSTOL

CROSS-REFERENCE TO RELATED APPLICATIONS

This application is a national stage application (under 35 U.S.C. § 371) of International Application No. PCT/NL2018/050565, filed Sep. 1, 2018, which designated the U.S. and which claims priority to NL Patent Application No. 2019473, filed Sep. 1, 2017, the entire contents of each of which are hereby incorporated by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_074008_2026. The size of the text file is 73,962 bytes and the text file was created on Jun. 30, 2020.

The invention is directed to a patchoulol synthase, to a nucleic acid encoding said patchoulol synthase, to an expression vector comprising said nucleic acid, to a host cell comprising said expression vector, to a method of preparing patchoulol and elemol, and preferably also pogostol, and to a method of preparing a patchoulol synthase.

Many organisms have the capacity to produce a wide array of terpenes and terpenoids. Terpenes are actually or conceptually built up from 2-methylbutane residues, usually referred to as units of isoprene, which has the molecular formula $C_5H_8$. One can consider the isoprene unit as one of nature's common building blocks. The basic molecular formulae of terpenes are multiples of that formula: $(C_5H_8)_n$, wherein n is the number of linked isoprene units. This is called the isoprene rule, as a result of which terpenes are also denoted as isoprenoids. The isoprene units may be linked together "head to tail" to form linear chains or they may be arranged to form rings. In their biosynthesis, terpenes are formed from the universal 5 carbon precursors isopentenyl diphosphate (IPP) and its isomer, dimethylallyl diphosphate (DMAPP). Accordingly, a terpene carbon skeleton generally comprises a multiple of 5 carbon atoms. Most common are the 5-, 10-, 15-, 20-, 30- and 40-carbon terpenes, which are referred to as hemi-, mono-, sesqui-, di-, tri- and tetraterpenes, respectively. Besides "head-to-tail" connections, tri- and tetraterpenes also contain one "tail-to-tail" connection in their centre. The terpenes may comprise further functional groups, like alcohols and their glycosides, ethers, aldehydes, ketones, carboxylic acids and esters. These functionalised terpenes are herein referred to as terpenoids. Like terpenes, terpenoids generally have a carbon skeleton having a multiple of 5 carbon atoms. It should be noted that the total number of carbons in a terpenoid does not need to be a multiple of 5, e.g. the functional group may be an ester group comprising an alkyl radical having any number of carbon atoms.

Apart from the definitions given above, it is important to note that the terms "terpene", "terpenoid" and "isoprenoid" are frequently used interchangeably in open as well as patent literature.

Patchoulol is a naturally occurring sesquiterpene alcohol, produced in specific plants, such as patchouli (*Pogostemon cablin*), a herbaceous plant of the mint family (Lamiaceae). Patchoulol is a major constituent of patchouli oil. Patchouli oil is an important perfumery ingredient obtained by steam distillation of the dried leaves of *Pogostemon*. Patchouli oil is an important fragrance ingredient used in fine perfumes, cosmetics like skin cream, lipstick, powder, shampoo, shaving cream, hair oil and soap perfumes. Patchouli oil has a characteristic odor profile which has been described as warm, herbaceous, camphoraceous and woody. Patchoulol is not only the main component of patchouli oil but also the key odor component (Näf et al. *Heiretica Chimica Acta* 64, no. 5 (Jul. 22, 1981): 1387-97). Patchouli oil does however contain may additional components of which norpatchoulenol and pogostol have been described as important contributors to the patchouli odor profile (Leffingwell et al. *Chemistry Today* (2006): 24: 36-38).

A single patchoulol synthase from *Pogostemon cablin* was found to be responsible for producing the majority of patchouli oil components (Deguerry et al. *Archives of Biochemistry and Biophysics* (2006): 454: 123-36). Chemical routes to enatiopure patchoulol are available (Näf et al. *Helvetica Chimica Acta* 64, no. 5 (Jul. 22, 1981): 1387-97, and Srikrishna et al. *Tetrahedron: Asymmetry* (2005): 16: 3992-97), but do not allow for a cost-effective production of patchoulol. Therefore patchoulol is obtained mainly from steam-distillation of dried leafes of patchouli plants. The supply of patchouli oil is mainly coming from Indonesia. This supply is subject to strong fluctuations in prize, quality and availability. These fluctuations are caused by several factors, among which are climate change, trade speculation, farming practices, fluctuations in production costs, changes in production area and plant diseases (Tekriwal S (2009) Naturals in Indonesia (www.scribd.com/document/251903018/Naturals-in-Indonesia-IFEAT-Shanghai-By-Sandeep-Tekriwal)).

It has been proposed to prepare patchoulol microbiologically, making use of micro-organisms genetically modified by incorporation of a gene that is coding for a protein having patchoulol synthase activity. A patchoulol synthase can be used for the preparation of patchoulol from FPP, a conversion which might be executed as an isolated reaction (in vitro) or as part of a longer metabolic pathway eventually leading to the production of patchoulol from sugar (in vivo).

US20090205060 describes a method for producing patchoulol using a patchoulol synthase from *Pogostemon cablin*. U.S. Pat. No. 8,993,284, WO2011141855 describes a terpene synthases from *Valeriana jatamansi* producing patchoulol and 7-epi-alpha-selinene concurrently.

Firmenich has introduced its CLEARWOOD™ patchouli oil substitute in 2014, which is derived from fermentative production from sugar and described as a "soft, clean version of Patchouli without the earthy, leathery and rubbery notes found in the natural oil" (Leffingwell et al. *Leffingwell Reports* (2015) 7: 1-11).

The only terpene synthases known to form patchoulol have so far been identified in the genera *Pogostemon* and *Valeriana*. Other plants have however been described to produce some of the patchoulol-type sesquiterpenes (Choudhury et al. *India. J. Essent. Res.* (1996): 8, 633), but the corresponding synthase enzymes are inknown.

The currently known patchoulol synthases have a number of distinct drawbacks which are in particular undesirable when they are applied in an industrial patchoulol production process wherein patchoulol is prepared from FPP, either in an isolated reaction (in vitro), e.g. using an isolated patchoulol synthase or (permeabilized) whole cells, or otherwise, e.g. in a fermentative process being part of a longer metabolic pathway. Thus, there is a need for an alternative patchoulol synthase which may be used in the preparation of patchoulol. In particular there is a need for an alternative patchoulol synthase that displays an improved expression, at least in selected host cells; an alternative patchoulol synthase that has a high enzymatic activity at least under specific conditions, such as at a neutral or alkaline pH and/or intracellularly in the cell wherein it has been produced; and/or an alternative patchoulol synthase that is highly specific, in particular that has improved specificity compared to patchoulol synthase from *Pogostemon cablin*, with respect to catalysing the conversion of FPP into patchoulol other patchoulol-like terpenes, at least under specific conditions, such as at about neutral or at alkaline pH and/or intracellularly in the cell wherein it has been produced.

It has been found that a specific polypeptide that was hitherto unknown has patchoulol synthase activity and that this polypeptide can be used as a catalyst that may serve as an alternative to known patchoulol synthases. It was also found that this patchoulol synthase produces also the sesquiterpene alcohols pogostol and elemol. A patchoulol synthesizing enzyme that also synthesizes elemol was hitherto unknown and the concomitant synthesis of patchoulol and elemol this novel patchoulol synthase is particular advantageous for industrial patchoulol production processes. Elemol has been described as having a sweet-woody odour, and essential oil fractions rich in elemol (e.g. from Elemi oil and Citronella oil) are used in perfumery as fixatives, blenders or modifiers (Ansari & Curtis, *J. Soc. Cosmet Chem* (1974): 25, 203-231.

Accordingly, the present invention relates to a patchoulol synthase comprising an amino acid sequence as shown in SEQ ID NO: 4, or a functional homologue thereof, said functional homologue being a patchoulol synthase comprising an amino acid sequence which has a sequence identity of at least 75% with SEQ ID NO: 4. Said homologue may in particular be a patchoulol synthase comprising an amino acid sequence which has a sequence identity of at least 80%, at least 85%, at least 90%, at least 95%, at least 98% or at least 99% with SEQ ID NO: 4.

The invention further relates to a nucleic acid, comprising a nucleic acid sequence encoding a patchoulol synthase according to the invention, or comprising a nucleic acid sequence complementary to said encoding sequence. In particular, the nucleic acid may be selected from nucleic acids comprising a nucleic acid sequence as shown in SEQ ID NO: 3 or SEQ ID NO: 5, and other nucleic acid sequences encoding a patchoulol synthase according to the invention, said other sequences comprising a nucleic acid sequence having a sequence identity of at least 75%, in particular of at least 80%, at least 85%, at least 90%, at least 95%, at least 98% or at least 99% with the nucleic acid sequence shown in SEQ ID NO: 3 or SEQ ID NO: 5, or respectively nucleic acids complementary thereto. Said other nucleic acid sequence encoding a patchoulol synthase according to the invention may herein after be referred to as a functional analogue.

A patchoulol synthase or nucleic acid according to the invention may be a natural compound or fragment of a compound isolated from its natural source (e.g. *Nardostachys jatamansi*), be a chemically or enzymatically synthesised compound or fragment of a compound or a compound or fragment of a compound produced in a recombinant cell, in which recombinant cell it may be present or from which cell it may have been isolated.

The invention further relates to an expression vector comprising a nucleic acid according to the invention.

The invention further relates to a host cell, which may be an organism per se or part of a multi-cellular organism, comprising an expression vector comprising a nucleic acid, preferably a nucleic acid heterologous to said host cell, according to the invention. The host cell is preferably selected form the group of bacterial cells, fungal cells (including yeast) and plant cells.

The invention further relates to a method for preparing patchoulol and elemol, and preferably also pogostol, comprising converting FPP to patchoulol and elemol, and preferably also pogostol in the presence of a patchoulol synthase according to the invention. Four different geometric isomers of FPP can exist, i.e. 2E,6E-FPP, 2Z,6E-FPP, 2E,6Z-FPP, and 2Z,6Z-FPP. Good results have been obtained with 2E,6E-FPP, although in principle any other isomer of FPP may be a suitable substrate for an enzyme according to the invention.

The invention is further directed to a method for producing a patchoulol synthase according to the invention, comprising culturing a host cell according to the invention under conditions conducive to the production of the patchoulol synthase and, optionally, recovering the patchoulol synthase from the host cell.

A patchoulol synthase according to the invention has surprisingly been found to produce patchoulol as well as elemol. Before the current invention no terpene synthase was available that produces both, patchoulol and elemol. Further, a patchoulol synthase according to the invention produces pogostol. A patchoulol synthase according to the invention, thus has a favourable product spectrum as compared to, e.g., a patchoulol synthase from *Pogostemon cablin*, in particular at or around neutral pH in an in vitro assay or in a method wherein patchoulol and elemol, and preferably also pogostol are synthesised intracellularly in a host cell genetically modified to produce a patchoulol synthase according to the invention and a *Pogostemon cablin* patchoulol synthase, respectively. Preferably, a patchoulol synthase according to the invention thus produces patchoulol and elemol, preferably having a ratio of elemol to patchoulol of between 1:5-1:9, preferably between 1:6-1:8, more preferably between 1:6.5-1:7.5 most preferably about 1:6.9, Preferably, a patchoulol synthase according to the invention also produces pogostol, preferably having a ratio pogostol to patchoulol of between 1:4-1:7, preferably between 1:4.5-1:65, more preferably between 1:5-1.6, most preferably about 1:5.6. More preferably, the ratio elemol to pogostol is between 1:0.7-1:2.25, preferably between 1:0.9-1:1.75, more preferably between 1:1.1-1:1.5, most preferably about 1:1.3.

In accordance with the invention it has been found possible to bring the patchoulol synthase to expression with good yield in distinct organisms. For instance, the patchoulol synthase has been found to be expressed well in *E. coli, Rhodobacter sphaeroides* and in *Nicotiana benthamiana* plants.

Thus, in an advantageous embodiment, the present invention provides a patchoulol synthase with improved specificity towards the catalysis of patchoulol synthesis and an improved production rate for patchoulol and elemol, and preferably also pogostol, when used in a method for preparing patchoulol and elemol, and preferably also pogostol, in particular compared to patchoulol synthase from *Pogostemon cablin* or another patchoulol synthase according to the prior art, cited herein.

In a preferred embodiment, a method for preparing patchoulol and elemol, and preferably also pogostol according to the invention is provided, wherein the patchoulol and elemol, and preferably also pogostol is prepared in a host cell, a plant or plant culture, or a mushroom or mushroom culture, according to the invention, expressing said patchoulol synthase. Preferably, the method for preparing patchoulol and elemol, and preferably also pogostol according to the invention further comprises isolating the patchoulol, pogostol and/or elemol from said host cell, plant or plant culture, or mushroom or mushroom culture. Preferably, the method for preparing patchoulol according to the invention results in a pogostol to patchoulol ratio of between 1:4-1:7, preferably between 1:4.5-1:65, more preferably between 1:5-1.6, most preferably about 1:5.6, an elemol to patchoulol ratio of between 1:5-1:9, preferably between 1:6-1:8, more preferably between 1:6.5-1:7.5 most preferably about 1:6.9, and/or an elemol to pogostol ratio of between 1:0.7-1:2.25, preferably between 1:0.9-1:1.75, more preferably between 1:1.1-1:1.5, most preferably about 1:1.3.

Without being bound by theory, it is thought that a high specificity towards the catalysis of patchoulol synthesis at neutral or mildly alkaline pH is in particular considered desirable for methods wherein the patchoulol is prepared intracellularly, because various host cells are thought to have a neutral or slightly alkaline intracellular pH, such as a pH of 7.0-8.5 (for intracellular pH values of bacteria, see for instance: Booth, Microbiological Reviews (1985) 49: 359-378). When, for instance, E. coli cells were exposed to pH values ranging from 5.5 to 8.0, the intracellular pH was between 7.1 and 7.9 (Olsen et al., Appl. Environ. Microbiol. (2002) 68: 4145-4147). This may explain an improved specificity towards the synthesis of patchoulol of a patchoulol synthase according to the invention, also intracellularly.

The term "or" as used herein is defined as "and/or" unless specified otherwise.

The term "a" or "an" as used herein is defined as "at least one" unless specified otherwise.

When referring to a noun (e.g. a compound, an additive, etc.) in the singular, the plural is meant to be included.

The terms farnesyl diphosphate and farnesylpyrophosphate (both abbreviated as FPP) as interchangeably used herein refer to the compound 3,7,11-trimethyl-2,6,10-dodecatrien-1-yl pyrophosphate and include all known isomers of this compound.

The term "recombinant" in relation to a recombinant cell, vector, nucleic acid or the like as used herein, refers to a cell, vector, nucleic acid or the like, containing nucleic acid not naturally occurring in that cell, vector, nucleic acid or the like and/or not naturally occurring at that same location. Generally, said nucleic acid has been introduced into that strain (cell) using recombinant DNA techniques.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which they are introduced, but have been obtained from another cell or synthetically or recombinantly produced. Generally, though not necessarily, such nucleic acids encode proteins that are not normally produced by the cell in which the DNA is expressed.

A gene that is endogenous to a particular host cell but has been modified from its natural form, through, for example, the use of DNA shuffling, is also called heterologous. The term "heterologous" also includes non-naturally occurring multiple copies of a naturally occurring DNA sequence.

Thus, the term "heterologous" may refer to a DNA segment that is foreign or heterologous to the cell, or homologous to the cell but in a position and/or a number within the host cell nucleic acid in which the segment is not ordinarily found. Exogenous DNA segments are expressed to yield exogenous polypeptides. A "homologous" DNA sequence is a DNA sequence that is naturally associated with a host cell into which it is introduced.

Any nucleic acid or protein that one of skill in the art would recognize as heterologous or foreign to the cell in which it is expressed is herein encompassed by the term heterologous nucleic acid or protein.

The term "mutated" or "mutation" as used herein regarding proteins or polypeptides means that at least one amino acid in the wild-type or naturally occurring protein or polypeptide sequence has been replaced with a different amino acid, or deleted from, or inserted into the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sambrook, J., and Russell, D. W. Molecular Cloning: A Laboratory Manual. 3d ed., Cold Spring Harbor Laboratory Press, Cold Spring Harbor, N.Y., (2001). The term "mutated" or "mutation" as used herein regarding genes means that at least one nucleotide in the nucleotide sequence of that gene or a regulatory sequence thereof, has been replaced with a different nucleotide, or has been deleted from or inserted into the sequence via mutagenesis.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

The term "gene" is used broadly to refer to any segment of nucleic acid associated with a biological function. Thus, genes include coding sequences and/or the regulatory sequences required for their expression. For example, gene refers to a nucleic acid fragment that expresses mRNA or functional RNA, or encodes a specific protein, and which includes regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The term "chimeric gene" refers to any gene that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

The term "transgenic" for a transgenic cell or organism as used herein, refers to an organism or cell (which cell may be an organism per se or a cell of a multi-cellular organism from which it has been isolated) containing a nucleic acid not naturally occurring in that organism or cell and which nucleic acid has been introduced into that organism or cell (i.e. has been introduced in the organism or cell itself or in an ancestor of the organism or an ancestral organism of an organism of which the cell has been isolated) using recombinant DNA techniques.

A "transgene" refers to a gene that has been introduced into the genome by transformation and preferably is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

"Transformation" and "transforming", as used herein, refers to the introduction of a heterologous nucleotide sequence into a host cell, irrespective of the method used for the insertion, for example, direct uptake, transduction, conjugation, f-mating or electroporation. The exogenous polynucleotide may be maintained as a non-integrated vector, for example, a plasmid, or alternatively, may be integrated into the host cell genome.

"Coding sequence" refers to a DNA or RNA sequence that codes for a specific amino acid sequence and excludes the non-coding sequences. It may constitute an "uninterrupted coding sequence", i.e. lacking an intron, such as in a cDNA or it may include one or more introns bound by appropriate splice junctions. An "intron" is a sequence of RNA which is contained in the primary transcript but which is removed through cleavage and re-ligation of the RNA within the cell to create the mature mRNA that can be translated into a protein.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences. As is noted above, the term "suitable regulatory sequences" is not limited to promoters.

Examples of regulatory sequences include promoters (such as transcriptional promoters, constitutive promoters, inducible promoters), operators, or enhancers, mRNA ribosomal binding sites, and appropriate sequences which control transcription and translation initiation and termination. Nucleic acid sequences are "operably linked" when the regulatory sequence functionally relates to the cDNA sequence of the invention.

Each of the regulatory sequences may independently be selected from heterologous and homologous regulatory sequences.

"Promoter" refers to a nucleotide sequence, usually upstream (5') to its coding sequence, which controls the expression of said coding sequence by providing the recognition for RNA polymerase and other factors required for proper transcription. "Promoter" includes a minimal promoter that is a short DNA sequence comprised of a TATA box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

The term "nucleic acid" as used herein, includes reference to a deoxyribonucleotide or ribonucleotide polymer, i.e. a polynucleotide, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are "polynucleotides" as the term is used herein. It will be appreciated that a great variety of modifications have been made to DNA and RNA that serve many useful purposes known to those of skill in the art. The term "polynucleotide" as it is employed herein embraces such chemically, enzymatically or metabolically modified forms of polynucleotides, as well as the chemical forms of DNA and RNA characteristic of viruses and cells, including among other things, simple and complex cells.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, the term "conservatively modified variants" refers to those nucleic acids which encode identical or conservatively modified variants of the amino acid sequences due to the degeneracy of the genetic code. The term "degeneracy of the genetic code" refers to the fact that a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations" and represent one species of conservatively modified variation. The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulphation, gamma-carboxylation of glutamic acid residues, hydroxylation and ADP-ribosylation.

Within the context of the present application, oligomers (such as oligonucleotides, oligopeptides) are considered a species of the group of polymers. Oligomers have a relatively low number of monomeric units, in general 2-100, in particular 6-100.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development.

The term "vector" as used herein refers to a construction comprised of genetic material designed to direct transformation of a targeted cell. A vector contains multiple genetic elements positionally and sequentially oriented, i.e., operatively linked with other necessary elements such that the nucleic acid in a nucleic acid cassette can be transcribed and when necessary, translated in the transformed cells.

In particular, the vector may be selected from the group of viral vectors, (bacterio)phages, cosmids or plasmids. The vector may also be a yeast artificial chromosome (YAC), a bacterial artificial chromosome (BAC) or *Agrobacterium* binary vector. The vector may be in double or single stranded linear or circular form which may or may not be self transmissible or mobilizable, and which can transform prokaryotic or eukaryotic host either by integration into the cellular genome or exist extrachromosomally (e. g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eukaryotic (e. g. higher plant, mammalian, yeast or fungal cells). Preferably the nucleic acid in the vector is under the control of, and operably linked to, an appropriate promoter or other regulatory elements for transcription in a host cell such as a microbial, e. g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

Vectors containing a polynucleic acid according to the invention can be prepared based on methodology known in the art per se. For instance use can be made of a cDNA sequence encoding the polypeptide according to the invention operably linked to suitable regulatory elements, such as transcriptional or translational regulatory nucleic acid sequences.

The term "vector" as used herein, includes reference to a vector for standard cloning work ("cloning vector") as well as to more specialized type of vectors, like an (autosomal) expression vector and a cloning vector used for integration into the chromosome of the host cell ("integration vector").

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector.

The term "expression vector" refers to a DNA molecule, linear or circular, that comprises a segment encoding a polypeptide of interest under the control of (i.e. operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular, an expression vector comprises a nucleotide sequence that comprises in the 5' to 3' direction and operably linked: (a) a transcription and translation initiation region that are recognized by the host organism, (b) a coding sequence for a polypeptide of interest, and (c) a transcription and translation termination region that are recognized by the host organism. "Plasmid" refers to autonomously replicating extrachromosomal DNA which is not integrated into a microorganism's genome and is usually circular in nature.

An "integration vector" refers to a DNA molecule, linear or circular, that can be incorporated into a microorganism's genome and provides for stable inheritance of a gene encoding a polypeptide of interest. The integration vector generally comprises one or more segments comprising a gene sequence encoding a polypeptide of interest under the control of (i.e., operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

As used herein, the term "operably linked" or "operatively linked" refers to a juxtaposition wherein the components so described are in a relationship permitting them to function in their intended manner. A control sequence "operably linked" to another control sequence and/or to a coding sequence is ligated in such a way that transcription and/or expression of the coding sequence is achieved under conditions compatible with the control sequence. Generally, operably linked means that the nucleic acid sequences being linked are contiguous and, where necessary to join two protein coding regions, contiguous and in the same reading frame.

The term "patchoulol synthase" is used herein for polypeptides having catalytic activity in the formation of patchoulol, and preferably also patchoulol-like terpenes like elemol or pogostol, from farnesyl diphosphate, and for other moieties comprising such a polypeptide. Examples of such other moieties include complexes of said polypeptide with one or more other polypeptides, fusion proteins of comprising a patchoulol synthase polypeptide fused to a peptide or protein tag sequence, other complexes of said polypeptides (e.g. metalloprotein complexes), macromolecular compounds comprising said polypeptide and another organic moiety, said polypeptide bound to a support material, etc. The patchoulol synthase can be provided in its natural environment, i.e. within a cell in which it has been produced, or in the medium into which it has been excreted by the cell producing it. It can also be provided separate from the source that has produced the polypeptide and can be manipulated by attachment to a carrier, labeled with a labeling moiety, and the like.

The term "functional homologue" of a sequence, or in short "homologue", as used herein, refers to a polypeptide comprising said specific sequence with the proviso that one or more amino acids are substituted, deleted, added, and/or inserted, and which polypeptide has (qualitatively) the same enzymatic functionality for substrate conversion in case the term 'functional homologue' is used for an enzyme, i.e. a homologue of the sequence with SEQ ID NO: 4 having catalytic activity in the formation of patchoulol from farnesyl diphosphate. In the examples a test is described that is suitable to verify whether a polypeptide or a moiety comprising a polypeptide is a patchoulol synthase ("Patchoulol synthase activity test"). Moreover, the skilled artisan recognises that equivalent nucleotide sequences encompassed by this invention can also be defined by their ability to hybridize, under low, moderate and/or stringent conditions, with the nucleotide sequences that are within the literal scope of the instant claims.

A preferred homologue to SEQ ID NO: 4 according to the invention has a specificity towards catalysis of patchoulol formation, expressed as the molar ratio pogostol to patchoulol of between 1:4-1:7, preferably between 1:4.5-1:65, more preferably between 1:5-1.6, most preferably about 1:5.6, an elemol to patchoulol ratio of between 1:5-1:9, preferably between 1:6-1:8, more preferably between 1:6.5-1:7.5 most preferably about 1:6.9, and/or an elemol to pogostol ratio of between 1:0.7-1:2.25, preferably between 1:0.9-1:1.75, more preferably between 1:1.1-1:1.5, most preferably about 1:1.3.

Sequence identity or similarity is defined herein as a relationship between two or more polypeptide sequences or two or more nucleic acid sequences, as determined by comparing those sequences. Usually, sequence identities or similarities are compared over the whole length of the sequences, but may however also be compared only for a part of the sequences aligning with each other. In the art, "identity" or "similarity" also means the degree of sequence relatedness between polypeptide sequences or nucleic acid sequences, as the case may be, as determined by the match between such sequences. Sequence identity as used herein is the value as determined by the EMBOSS Pairwise Alignment Algorithm "Needle", for instance at the server of the European Bioinformatics Institute (www.ebi.ac.uk/Tools/emboss/align/). For alignment of amino acid sequences the default parameters are: Matrix=Blosum62; Open Gap Penalty=10.0; Gap Extension Penalty=0.5. For alignment of nucleic acid sequences the default parameters are: Matrix=DNAfull; Open Gap Penalty=10.0; Gap Extension Penalty=0.5.

Discrepancies between a patchoulol synthase according to SEQ ID NO: 4 or a nucleic acid according to SEQ ID NO: 3 or SEQ ID NO: 5 on hand and a functional homologue of said patchoulol synthase may in particular be the result of modifications performed, e.g. to improve a property of the patchoulol synthase or polynucleic acid (e.g. improved expression) by a biological technique known to the skilled person in the art, such as e.g. molecular evolution or rational design or by using a mutagenesis technique known in the art (random mutagenesis, site-directed mutagenesis, directed evolution, gene recombination, etc.). The amino acid sequence or the coding nucleic acid sequence of patchoulol synthase may be altered compared to the sequences of SEQ ID NO: 4 and SEQ ID NO: 3 or SEQ ID NO: 5, respectively, as a result of one or more natural occurring variations. Examples of such natural modifications/variations are differences in glycosylation (more broadly defined as "post-translational modifications"), differences due to alternative splicing, and single-nucleic acid polymorphisms (SNPs). The nucleic acid may be modified such that it encodes a polypeptide that differs by at least one amino acid from the polypeptide of SEQ ID NO: 4, so that it encodes a polypeptide comprising one or more amino acid substitutions, deletions and/or insertions compared to SEQ ID NO: 4, which polypeptide still has essentially the same patchoulol synthase activity as that of SEQ ID NO: 4. Further, use may be made of codon optimisation or codon pair optimisation, e.g. based on a method as described in WO 2008/000632 or as offered by commercial DNA synthesizing companies like DNA2.0, Geneart, and GenScript. Examples of one codon optimised sequence is SEQ ID NO: 5.

One or more sequences encoding appropriate signal peptides that are not naturally associated with the polypeptides of the invention can be incorporated into (expression) vectors. For example, a DNA sequence for a signal peptide leader can be fused in-frame to a nucleic acid sequence of the invention so that the polypeptide of the invention is initially translated as a fusion protein comprising the signal peptide. Depending on the nature of the signal peptide, the expressed polypeptide will be targeted differently. A secretory signal peptide that is functional in the intended host cells, for instance, enhances extracellular secretion of the expressed polypeptide. Other signal peptides direct the expressed polypeptides to certain organelles, like the chloroplasts, mitochondria and peroxisomes. The signal peptide can be cleaved from the polypeptide upon transportation to the intended organelle or from the cell. It is possible to provide a fusion of an additional peptide sequence at the amino or carboxyl terminal end of a polypeptide according to SEQ ID NO: 4 or homologue thereof.

As mentioned above the invention further relates to a host cell comprising a vector according to the invention. By "host cell" is meant a cell which contains a vector and supports the replication and/or expression of the vector.

The nucleic acid of the invention is heterologous to the host cell of the invention. The host cell may be a prokaryotic cell, a eukaryotic cell or a cell from a member of the Archaea. The host cell may be from any organism, in particular any non-human organism. In particular, the host cell may be selected from bacterial cells, fungal cells, archaea, protists, plant cells (including algae), cells originating from an animal (in particular isolated from said animal). The host cell may form part of a multicellular organism, other than human or the organism from which the enzyme naturally originates (such as *Nardostachys jatamansi* in case of the patchoulol synthase of SEQ ID NO: 4). In a specific embodiment, host cells of the invention are in a culture of cells originating from a multicellular organism, yet isolated therefrom.

In general, the host cell is an isolated cell comprising genes for expressing the enzymes for catalysing the reaction steps of the mevalonate pathway or another metabolic pathway (such as the deoxyxylulose-5-phosphate (DXP) pathway) enabling the production of the C5 prenyl diphosphates isopentenyl diphosphate (IPP) and dimethylallyl diphosphate (DMAPP), which are the universal isoprenoid building blocks. As far as known, unless specific genes have been knocked-out, all known organisms comprise such a pathway. Eukaryotes generally are naturally capable of preparing IPP via the mevalonate pathway. This IPP is then isomerized into DMAPP by the action of the enzyme isopentenyl diphosphate isomerase (Idi). The DXP pathway, which is furnishing IPP and DMAPP in a 5:1 ratio, is common to prokaryotes, although several prokaryotes are naturally capable of preparing IPP via the mevalonate pathway. These pathways are known in the art, and have been described, e.g., by Withers & Keasling in Appl. Microbiol. Biotechnol (2007) 73: 980-990. The genes of these pathways may each independently be homologous or heterologous to the cell.

The host cells further will, either endogenically or from heterologous sources, comprise one or more genes for expressing enzymes with prenyl transferase activity catalysing the head-to-tail condensation of the C5 prenyl diphosphates producing longer prenyl diphosphates. The universal sesquiterpene precursor farnesyl diphosphate (FPP), for instance, is formed by the action of these enzymes through the successive head-to-tail addition of 2 molecules of IPP to 1 molecule of DMAPP.

In an embodiment, the host cell is a bacterium. The bacterium may be gram-positive or grain-negative. Grain-positive bacteria may be selected from the genera of *Bacillus, Lactobacillus*, and *Corynebacterium* spp, in particular from the species of *Bacillus subtilis, Lactobacillus casei*, and *Cornynebacterium glutamicum*.

In a preferred embodiment, the bacterium is selected from the group of Gram-negative bacteria, in particular from the group of *Rhodobacter, Paracoccus* and *Escherichia*, more in particular from the group of *Rhodobacter capsulatus, Rhodobacter sphaeroides, Paracoccus carotinifaciens, Paracoccus zeaxanthinifaciens* and *Escherichia coli*. *Rhodobacter sphaeroides* is an example of an organism naturally containing all genes needed for expressing enzymes catalysing the various reaction steps in the DXP pathway, enabling the intracellular production of IPP and DMAPP, and is especially preferred.

In a preferred embodiment, the host cell is a fungal cell, in particular a fungal cell selected from the group of *Aspergillus, Blakeslea, Penicillium, Phaffia (Xanthophyllomyces), Pichia, Saccharomyces* and *Yarrowia*, more in particular from the group of *Aspergillus nidulans, Aspergillus niger, Aspergillus oryzae, Blakeslea trispora, Penicillium chrysogenum, Phaffia rhodozyma (Xanthophyllomyees dendrorhous), Pichia pastoris, Saccharomyces cerevisiae* and *Yarrowia lipolytica*.

It is also possible to express the nucleic acids of the invention in cells derived from higher eukaryotic organisms, such as plant cells and animal cells, such as insect cell, or cells from mouse, rat or human. Said cells can be maintained in a cell or tissue culture and be used for in vitro production of patchoulol synthase.

A multicellular organism comprising host cells according to the invention may in particular be selected from the group of multicellular plants and mushrooms (*Basidiomycetes*).

Thus, in a specific embodiment, the invention relates to a transgenic plant or plant cell or tissue culture comprising transgenic plant cells, said plant or culture comprising plant host cells according to the invention. The transgenic plant or culture of transgenic plant cells may in particular be selected from *Nicotiana* spp., *Solanum* spp., *Cichorum intybus, Lactuca satira, Mentha* spp., *Artemisia annua*, tuber forming plants, such as *Helianthus tuberosus*, cassava and *Beta vulgaris*, oil crops, such as *Brassica* spp., *Elaeis* spp. (oil palm tree), *Helianthus annuus, Glycine max* and *Arachis hypogaea*, liquid culture plants, such as duckweed *Lemna* spp., tobacco BY2 cells and *Physcomitrella patens*, trees, such as pine tree and poplar, respectively a cell culture or a tissue culture of any of said plants. In a specific embodiment, the tissue culture is a hairy root culture.

In a further specific embodiment, the invention relates to a transgenic mushroom or culture comprising transgenic mushroom cells. The transgenic mushroom or culture comprising transgenic host cells, may in particular be selected from the group of *Schizophyllum, Agaricus* and *Pleurotus*, more in particular from *Schizophyllum commune*, the common mushroom (*Agaricus bisporus*), the oyster mushroom (*Pleurotus ostreotus* and *Pleurotus sapidus*), respectively a culture comprising cells of any of said mushrooms.

A host cell according to the invention may be produced based on standard genetic and molecular biology techniques that are generally known in the art, e.g. as described in Sambrook, J., and Russell, D. W. "Molecular Cloning: A Laboratory Manual" 3d ed., Cold Spring Harbor Laboratory Press, Cold Spring Harbor, N.Y., (2001); and F. M. Ausubel et al, eds., "Current protocols in molecular biology", John Wiley and Sons, Inc., New York (1987), and later supplements thereto.

Methods to transform *Basidiomycetes* are known from, for example, Alves et al. (Appl. Environ. Microbiol. (2004) 70: 6379-6384), Godio et al. (Curr. Genet. (2004) 46: 287-294), Schuurs et al. (Genetics (1997) 147: 589-596), and WO 06/096050. To achieve expression of a suitable patchoulol synthase gene in basidiomycetes, its complete open reading frame is typically cloned into an expression vector suitable for transformation of basidiomycetes.

The expression vector preferably also comprises nucleic acid sequences that regulate transcription initiation and termination. It is also preferred to incorporate at least one selectable marker gene to allow for selection of transformants. Expression of a patchoulol synthase can be achieved using a basidiomycete promoter, e.g. a constitutive promoter or an inducible promoter. An example of a strong constitutive promoter is the glyceraldehyde-3-phosphate dehydrogenase (gpdA) promoter. This promoter is preferred for constitutive expression when recombinant DNA material is expressed in a basidiomycete host. Other examples are the phosphoglycerate kinase (pgk) promoter, the pyruvate kinase (pki) promoter, TPI, the triose phosphate isomerase (tpi) promoter, the APC synthetase subunit g (oliC) promoter, the sc3 promoter and the acetamidase (amdS) promoter of a basidiomycete (WO 96/41882).

If needed, the primary nucleotide sequence of the patchoulol synthase gene can be adapted to the codon usage of the basidiomycete host.

Further, expression can be directed especially to the (monokaryotic) mycelium or to the (dikaryotic) fruiting bodies. In the latter case, the Fbh1 promoter of *Pleurotis* is especially useful (Penas, M. M. et al., Mycologia (2004) 96: 75-82).

Methodologies for the construction of plant transformation constructs are described in the art. Overexpression can be achieved by insertion of one or more than one extra copy of the selected gene. It is not unknown for plants or their progeny, originally transformed with one or more than one extra copy of a nucleotide sequence to exhibit overexpression.

Obtaining sufficient levels of transgenic expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell or tissue. In some cases, expression in multiple tissues is desirable, and constitutive promoters such as the 35S promoter series may be used in this respect. However, in some of the embodiments of the present invention it is preferred that the expression in transgenic plants is leaf-specific, more preferably, the expression of the gene occurs in the leaf plastids. The promoter of the isoprene synthase gene from *Populus alba* (PaIspS) (Sasaki et al., FEBS Letters (2005) 579: 2514-2518) appears to drive plastid-specific expression. Hence, this promoter is a very suitable promoter for use in an expression vector of the present invention.

Other suitable leaf-specific promoters are the rbcS (Rubisco) promoter (e.g. from coffee, see WO 02/092822); from *Brassica*, see U.S. Pat. No. 7,115,733; from soybean, see Dhanker, O., et al., Nature Biotechnol. (2002) 20: 1140-1145), the cy-FBPase promoter (see U.S. Pat. No. 6,229,067), the promoter sequence of the light-harvesting chlorophyll a/b binding protein from oil-palm (see US 2006/0288409), the STP3 promoter from *Arabidopsis thaliana* (see, Büttner, M. et al., Plant cell & Environ. (2001) 23: 175-184), the promoter of the bean PAL2 gene (see Sablowski, R. W. et al., Proc. Natl. Acad. Sci. USA (1995) 92: 6901-6905), enhancer sequences of the potato ST-LS1 promoter (see Stockhaus, J. et al., Proc. Natl. Acad. Sci. USA (1985) 84: 7943-7947), the wheat CAB1 promoter (see Gotor, C. et al., Plant J. (1993) 3: 509-518), the stomata-specific promoter from the potato ADP-glucose-phosphorylase gene (see U.S. Pat. No. 5,538,879), the LPSE1 element from the P(D540) gene of rice (see CN 2007/10051443), and the stomata specific promoter, pGC1 (At1g22690) from *Arabidopsis thaliana* (see Yang, Y. et al., Plant Methods (2008) 4: 6).

Plant species may, for instance, be transformed by the DNA-mediated transformation of plant cell protoplasts and subsequent regeneration of the plant from the transformed protoplasts in accordance with procedures well known in the art.

Further examples of methods of transforming plant cells include microinjection (Crossway et al., Mol. Gen. Genet. (1986) 202: 179-185), electroporation (Riggs, C. D. and Bates, G. W., Proc. Natl. Acad. Sci. USA (1986), 83: 5602-5606), *Agrobacterium*-mediated transformation (Hinchee et al., Bio/Technol. (1988) 6: 915-922), direct gene transfer (Paszkowski, J. et al., EMBO J. (1984) 3: 2717-2722), and ballistic particle acceleration using devices available from Agracetus, Inc., Madison, Wis. and BioRad, Hercules, Calif. (see, for example, Sanford et al., U.S. Pat. No. 4,945,050 and European Patent Application EP 0 332 581).

It is also possible to employ the protoplast transformation method for maize (European Patent Application EP 0 292 435, U.S. Pat. No. 5,350,689).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti et al., Bio/technol. (1985) 3: 241; Byrne M. C. et al., Plant Cell Tissue and Organ Culture (1987) 8: 3-15; Sukhapinda, K. et al., Plant Mol. Biol. (1987) 8: 209-217; Hiei, Y. et al., The Plant J. (1994) 6: 271-282). The use of T-DNA to transform plant cells has received extensive study and is amply described (e.g. EP-A 120 516). For introduction into plants, the chimeric genes of the invention can be inserted into binary vectors as described in the examples.

Other transformation methods are available to those skilled in the art, such as direct uptake of foreign DNA constructs (see EP-A 295 959), techniques of electroporation (Fromm, M. E. et al., Nature (1986), 319: 791-793) or high velocity ballistic bombardment with metal particles coated with the nucleic acid constructs (e.g. U.S. Pat. No. 4,945,050). Once transformed, the cells can be regenerated by those skilled in the art. Of particular relevance are the methods to transform foreign genes into commercially important crops, such as rapeseed (De Block, M. et al., Plant Physiol. (1989) 91: 694-701), sunflower (Everett, N. P. et al., Bio/Technology (1987) 5: 1201-1204), soybean (EP-A 301 749), rice (Hiei, Y. et al., The Plant J. (1994) 6: 271-282), and corn (Fromm et al., 1990, Bio/Technology 8: 833-839).

Those skilled in the art will appreciate that the choice of method might depend on the type of plant, i.e., monocotyledonous or dicotyledonous.

In another embodiment, the vector as described herein may be directly transformed into the plastid genome. Plastid transformation technology is extensively described in, U.S. Pat. Nos. 5,451,513, 5,545,817, 5,545,818 and WO 95/16783. The basic technique for chloroplast transformation involves introducing regions of cloned plastid DNA flanking a selectable marker together with the gene of interest into a suitable target tissue, e. g., using biolistics or protoplast transformation (e.g. calcium chloride or PEG mediated transformation).

*Agrobacterium tumefaciens* cells containing a vector according to the present invention, wherein the vector comprises a Ti plasmid, are useful in methods of making transformed plants. Plant cells are infected with an *Agrobacterium tumefaciens* as described above to produce a transformed plant cell, and then a plant is regenerated from the transformed plant cell. Numerous *Agrobacterium* vector systems useful in carrying out the present invention are known. These typically carry at least one T-DNA border sequence and include vectors such as pBIN19 (Bevan, Nucl. Acids Res. (1984) 12: 8711-8720).

Methods using either a form of direct gene transfer or *Agrobacterium*-mediated transfer usually, but not necessarily, are undertaken with a selectable marker which may provide resistance to an antibiotic (e. g. kanamycin, hygromycin or methotrexate) or a herbicide (e. g. phosphinothricin). The choice of selectable marker for plant transformation is not, however, critical to the invention.

General methods of culturing plant tissues are provided for example by Maki, K. Y. et al., Plant Physiol. (1993) 15: 473-497; and by Phillips, R. I. et al. In: Sprague G F, Dudley J W, eds. *Corn and corn improvement*. 3rd edn. Madison (1988) 345-387.

After transformation, the transgenic plant cells are placed in an appropriate selective medium for selection of transgenic cells which are then grown to callus. Shoots are grown from callus and plantlets generated from the shoot by growing in rooting medium. The particular marker used will allow for selection of transformed cells as compared to cells lacking the DNA which has been introduced.

To confirm the presence of the transgenes in transgenic cells and plants, a variety of assays may be performed. Such assays include, for example, "molecular biological" assays well known to those of skill in the art, such as Southern and Northern blotting, in situ hybridization and nucleic acid-based amplification methods such as PCR or RT-PCR and "biochemical" assays, such as detecting the presence of a protein product, e.g., by immunological means (ELISAs and Western blots) or by enzymatic function. The presence of enzymatically active patchoulol synthase may be established by chemical analysis of the volatile products (patchoulol) of the plant.

A patchoulol synthase according to the invention may be used for the industrial production of patchoulol, which patchoulol may be used per se as a flavour or aroma, e.g. in a food product, or as a fragrance, e.g. in a household product, or as an intermediate for the production of another isoprenoid, e.g. santalol.

A method for producing patchoulol according to the invention comprises preparing patchoulol in the presence of patchoulol synthase. In principle, such a method can be based on any technique for employing an enzyme in the preparation of a compound of interest.

The method can be a method wherein FPP or any of its precursors (such as farnesol, IPP, isopentenyl phosphate, 3-methylbut-3-en-1-ol and even mevalonate) is fed as a substrate to cells comprising the patchoulol synthase. Alternatively, the method can also be a method wherein use is made of a living organism that comprises an enzyme system capable of forming FPP from a suitable carbon source, thus establishing a full fermentative route to patchoulol. It should be noted that the term "fermentative" is used herein in a broad sense for processes wherein use is made of a culture of an organism to synthesise a compound from a suitable feedstock (e.g. a carbohydrate, an amino acid source, a fatty acid source). Thus, fermentative processes as meant herein are not limited to anaerobic conditions, and extended to processes under aerobic conditions. Suitable feedstocks are generally known for specific species of (micro-)organisms.

Also, use may be made of the patchoulol synthase isolated from the cell wherein it has been produced, e.g. in a reaction system wherein the substrate (FPP) and the patchoulol synthase are contacted under suitable conditions (pH, solvent, temperature), which conditions may be based on the prior art referred to herein and the present disclosure, optionally in combination with some routine testing. The patchoulol synthase may e.g. be solubilised in an aqueous medium wherein also the FPP is present or the patchoulol synthase may be immobilised on a support material in a manner known in the art and then contacted with a liquid comprising the FPP. Since the enzyme has a high activity and/or selectivity towards the catalysis from FPP to patchoulol, the present invention is also advantageous for such an in vitro method, not only under acidic conditions, but also in case the pH is about neutral or alkaline. Suitable conditions may be based on known methodology for known patchoulol synthases, e.g. referred to in the literature referred to herein, the information disclosed herein, common general knowledge and optionally some routine experimentation.

In a particularly advantageous method of the invention, patchoulol is fermentatively prepared, i.e. by cultivating cells expressing patchoulol synthase in a culture medium. The actual reaction catalysed by the patchoulol synthase may take place intracellularly or—if the patchoulol synthase is excreted into the culture medium—extracellularly in the culture medium.

The cells used for in a method for preparing patchoulol according to the invention may in particular be host cells according to the invention. If desired, these host cells may be engineered to supply the FPP to the patchoulol synthase in increased amounts. This can for instance be done by enhancing the flux of carbon towards FPP, which in itself can be realized in different ways. In host cells with an endogenous DXP pathway (like *E. coli* and *R. sphaeroides*) deregulation of the expression of these pathway's enzymes can have a clear positive effect on isoprenoids formation. Overexpression of dxs encoding 1-deoxy-D-xylulose-5-phosphate synthase (DXP-synthases), the first enzyme of the DXP pathway and thus one of the main targets for metabolic engineering, has resulted in increased biosynthesis of several isoprenoids (e.g., Matthews and Wurtzel, Appl. Microbiol. Biotechnol. (2000) 53: 396-400; Huang et al., Bioorg. Med. Chem. (2001) 9: 2237-2242; Harker and Bramley, FEBS Lett (1999) 448: 115-119; Jones et, al. Metab. Eng. (2000) 2: 328-338; and Yuan et al. Metab. Eng. (2006) 8: 79-90). Also overexpression of dxr coding for DXP isomeroreductase (also known as 1-deoxy-D-xylulose-5-phosphate reductoisomerase), the enzyme catalyzing the second and committed step in the DXP pathway, can lead to increased isoprenoid production (Albrecht et al., Biotechnol. Lett. (1999) 21: 791-795), which effect can be further increased by co-overexpressing dxs at the same time (Kim & Keasling, Biotechnol Bioeng (2001) 72: 408-415). A positive effect on isoprenoid biosynthesis was further obtained by overexpression of isopentenyl diphosphate isomerase (IPP isomerase, Idi), the enzyme that catalyzes the interconversion of IPP to dimethylallyl diphosphate, DMAPP (e.g., Kajiwara et al. Biochem. J. (1997) 324: 421-426); Misawa and Shimada, J. Biotech. (1998) 59: 169-181; and Yuan et al. Metab. Eng. (2006) 8: 79-90) and the enzymes MEP cytidylyltransferase (also known as 4-diphosphocytidyl-2-C-methyl-D-erythritol synthase, IspD) and 2C-methyl-D-erythritol 2,4-cyclodiphosphate synthase (IspF), that are transcribed as one operon ispDF in *E. coli* (Yuan et al. Metab. Eng. (2006) 8: 79-90).

An alternative and more efficient approach to engineer strains with an endogenous DXP pathway for high-level production of isoprenoids is the introduction of a heterologous mevalonate pathway. Coexpression in *E. coli* of the *Saccharomyces cerevisiae* mevalonate pathway with a synthetic amorpha-4,11-diene synthase gene resulted in the formation of the sesquiterpene amorphadiene in titres of more than 110 mg/L when the recombinant *E. coli* strain was cultivated in an LB+ glycerol medium (Martin et al. Nat. Biotechnol. (2003) 21: 796-802). This *E. coli* strain was subsequently improved by the introduction of extra copies of the gene tHMG1 encoding the C-terminal catalytic domain of the yeast enzyme 3-hydroxy-3-methyl-glutaryl-coenzyme A (HMG-CoA) reductase. By increasing the formation and thus the activity of this enzyme, the intracellular level of the toxic mevalonate pathway intermediate HMG-CoA was reduced thereby overcoming growth inhibition and leading to an increased production of mevalonate (Pitera et al. Metab. Eng. (2007) 9: 193-207). Further improvement of the flux through the heterologous mevalonate pathway was obtained by codon optimization of the first three genes of this pathway in combination with replacement of the wild-type lac promoter with the two-fold stronger lacUV5 promoter (Anthony et al. Met. Eng. (2009) 11: 13-19). The production of amorphadiene could be even more increased by replacing the yeast genes for HMG-CoA synthase and HMG-CoA reductase with the equivalent genes from the gram positive bacterium Staphylococcus aureus. In combination with an optimized fermentation protocol, cultivation of this novel engineered E. coli strain yielded an amorphadiene titre of 27.4 g/L (Tsuruta et al. PloS ONE (2009) 4(2): e4489. doi:10.1371/journal.pone.0004489). Similarly, an E. coli strain engineered with the mevalonate pathway from Streptococcus pneumoniae in combination with the Agrobacterium tumefaciens decaprenyl diphosphate synthase (ddsA) gene produced coenzyme $Q_{10}$ ($CoQ_{10}$) in more than 2400 µg/g cell dry weight (Zahiri et al. Met. Eng. (2006) 8: 406-416. Increased production of $CoQ_{10}$ to was also obtained by engineering a Rhodobacter sphaeroides strain with the mevalonate pathway from Paracoccus zeaxanthinifaciens in its native (WO 2005/005650) and a mutated form (WO 2006/018211).

Also host cells with an endogenous MEV pathway (like S. cerevisiae) have been the subject of multiple engineering studies to obtain isoprenoid hyper producing strains. Introduction into S. cerevisiae of the heterologous E. coli derived DXP pathway in combination with the gene encoding the Citrus patchoulol synthase resulted in a strain accumulating approximately 10-fold more patchoulol compared to the strain expressing only the patchoulol synthase (WO 2007/093962). Most improvements in the industrially-important yeasts Candida utilis and S. cerevisiae, however, have centred on the engineering of the homologous MEV pathway. Especially overexpression of the enzyme HMG-CoA reductase, which is believed to be the main regulatory enzyme in the DXP pathway, in its full-length or truncated version, has appeared to be an efficient method to increase production of isoprenoids. This stimulating effect of overexpression of the N-terminal truncated HMG-CoA reductase has, for instance, been observed in case of lycopene production in C. utilis (Shimada et al. Appl. Env. Microbiol. (1998) 64: 2676-2680) and epi-cedrol production in S. cerevisiae (Jackson et al. Org. Lett. (2003) 5: 1629-1632). In the last case, the production of this sesquiterpene could be further enhanced by introduction of upc2-1, an allele that elicitates an increase in the metabolic flux to sterol biosynthesis. Another method to increase the flux through the MEV pathway is the employment of a mevalonate kinase variant that is less sensitive for feedback inhibition by FPP and other isoprenoid precursors. WO 2006/063752, for instance, shows that Paracoccus zeaxanthinifaciens R114, a bacterium with an endogenous MEV pathway, after introduction of the S. cerevisiae mevalonate kinase mutant N66K/I152M and the ddsA gene from P. zeaxanthinifaciens ATCC 21588 produces significantly more coenzyme $Q_{10}$ than the corresponding P. zeaxanthinifaciens strain expressing the wild type S. cerevisiae mevalonate kinase. Similar positive results on $CoQ_{10}$ production with P. zeaxanthinifaciens R114 have also been obtained with the feedback resistant variant K93E of the P. zeaxanthinifaciens mevalonate kinase (WO 2004/111214).

A second approach to increased amounts of FPP is based on reducing or elimination of enzymatic side activities on FPP. In yeast the gene ERG9 encodes the enzyme farnesyl diphosphate farnesyl transferase (squalene synthase), which catalyzes the condensation of two farnesyl diphosphate moieties to form squalene. Because this is the first step after FPP in the sterol biosynthesis and thus regulates the flux of isoprene units into the sterol pathway, ERG9 is a frequent target in yeast metabolic engineering for increased sesquiterpene and carotenoids production. Disruption of ERG9 in combination with overexpression of the tHMG-CoA reductase in the yeast C. utilis led to increased production of lycopene (Shimoda et al. Appl. Env. Microbiol. (1998) 64: 2676-2680). A similar combination of overexpression of tHMG-CoA reductase and downregulation of ERG9 using a methionine repressible promoter increased the production of the sesquiterpene amorphadiene in yeast with approx. 10-fold as compared to the yeast strain only expressing the amorphadiene synthase gene (Ro et al. Nature (2006) 440: 940-943; Lenihan et al. Biotechnol Prog. (2008) 24: 1026-1032). Since ergosterol is vital for yeast growth and yeast cells cannot assimilate externally fed ergosterol during aerobic growth, downregulation/knockout of ERG9 is frequently combined with mutations that equip the yeast strain with efficient aerobic uptake of ergosterol from the culture medium. Examples are the sue allele (Takahishi et al. Biotechnol. Bioeng. (2007) 97: 170-181) and the upc2-1 allele (Jackson et al. Org. Lett. (2003) 5: 1629-1632). Takahashi et al (Biotechnol. Bioeng. (2007) 97: 170-181) also investigated the effect of limiting the endogenous phosphatase activity by knocking out the phosphatase gene dpp1 in yeast. Although this knockout clearly limited the dephosphorylation of FPP reflected by much less farnesol accumulation, it did not improve sesquiterpene production beyond that of the combined erg9/sue mutations under the growth conditions applied.

Reaction conditions for fermentatively preparing patchoulol may be chosen depending upon known conditions for the species of host cell used (e.g. Rhodobacter capsulatus, Rhodobacter sphaeroides, Paracoccus zeaxanthinifaciens, Escherichia, coli, Aspergillus nidulans, Aspergillus niger, Aspergillus oryzae, Saccharomyces cerevisiae, Penicillium chrysogenum, Phaffia rhodozyma and Pichia pastoris), the information disclosed herein, common general knowledge and optionally some routine experimentation.

In principle, the pH of the reaction medium (culture medium) used in a method according to the invention may be chosen within wide limits, as long as the patchoulol synthase (in the host cell) is active and displays a wanted specificity under the pH conditions. In case the method includes the use of cells, for expressing the patchoulol synthase, the pH is selected such that the cells are capable of performing its intended function or functions. The pH may in particular be chosen within the range of four pH units below neutral pH and two pH units above neutral pH, i.e. between pH 3 and pH 9 in case of an essentially aqueous system at 25° C. Good results have e.g. been achieved in an aqueous reaction medium having a pH in the range of 6.8 to 7.5.

A system is considered aqueous if water is the only solvent or the predominant solvent (>50 wt. %, in particular >90 wt. %, based on total liquids), wherein e.g. a minor amount of alcohol or another solvent (<50 wt. %, in particular <10 wt. %, based on total liquids) may be dissolved (e.g. as a carbon source, in case of a full fermentative approach) in such a concentration that micro-organisms which are present remain active.

In particular, in case a yeast and/or a fungus is used, acidic conditions may be preferred, in particular the pH may be in the range of pH 3 to pH 8, based on an essentially aqueous system at 25° C. If desired, the pH may be adjusted using an acid and/or a base or buffered with a suitable combination of an acid and a base.

Anaerobic conditions are herein defined as conditions without any oxygen or in which substantially no oxygen is consumed by the cultured cells, in particular a micro-organism, and usually corresponds to an oxygen consumption of less than 5 mmol/l·h, preferably to an oxygen consumption of less than 2.5 mmol/l·h, or more preferably less than 1 mmol/l·h. Aerobic conditions are conditions in which a sufficient level of oxygen for unrestricted growth is dissolved in the medium, able to support a rate of oxygen consumption of at least 10 mmol/l·h, more preferably more than 20 mmol/l·h, even more preferably more than 50 mmol/l·h, and most preferably more than 100 mmol/l·h.

Oxygen-limited conditions are defined as conditions in which the oxygen consumption is limited by the oxygen transfer from the gas to the liquid. The lower limit for oxygen-limited conditions is determined by the upper limit for anaerobic conditions, i.e. usually at least 1 mmol/l·h, and in particular at least 2.5 mmol/l·h, or at least 5 mmol/l·h. The upper limit for oxygen-limited conditions is determined by the lower limit for aerobic conditions, i.e. less than 100 mmol/l·h, less than 50 mmol/l·h, less than 20 mmol/l·h, or less than to 10 mmol/l·h.

Whether conditions are aerobic, anaerobic or oxygen-limited is dependent on the conditions under which the method is carried out, in particular by the amount and composition of ingoing gas flow, the actual mixing/mass transfer properties of the equipment used, the type of micro-organism used and the micro-organism density.

In principle, the temperature used is not critical, as long as the patchoulol synthase (in the cells), shows substantial activity. Generally, the temperature may be at least 0° C., in particular at least 15° C., more in particular at least 20° C. A desired maximum temperature depends upon the patchoulol synthase and the cells, in case of a method wherein use is made of cells for expressing the patchoulol synthase. The temperature is 70° or less, preferably 50° C. or less, more preferably 40° C. or less, in particular 35° C., or less.

In case of a fermentative process, the incubation conditions can be chosen within wide limits as long as the cells show sufficient activity and/or growth. This includes aerobic, oxygen-limited and anaerobic conditions.

In particular, if the catalytic reaction whereby patchoulol is formed, is carried out outside a host cell, a reaction medium comprising an organic solvent may be used in a high concentration (e.g. more than 50%, or more than 90 wt. %, based on total liquids), in case the patchoulol synthase that is used retains sufficient activity and specificity in such a medium.

If desired, patchoulol, pogostol, and elemol, produced in a method according to the invention, is recovered from the reaction medium, wherein it has been made. A suitable method is liquid-liquid extraction with an extracting liquid that is non-miscible with the reaction medium.

In particular, suitable (for extraction from an aqueous reaction medium) is extraction with a liquid organic solvent, such as a liquid hydrocarbon. From initial results it is apparent that this method is also suitable to extract the patchoulol and elemol, and preferably also pogostol from a reaction medium comprising cells according to the invention used for its production, without needing to lyse the cells for recovery of the patchoulol (or further product). In particular, the organic solvent may be selected from liquid alkanes, liquid long-chain alcohols (alcohols having at least 12 carbon atoms), and liquid esters of long-chain fatty acids (acids having at least 12 carbon atoms). Suitable liquid alkanes in particular include C6-C16 alkanes, such as hexane, octane, decane, dodecane, isododecane and hexadecane. Suitable long-chain aliphatic alcohol in particular include C12-C18 aliphatic alcohols, like oleyl alcohol and palmitoleyl alcohol. Suitable esters of long-chain fatty acids in particular include esters of C1-C4 alcohols of C12-C18 fatty acids, like isopropyl myristate, and ethyl oleate.

In an advantageous embodiment, patchoulol and elemol, and preferably also pogostol is produced in a reactor comprising a first liquid phase (the reaction phase), said first liquid phase containing cells according to the invention in which cells the patchoulol (or a further product) is produced, and a second liquid phase (organic phase that remains essentially phase-separated with the first phase when contacted), said second liquid phase being the extracting phase, for which the formed product has a higher affinity. This method is advantageous in that it allows in situ product recovery. Also, it contributes to preventing or at least reducing potential toxic effects of patchoulol and elemol, and preferably also pogostol to the cells, because due to the presence of the second phase, the patchoulol and elemol, and preferably also pogostol concentration in the reaction phase may be kept relatively low throughout the process. Finally, there are strong indications that the extracting phase contributes to extracting the patchoulol, pogostol, and elemol out of the reaction phase.

In a preferred method of the invention the extracting phase forms a layer on top of the reaction phase or is mixed with the reaction phase to form a dispersion of the reaction phase in the extracting phase or a dispersion of the extracting phase in the reaction phase. Thus, the extracting phase not only extracts product from the reaction phase, but also helps to reduce or completely avoid losses of the formed product from the reactor through the off-gas, that may occur if patchoulol is produced in the (aqueous) reaction phase or excreted into the (aqueous) reaction phase. Patchoulol is poorly soluble in water and therefore easily volatilizes from water. It is contemplated that patchoulol solvated in the organic phase (as a layer or dispersion) is at least substantially prevented from volatilization.

Suitable liquids for use as extracting phase combine a lower density than the reaction phase with a good biocompatibility (no interference with the viability of living cells), low volatility, and near absolute immiscibility with the aqueous reaction phase. Examples of suitable liquids for this application are liquid alkanes like decane, dodecane, isododecane, tetradecane, and hexadecane or long-chain aliphatic alcohols like oleyl alcohol, and palmitoleyl alcohol, or esters of long-chain fatty acids like isopropyl myristate, and ethyl oleate (see e.g. Asadollahi et al. (Biotechnol. Bioeng. (2008) 99: 666-677), Newman et al. (Biotechnol. Bioeng. (2006) 95: 684-691) and WO 2009/042070).

The patchoulol produced in accordance with the invention may be used as such, e.g. for use as a flavour or fragrance, or as an insect repellent, or may be used as a starting material for another compound, in particular another flavour or fragrance.

Further, the present disclosure is directed to a method for preparing patchoulol, pogostol, and elemol, the method comprising converting a polyprenyl diphosphate substrate into the patchoulol, pogostol, and elemol in the presence of an enzyme, the enzyme comprising a first segment comprising a tag-peptide and a second segment comprising a patchoulol synthase according to the invention. An enzyme comprising said first and said second segment may herein be referred to as a 'tagged enzyme'.

For patchoulol pogostol, and elemol preparation in particular use can be made of a method, an amino acid sequence, a nucleic acid sequence or a host cell as described herein. Santalol can, for instance, be prepared by oxygenation/oxidation of patchoulol in a manner known per se.

The tag-peptide is preferably selected from the group of nitrogen utilization proteins (NusA), thioredoxins (Trx), maltose-binding proteins (MBP), Glutathione S-transferases (GST), Small Ubiquitin-like Modifier (SUMO) or Calcium-binding proteins (Fh8), and functional homologues thereof. As used herein a functional homologue of a tag peptide is a tag peptide having at least about the same effect on the solubility of the tagged enzyme, compared to the non-tagged enzyme. Typically the homologue differs in that one or more amino acids have been inserted, substituted, deleted from or extended to the peptide of which it is a homologue. The homologue may in particular comprise one or more substitutions of a hydrophilic amino acid for another hydrophilic amino acid or of a hydrophobic amino acid for another. The homologue may in particular have a sequence identity of at least 40%, more in particular of at least 50%, preferably of at least 55%, more preferably of at least 60%, at least 70%, at least 75%, at least 80%, at least 85%, at least 90%, at least 95%, at least 98% or at least 99% with the sequence of a NusA, Trx, MBP, GST, SUMO or Fh8.

Particularly suitable is maltose binding protein from *Escherichia coli*, or a functional homologue thereof.

The use of a tagged enzyme according to the invention is in particular advantageous in that it may contribute to an increased production, especially increased cellular production of a terpenoid or a terpene, such as patchoulol, pogostol, and elemol.

For improved solubility of the tagged enzyme (compared to the enzyme without the tag), the first segment of the enzyme is preferably bound at its C-terminus to the N-terminus of the second segment. Alternatively, the first segment of the tagged enzyme is bound at its N-terminus to the C-terminus of the second segment.

Further, the present disclosure is directed to a nucleic acid comprising a nucleotide sequence encoding a polypeptide, the polypeptide comprising a first segment comprising a tag-peptide, preferably an MBP, a NusA, a Trx, a GST, a SUMO or anFh8-tag or a functional homologue of any of these, and a second segment comprising a patchoulol synthase. The second segment may for instance comprise an amino acid sequence as shown in SEQ ID NO: 3, or a functional analogue thereof.

Further, the present disclosure is directed to a host cell comprising said nucleic acid encoding said tagged patchoulol synthase. Specific nucleic acids according to the invention encoding a tagged enzyme are shown in SEQ ID NO: 10, SEQ ID NO: 14, SEQ ID NO: 18, SEQ ID NO: 22, SEQ ID NO: 26, and SEQ ID NO: 30. The host cell may in particular comprise a gene comprising any of these sequences or a functional analogue thereof.

Further, the present disclosure is directed to an enzyme, comprising a first segment comprising a tag-peptide and a second segment comprising a polypeptide having enzymatic activity for converting a polyprenyl diphosphate into a terpene, in particular a patchoulol synthase, the tag-peptide preferably being selected from the group of MBP, NusA, Trx or SET). Specific enzymes comprising a tagged enzyme according to the invention are shown in SEQ ID NO: 11, SEQ ID NO: 15, SEQ ID NO: 19, SEQ ID NO: 23, SEQ ID NO: 27, and SEQ ID NO: 31.

The invention will now be illustrated by the following examples.

FIGURE LEGENDS

Figure 2:
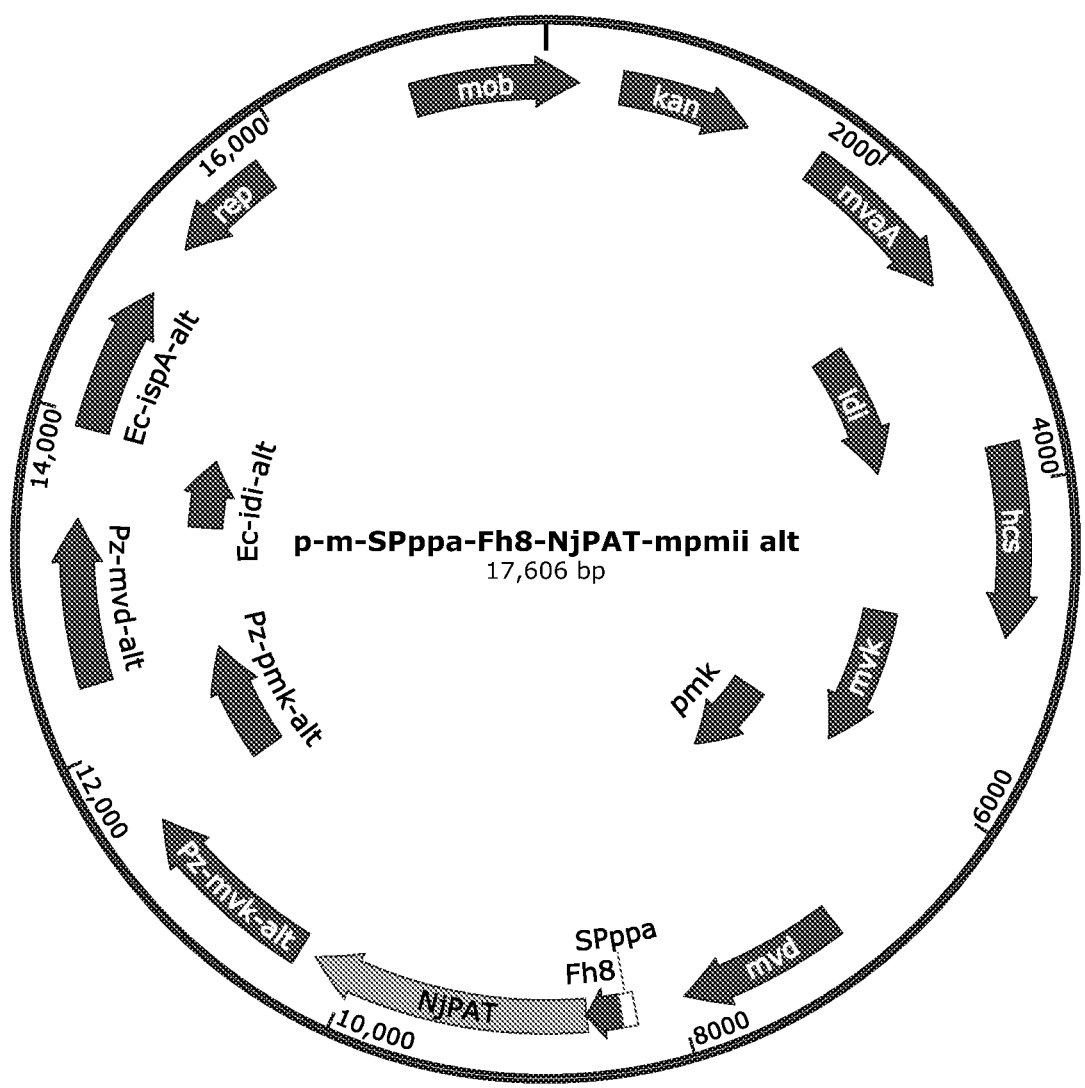
Figure 3:
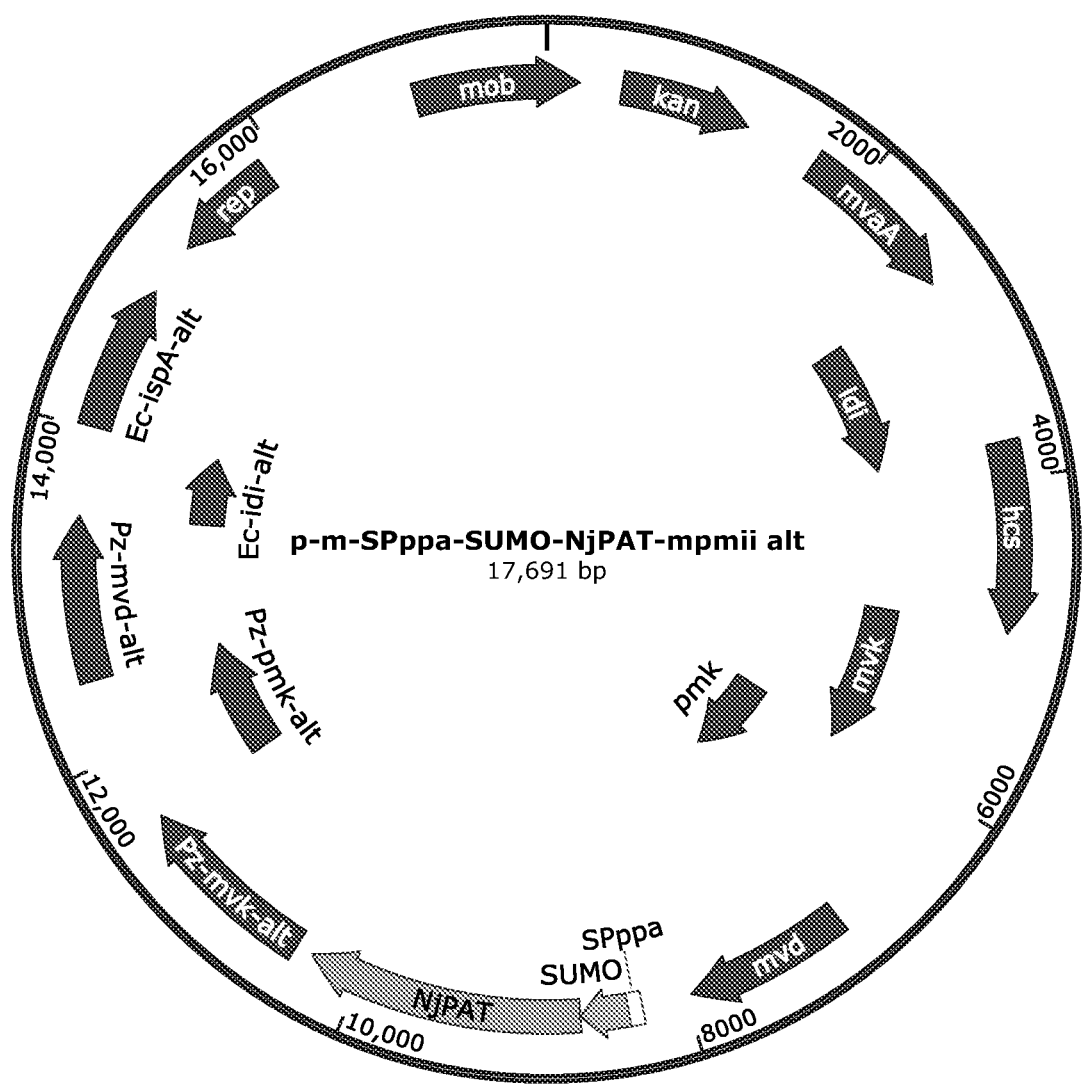
Figure 4:
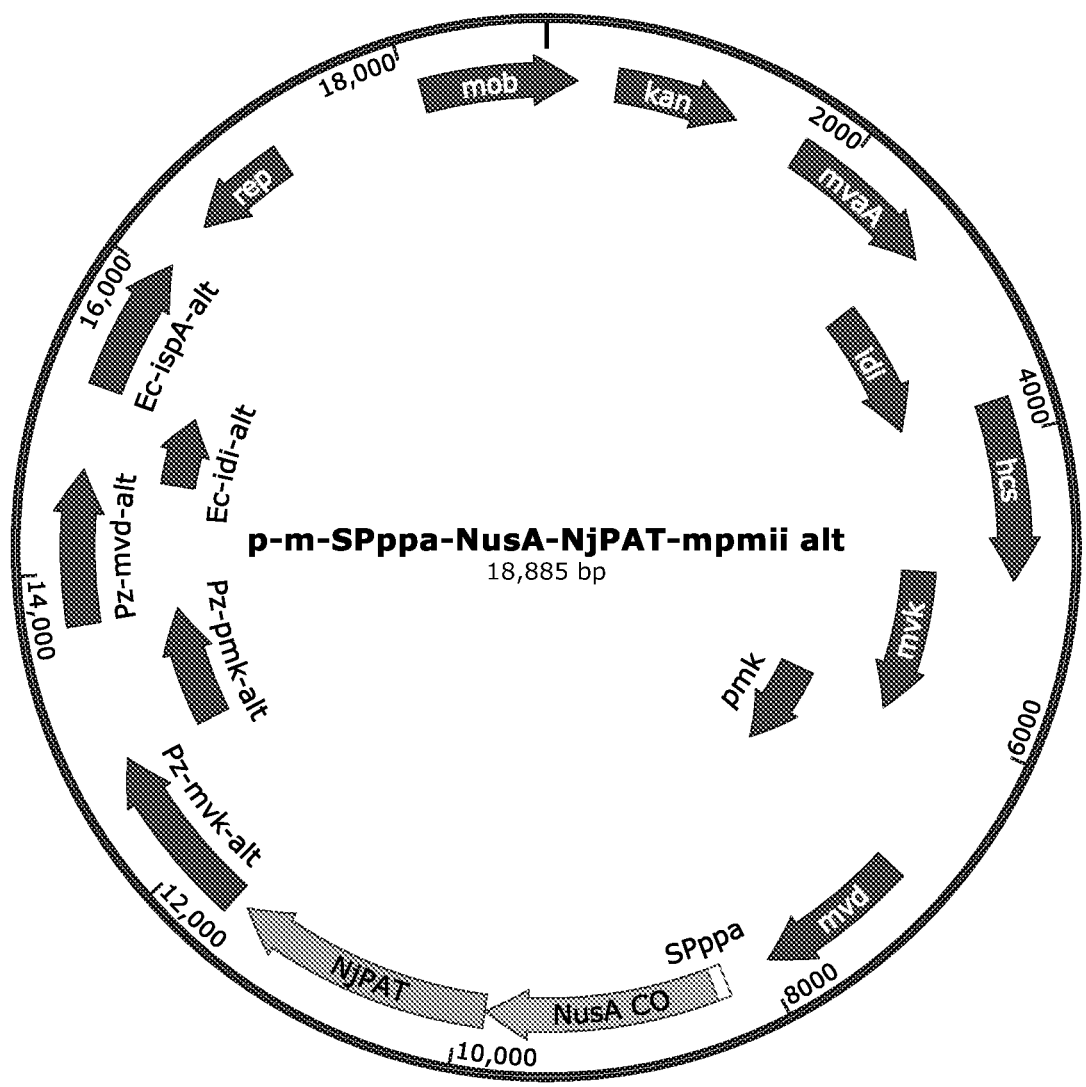
Figure 5:
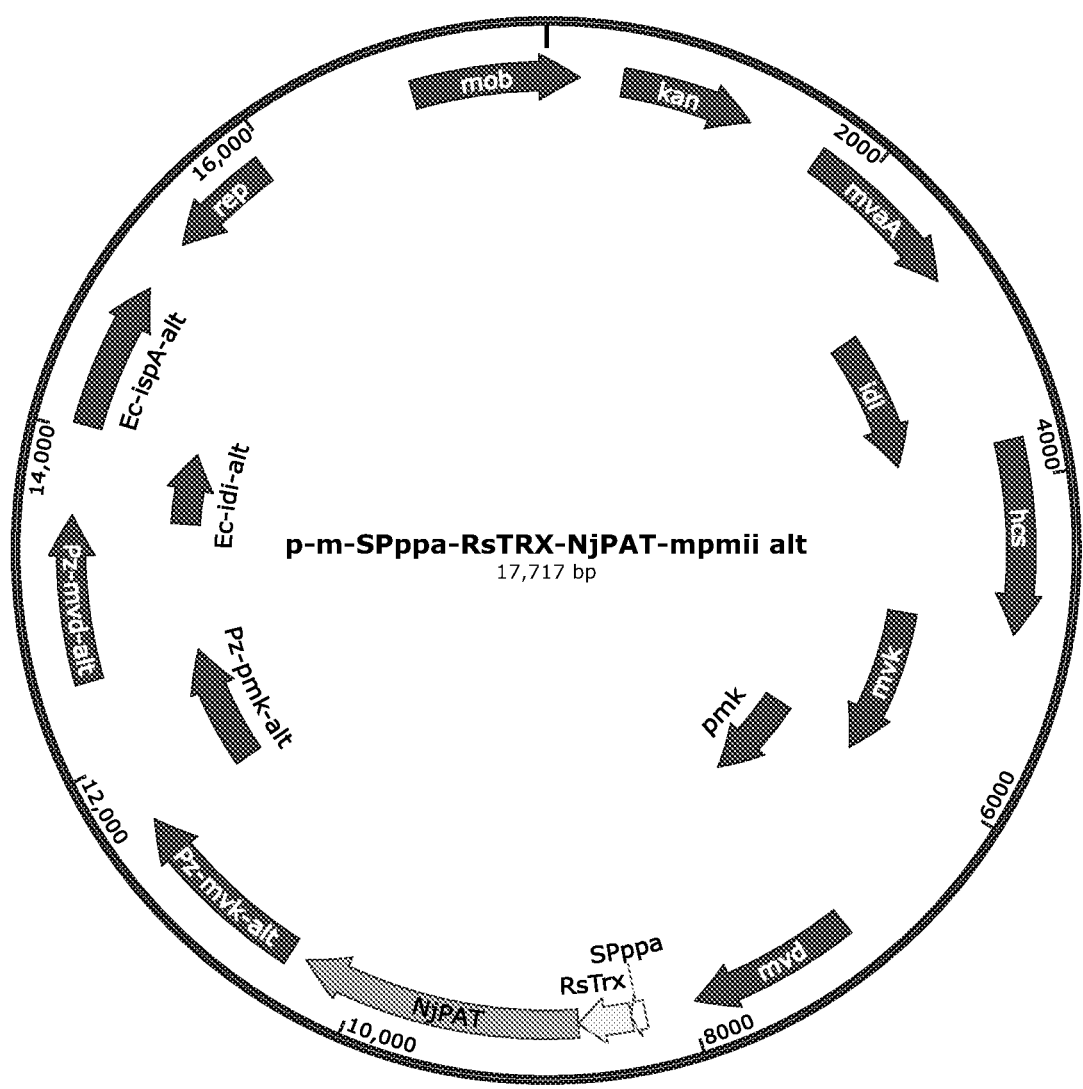
Figure 6:
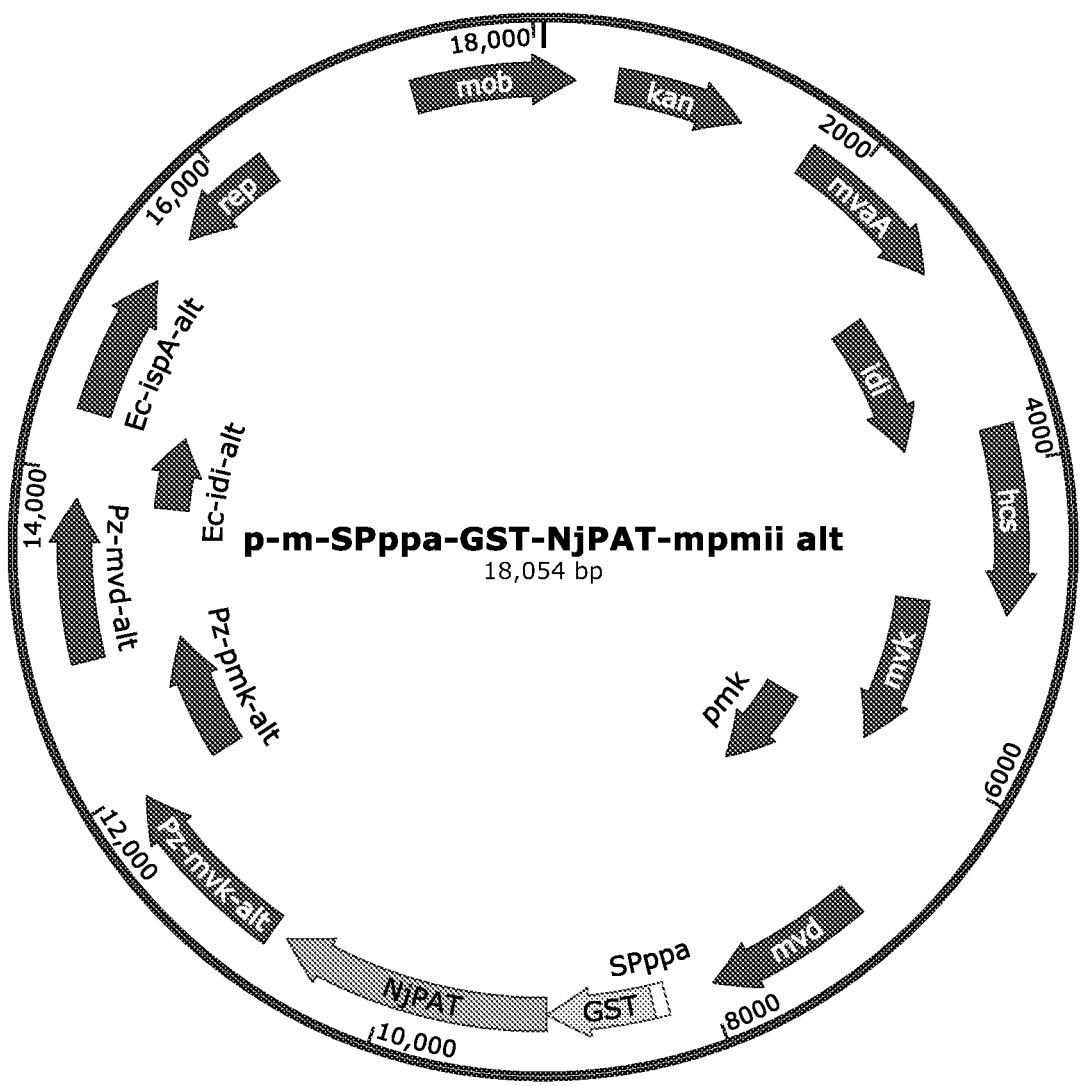
Figure 7:
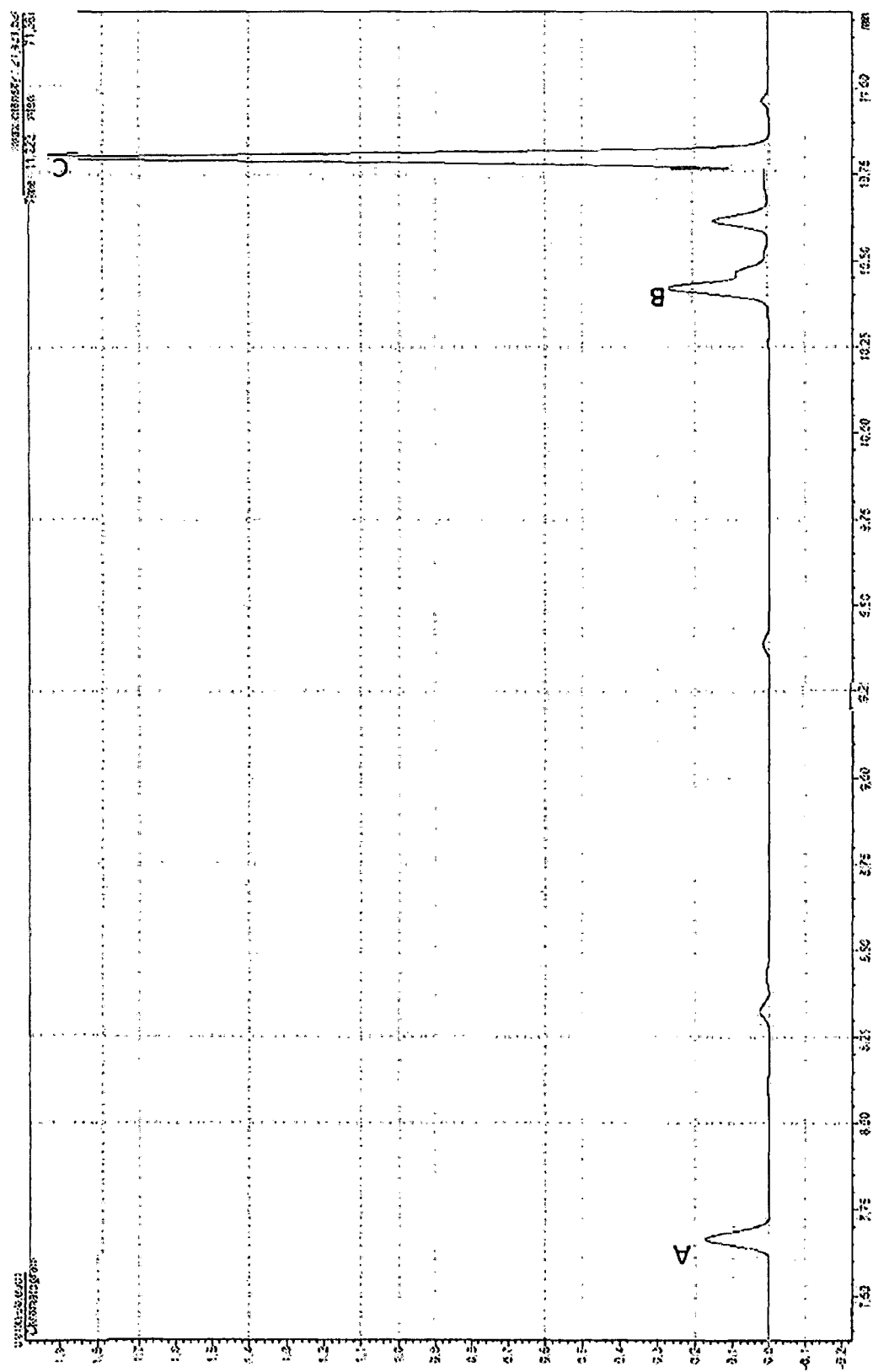
Figure 8:
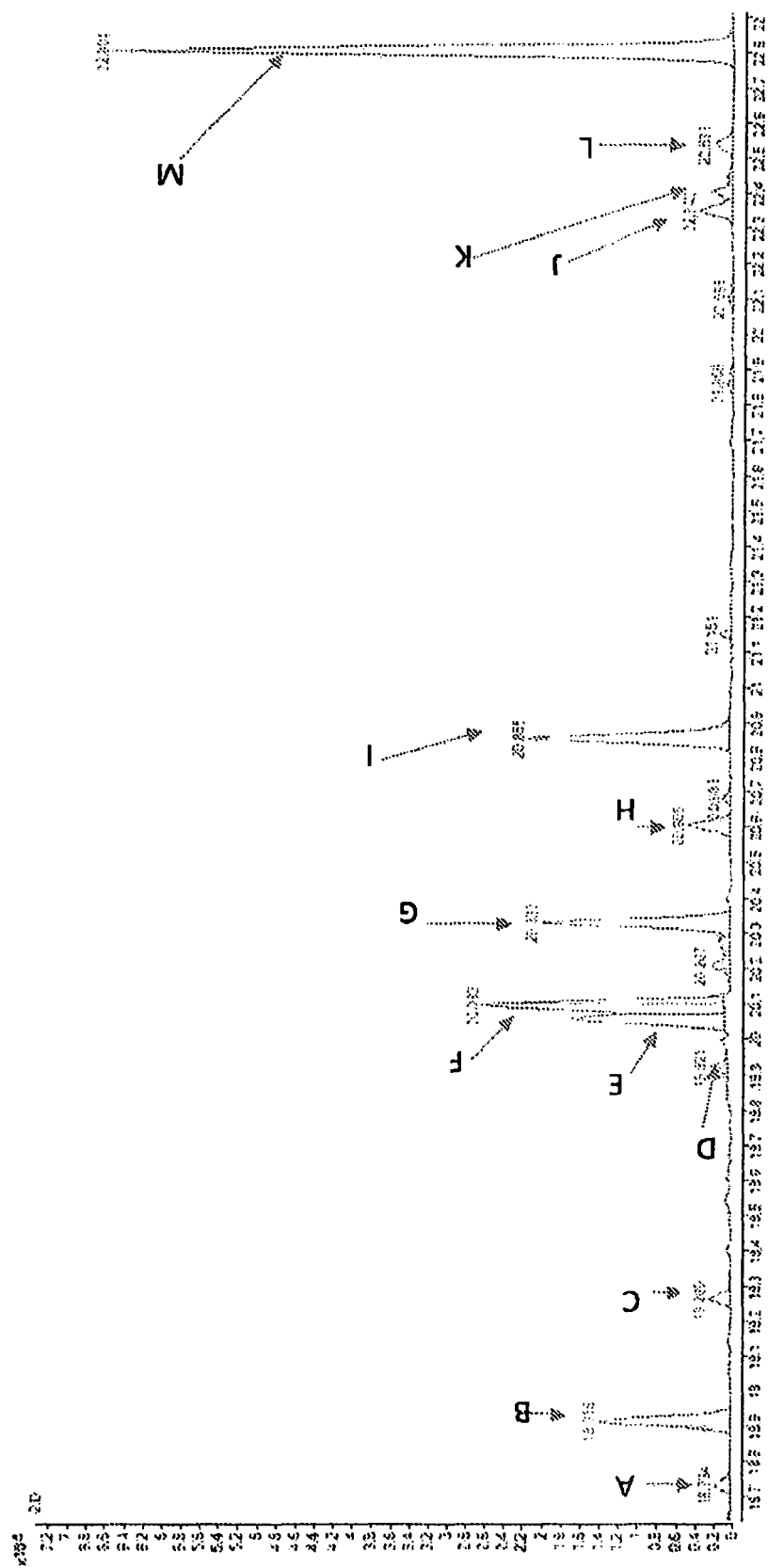

FIG. 1: genetic map showing the features of the plasmid p-m-SPppa-MBP-NjPAT-mpmii alt in which the NjPAT gene is fused to the MBP tag and regulated by the promoter SPppa FIG. 2: genetic map showing the features of the plasmid p-m-SPppa-Fh8-NjPAT-mpmii alt in which the NjPAT gene is fused to the Fh8 tag and regulated by the promoter SPppa FIG. 3: genetic map showing the features of the plasmid p-m-SPppa-SUMO-NjPAT-mpmii alt in which the NjPAT gene is fused to the SUMO tag and regulated by the promoter SPppa FIG. 4: genetic map showing the features of the plasmid p-m-SPppa-NusA-NjPAT-mpmii alt in which the NjPAT gene is fused to the NusA tag and regulated by the promoter SPppa FIG. 5: genetic map showing the features of the plasmid p-m-SPppa-RsTRX-NjPAT-mpmii alt in which the NjPAT gene is fused to the RsTRX tag and regulated by the promoter SPppa FIG. 6: genetic map showing the features of the plasmid p-m-SPppa-GST-NjPAT-mpmii alt in which the NjPAT gene is fused to the GST tag and regulated by the promoter SPppa FIG. 7: GC-FID Chromatogram of NjPAT terpene alcohols extract. A: elemol; B: pogostol; C: patchoulol FIG. 8: GC-QTOF chromatogram of NjPAT extract. A: guaia-11-diene; B: β-patchoulene; C: bicyclogermacrene; D: seychellene; E: α-patchoulene; F: δ-patchoulene; G: δ-guaiene; H: γ-patchoulene; I: elemol; J: pogostol; K: isolongifolol acetate; L: viridiflorol/iedol; M: patchoulol.

EXAMPLES

Example 1

GC-MS Analysis of *Nardostachys jatamansi*

A *Nardostachys jatamansi* plant of about 20 cm tall was purchased from Poyntzfield Herb Nursery, Black Isle, By Dingwall IV7 8LX, Ross & Cromarty, Scotland. The plant was dissected in leaf and root material. 0.5 g of plant material was weighed in a precooled glass tube, and 2 mL of dichloromethane was added. The suspension was vortexed for 1 min, sonicated for 5 min in an ultrasonic bath and centrifuged for 5 min at 1500 g at room temperature. The supernatant was collected and filtered over a column of 1 g sodium sulphate. About 2 microliter was analysed by GC/MS using a gas chromatograph as described in detail by Cankar et al. (2015). Patchoulol was identified by the comparison of retention times and mass spectra to those of patchouli oil 5 (Sigma-Aldrich).

Results:

The roots of *N. jatamansi* appeared to contain compounds that correspond to patchoulol (Rt 16.4 min) and alpha patchoulene (Rt 13.9 min). Therefore, this tissue was further taken for extraction of RNA.

Example 2

RNA Extraction and Analysis

The RNA of *N. jatamansi* root material was isolated as follows: About 15 mL 20 extraction buffer (2% hexadecyl-trimethylammonium bromide, 2% polyvinylpyrrolidinone K 30, 100 mM Tris-HCl (pH 8.0), 25 mM EDTA, 2.0 M NaCl, 0.5 g/L spermidine and 2% β-mercaptoethanol) was warmed to 65° C., after which 3 g ground tissue was added and mixed. The mixture was extracted two times with an equal volume of chloroform:isoamylalcohol (1:24), and one-fourth volume of 10 M LiCl was added to the supernatant and mixed. The RNA was precipitated overnight at 4° C. and harvested by centrifugation at 10 000 g for 20 min. The pellet was dissolved in 500 microliter of SSTE [1.0 M NaCl, 0.5% SDS, 10 mM Tris-HCl (pH 8.0), 1 mM EDTA (pH 8.0)] and extracted once with an equal volume of chloroform:isoamylalcohol. Two volumes of ethanol were added to the supernatant, incubated for at least 2 h at −20° C., centrifuged at 13 000 g and the supernatant removed. The pellet was air-dried and resuspended in water. Total RNA (60 Vg) was shipped to Vertis Biotechnology AG (Freising, Germany). PolyA+ RNA was isolated, random primed cDNA synthesized using a randomized N6 adapter primer and M-MLV H-reverse transcriptase. cDNA was sheared and fractionated, 5 and fragments of a size of 500 bp were used for further analysis. The cDNAs carry attached to their 5' and 3' ends the adaptor sequences A and B as specified by Illumina.

The material was subsequently analysed on an Illumina MiSeq Sequencing device. In total, 28,331,910 sequences were read by the MiSeq, with a total sequence length of 11,064,059,151 basepairs. Trimmomatic-0.32 was used to trim sequences from Illumina sequencing adapters, Seqprep was used to overlap paired end sequences, and bowtie2 (version 2.2.1) was used to remove phiX contamination (phiX DNA is used as a spike-in control, usually present in <1%). Paired end reads and single reads were used in a Trinity assembly (trinityrnaseq-2.0.2). A total number of 160871 contigs were assembled by Trinity. In order to identify sesquiterpene synthases, the *N. jatamansi* contigs were used to create a database of cDNA sequences. In this database, the TBLASTN program was deployed to identify cDNA sequences that encode proteins that show identity with protein sequences of sesquiterpene synthases, including the patchoulol synthase from *Pogostemon cablin*, the patchoulol synthase from *Valeriana*. In total 77 contigs in the *N. jatamansi* cDNA database were identified which have significant homology to sesquiterpene synthases. These 77 contigs were further characterized by analyzing them using the BLASTX program to align them to protein sequences present in the UniProt database (downloaded Aug. 28, 2015), and 24 of them were identified as putative sesquiterpene synthase sequences and other 11 as putative monoterpene synthases, according to their homology to terpene synthases sequences present in UniProt. Contigs were screened for open reading frames encoding the full-length terpene synthase proteins, based on the alignments provided by the BLASTX analysis. Two full length putative sesquiterpene-synthase encoding RNA sequences were identified, one of them was contig 27692.

Example 3: Cloning of *Nardostachys jatamansi* Patchoulol Synthase (NjPAT)

Full length open reading frames were amplified from the cDNA of *N. jatamansi*. Forward and reverse primers as shown in Table 1 were designed and used to amplify total open reading frames in such a way that the reading frame was fused to the C-terminus of a His-6 tag in the plasmid pCDF-DUET-1 (Novagen corporation). A total of 5 different terpene synthase ORFs were cloned. Using the primers 27692-Fw (SEQ ID NO: 1) and 27692-Re (SEQ ID NO: 2), two different closely related cDNAs were cloned. One of these (pTS11-1) encoded a protein lacking 70 aminoacids, relative to the protein encoded by the contig 27692 described above. The other clone (pTS11-2) encompassed the cDNA sequence (SEQ ID NO: 3) which encoded the protein SEQ ID NO: 4.

The cloned variants were analysed by sequencing the TS insert. Different variants were introduced into chemical competent *E. coli* BL21-RIL (Stratagene), by heat shock transformation, and selected on LB-agar with 1% glucose, 50 ug/ml spectinomycin and 50 ul/ml chloramphenicol. Transformants were transferred to 5 ml LB liquid medium with 1% glucose 50 ug/ml spectinomycin and 50 ug/ml chloramphenicol and grown overnight at 37° C. and 250 rpm.

200 microliter of those cultures was transferred to 20 mL of 5 LB medium with the appropriate antibiotic in a 100 mL Erlenmeyer flask, and incubated at 37° C., 250 rpm until the A600 was 0.4 to 0.6. Subsequently, 1 mM IPTG was added and cultures were incubated overnight at 18° C. and 250 rpm. The next day, cells were harvested by centrifugation (10 min 8000×g), medium was removed, and cells were resuspended in 1 mL Resuspension buffer (50 mM Tris-HCl pH=7.5, 1.4 mM 6-mercaptoethanol; 4° C.). Cells were disrupted by shaking 2 times for 10 seconds with 0.2 g zirconium sand in a Fastprep machine at speed 6.5. Insoluble particles were subsequently removed by centrifugation (10 min 13,000×g, 4° C.). Soluble protein was immediately used for enzyme assays.

Example 4: In Vitro Enzyme Assay

For enzyme assays, in a glass tube a mix was made of 800 µL of MOPSO buffer (15 mM MOPSO (3-[N-morpholino]-2-hydroxypropane sulphonic acid) pH=7.0, 12.5% glycerol, 1 mM MgCl2, 0.1% tween 20, 1 mM ascorbic acid, 1 mM dithiothreitol), 100 microliter of purified enzyme solution and 5 µL of farnesyl diphosphate or geranyl diphosphate (10 mM, Sigma FPP dry-evaporated and dissolved in 50% ethanol) and 20 µL Na-orthovanadate 250 mM. This mix was incubated at 30° C. with mild agitation for 2 hours. Subsequently, the waterphase was extracted with 2 mL ethylacetate. Ethylacetate phase was collected, centrifuged at 1200×g, dried over a sodium sulphate column and analyzed by GC-MS.

The GC-MS analysis was performed on an Agilent Technologies system, comprising a 7980A GC system, a 597C inert MSD detector (70 eV), a 7683 auto-sampler and injector and a Phenomenex Zebron ZB-5 ms column of 30 m length×0.25 mm internal diameter and 0.25 µm stationary phase, with a Guardian precolumn (5 m). In this system, 1 microliter of the sample was injected. The injection chamber was at 250° C., the injection was splitless, and the ZB5 column was maintained at 45° C. for 2 minutes after which a gradient of 10° C. per minute was started, until 300° C. Peaks were detected in chromatograms of the total ion count. Compounds were identified by their retention index and by their mass spectrum in combination with comparison of the mass spectrum to libraries (NIST8 and in-house).

Clone TS11-2 was found to produce patchoulol in this in vitro assay, and thus to encode a patchoulol synthase, and was termed NjPAT. The closely related clone TS11-1 did not produce any sesquiterpenes in the in vitro assay.

Example 5: Cloning of NjPAT for the Expression in *Rhodobacter sphaeroides* with Solubility Tags For the expression of the NjPAT gene in combination with the different solubility tags under the regulation of promoter SPppa, the constructs SPppa-MBP, SPppa-Fh8, SPppa-SUMO, SPppa-NusA, SPppa-RsTRX and SPppa-GST, and the NjPAT gene were synthesized by Genscript USA Inc. (Piscataway, N.J., USA). Both NjPAT gene (SEQ ID NO:5) and all the sequences coding for the solubility tags were codon optimized for the expression in *R. sphaeroides*.

The plasmid p-m-SPppa-MBP-NjPAT-mpmii alt (FIG. 1) was obtained following a standard Infusion® protocol. Briefly, the construct SPppa-MBP was amplified using the primer Pppa-Fw (SEQ ID NO: 6)- and MBP_NjPAT_Rv (SEQ ID NO: 7). NjPAT was amplified with primers MBP_NjPAT_Fw (SEQ ID NO: 8) NjPAT_Rv (SEQ ID NO: 9). The vector p-m-mpmii alt was digested with restriction enzymes EcoRI and BamHI. The amplicons and the digested vector were then assembled using the InFusion® enzyme mix from Clontech. The reaction mixture was transformed into *E. coli* 517-1 cells. The nucleotide sequence of the construct SPppa-MBP-NjPAT is given in SEQ ID NO: 10; the protein sequence is represented in SEQ ID NO: 11.

The plasmid p-m-SPppa-Fh8-NjPAT-mpmii alt (FIG. 2) was obtained in a similar way to the plasmid p-m-SPppa-MBP-NjPAT-mpmii alt: the construct SPppa-Fh8 was amplified using the primer Pppa-Fw (SEQ ID NO: 6)- and Fh8_NjPAT_Rv (SEQ ID NO: 12) and the NjPAT gene was amplified with primers Fh8_NjPAT_Fw (SEQ ID NO: 13) NjPAT_Rv (SEQ ID NO: 9). The further cloning process was the same as for plasmid p-m-SPppa-MBP-NjPAT-mpmii alt. The nucleotide sequence of the construct SPppa-Fh8-NjPAT is given in SEQ ID NO: 14; the protein sequence is represented in SEQ ID NO: 15. The same cloning procedure was followed for the other constructs.

The construct SPppa-SUMO was amplified using the primer Pppa-Fw (SEQ ID NO: 6)- and SUMO_NjPAT_Rv (SEQ ID NO: 16) and the NjPAT gene was amplified with primers SUMO_NjPAT_Fw (SEQ ID NO: 17) NjPAT_Rv (SEQ ID NO: 9). The nucleotide sequence of the construct SPppa-SUMO-NjPAT is given in SEQ ID NO: 18; the protein sequence is represented in SEQ ID NO: 19. The map of the final plasmid p-m-SPppa-SUMO-NjPAT-mpmii alt is illustrated in FIG. 3.

The construct SPppa-NusA was amplified using the primer Pppa-Fw (SEQ ID NO: 6)- and NusA_NjPAT_Rv (SEQ ID NO: 20) and the NjPAT gene was amplified with primers NusA_NjPAT_Fw (SEQ ID NO: 21) NjPAT_Rv (SEQ ID NO: 9). The nucleotide sequence of the construct SPppa-NusA-NjPAT is given in SEQ ID NO: 22; the protein sequence is represented in SEQ ID NO: 23. The map of the final plasmid p-m-SPppa-NusA-NjPAT-mpmii alt is illustrated in FIG. 4.

The construct SPppa-RsTRX was amplified using the primer Pppa-Fw (SEQ ID NO: 6)- and RsTRX_NjPAT_Rv (SEQ ID NO: 24) and the NjPAT gene was amplified with primers RsTRX_NjPAT_Fw (SEQ ID NO: 25) NjPAT_Rv (SEQ ID NO: 9). The nucleotide sequence of the construct SPppa-RsTRX-NjPAT is given in SEQ ID NO: 26; the protein sequence is represented in SEQ ID NO: 27. The map of the final plasmid p-m-SPppa-RsTRX-NjPAT-mpmii alt is illustrated in FIG. 5.

The construct SPppa-GST was amplified using the primer Pppa-Fw (SEQ ID NO: 6)- and GST_NjPAT_Rv (SEQ ID NO: 28) and the NjPAT gene was amplified with primers GST_NjPAT_Fw (SEQ ID NO: 29) NjPAT_Rv (SEQ ID NO: 9). The nucleotide sequence of the construct SPppa-GST-NjPAT is given in SEQ ID NO: 30; the protein sequence is represented in SEQ ID NO: 31. The map of the final plasmid p-m-SPppa-GST-NjPAT-mpmii alt is illustrated in FIG. 6.

Transfer of the plasmids from S17-1 to *R. sphaeroides* Rs265-9c by conjugation was performed using standard procedures (U.S. Pat. No. 9,260,709B2).

Example 6: Growth Conditions Shake Flask Experiments

Seed cultures were performed in 100 ml shake flasks without baffles with 20 ml RS102 medium (U.S. Pat. No. 9,260,709B2) with 100 mg/L neomycin and a loop of glycerol stock. The flasks were grown for 72 hours at 30° C. in a shaking incubator with an orbit of 50 mm at 110 rpm.

At the end of the 72 hours, the OD600 of the culture was assessed in order to calculate the exact volume of culture to be transferred to the larger flasks.

Shake flask experiments were performed in 300 ml shake flasks with 2 bottom baffles. Twenty ml of RS102 medium and neomycin to a final concentration of 100 mg/L were added to the flask together with 2 ml of sterile n-dodecane. The volume of the inoculum was adjusted to obtain a final OD600 value of 0.05 in 20 ml medium.

The flasks were kept for 72 hours at 30° C. in a shaking incubator with an orbit of 50 mm at 110 rpm.

Example 7: Sample Preparation for Analysis of Isoprenoid Content in Organic Phase Cultures were collected 72 hours after inoculation in pre-weighted 50 ml PP tubes which were then centrifuged at 4500×g for 20 minutes. The n-dodecane layer was transferred to a microcentrifuge tube for later GC analysis.

Ten microliters of ethyl laureate were weighed in a 10-ml glass vial to which 800 µl of the isolated dodecane solution were added and weighed. Subsequently, 8 ml of acetone were added to the vial to dilute the dodecane concentration for a more accurate GC analysis. Approximately, 1.5 ml of the terpene-containing dodecane in acetone solution were transferred to a chromatography vial.

Example 8: Gas Chromatography Flame Ionization Detector (GC-FID)

Gas chromatography was performed on a Shimadzu GC2010 Plus equipped with a Restek RTX-5Sil MS capillary column (30 m×0.25 mm, 0.5 µm). The injector and FID detector temperatures were set to 280° C. and 300° C., respectively. Gas flow through the column was set at 40 mL/min. The oven initial temperature was 160° C., increased to 180° C. at a rate of 2° C./min, further increased to 300° C. at a rate of 50° C./min, and held at that temperature for 3 min. Injected sample volume was 1 µL with a 1:50 split-ratio, and the nitrogen makeup flow was 30 ml/min Example 9: Gas Chromatography Quantitative Time-of-Flight (GC-QTOF) Analysis of Terpenes Produced Byt NjPAT A stock solution of the dodecane extract from *R. sphaeroides* cultures was prepared at 1 mg/ml in hexane and then diluted to 20 µg/ml in methanol.

Two µl of the dilution were transferred to a Tenax tube, and drypurged for 2 h with a stream of 200 ml/minute helium, to remove solvent. The Tenax tube was desorbed using a Markes thermal desorber (Unity TD100) during 5 min at 240° C. to a coldtrap with multibed packing (0° C.). Trapped material was injected by heating at 40° C./sec to 260° C., with a splitflow of 9 ml/min and a column flow of 1.2 ml/min helium. Injected material was analyzed on a DB5 MS column (Agilent, 30 M, 0.25 mm id, 1 µm df) in an Agilent 7890B GC.

The temperature program was as follows: 2 min 40° C., then ramp at 10° C./min to 280° C. Compounds were detected using an Agilent 7200 QTOF MS with a mass range of 50-350 amu.

For data analysis Masshunter (Agilent, version B.07.00) was used. Deconvoluted spectra where compared with the NIST library (NIST version 2.2 2014)

Example 10: Analysis of Terpene Production by *R. sphaeroides* Strains

The *Rhodobacter* strain harbouring the plasmid p-m-SPppa-MBP-NjPAT-mpmii alt showed the highest production of terpene species, among which patchoulol, pogostol, and surprisingly elemol (FIG. 7). The ratio between patchoulol and elemol was 6.9:1, between patchoulol and pogostol 5.6:1 and finally between pogostol and elemol 1.3:1. The fusion of the Fhb tag to NjPAT completely inactivated the enzyme which could only produce farnesol (product coming from the dephosphorylation of FPP). The titre obtained with the strain expressing NjPAT with the solubility tag SUMO was 74% of that obtained with the MBP strain, and it was very similar to the 73% titre coming from the NusA-NjPAT strain. Lower titres were obtained when NjPAT was combined with GST or RsTRX (43% and 7% compared to the MBP-NjPAT titre, respectively)

The invention claimed is:

1. A patchoulol synthase having an amino acid sequence which has a sequence identity of at least 95% but less than 100% with SEQ ID NO: 4.

2. A nucleic acid, comprising a nucleic acid sequence encoding a patchoulol synthase according to claim 1, or a complementary sequence thereof.

3. A nucleic acid comprising a nucleic acid sequence as shown in SEQ ID NO: 5, or a nucleic acid sequence having a sequence identity of at least 95%, with the sequence shown in SEQ ID NO: 5, or a complementary sequence of any of these sequences.

4. An expression vector comprising the nucleic acid according to claim 2.

5. A host cell, which may be an organism or part of a multi-cellular organism, said host cell comprising an expression vector comprising the nucleic acid sequence according to claim 2.

6. The host cell according to claim 5, wherein the host cell is a bacterial cell selected from the group of Gram negative bacteria of *Rhodobacter, Paracoccus* and *Escherichia*.

7. The host cell according to claim 5, wherein the host cell is a fungal cell selected from the group of *Aspergillus, Blakeslea, Penicillium, Phaffia (Xanthophyllomyces), Pichia, Saccharomyces*, and *Yarrowia*.

8. A transgenic plant or culture comprising transgenic plant cells, said plant or culture comprising host cells according to claim 5, wherein the host cell is of a transgenic plant selected from the group consisting of *Nicotiana* spp, *Solanum* spp, *Cichorum intybus, Lactuca sativa, Mentha* spp, *Artemisia annua*, tuber forming plants, oil crops, liquid culture plants, tobacco BY2 cells, *Physcomitrella patens*, and trees.

9. A transgenic mushroom or culture comprising transgenic mushroom cells, said mushroom or culture comprising host cells according to claim 5, wherein the host cell is selected from the group consisting of *Schizophyllum, Agaricus* and *Pleurotis*.

10. A method for preparing patchoulol and elemol, and optionally pogostol, comprising converting a farnesyl diphosphate to patchoulol and elemol, and optionally pogostol in the presence of the patchoulol synthase according to claim 1.

11. The method for preparing patchoulol and elemol, and optionally pogostol according to claim 10, wherein the patchoulol and elemol, and optionally pogostol is prepared in a host cell, a plant or plant culture, or a mushroom or mushroom culture, expressing said patchoulol synthase.

12. The method according to claim 10, further comprising isolating the patchoulol and/or pogostol and/or elemol.

13. The method according to claim 10, wherein the method prepares elemol, patchoulol and pogostol, and wherein the ratio of pogostol to patchoulol is about 1:5.6.

14. The method according to claim 10, wherein the method prepares elemol and patchoulol, and wherein the elemol to patchoulol ratio is about 1:6.9.

15. The method according to claim 10, wherein the method prepares elemol and pogostol, and wherein the ratio of elemol to pogostol is about 1:1.3.

16. The patchoulol synthase according to claim 1, having at least 98% sequence identity with SEQ ID NO: 4.

17. A patchoulol synthase comprising an artificial fusion protein comprising a peptide or protein tag sequence and an amino acid sequence as shown in SEQ ID NO: 4 or a functional homologue thereof, said homologue being a patchoulol synthase comprising an amino acid sequence which has a sequence identity of at least 95% with SEQ ID NO: 4.

18. A nucleic acid, comprising a nucleic acid sequence encoding the patchoulol synthase according to claim 17, or a complementary sequence thereof.

19. The nucleic acid according to claim 18, wherein the nucleic acid comprises a nucleic acid sequence as shown in SEQ ID NO: 5, or a nucleic acid sequence having a sequence identity of at least 95% with the sequence of SEQ ID NO:5, or a complementary sequence of any of these sequences.

20. A method for preparing patchoulol and elemol, and pogostol, comprising converting a farnesyl diphosphate to patchoulol and elemol, and pogostol in the presence of a patchoulol synthase comprising an amino acid sequence as shown in SEQ ID NO: 4 or a functional homologue thereof, said homologue being a patchoulol synthase comprising an amino acid sequence which has a sequence identity of at least 95% with SEQ ID NO: 4, wherein the method prepares elemol, patchoulol and pogostol, and wherein the ratio of pogostol to patchoulol is higher than 1:5.

* * * * *